United States Patent
Pedersen et al.

(10) Patent No.: US 10,911,867 B2
(45) Date of Patent: Feb. 2, 2021

(54) IN-THE-EAR HEARING AID DEVICE, A HEARING AID, AND AN ELECTRO-ACOUSTIC TRANSDUCER

(71) Applicant: Oticon A/S, Smørum (DK)

(72) Inventors: Troels Holm Pedersen, Smørum (DK); Therese Schønemann Blom, Vanløse (DK); Seri Jalonen, Smørum (DK); Jan Thor Lunddahl Larsen, Smørum (DK); Niels Stubager Kiemer, Smørum (DK); Jesper B. Johansen, Smørum (DK); Povl Koch, Smørum (DK); Svend Oscar Petersen, Smørum (DK); Anders Erik Petersen, Smørum (DK); Kåre Tais Christensen, Smørum (DK); Antonello Salvatucci, Smørum (DK); Franz Treue, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 16/273,849

(22) Filed: Feb. 12, 2019

(65) Prior Publication Data
US 2019/0253793 A1 Aug. 15, 2019

(30) Foreign Application Priority Data

Feb. 13, 2018 (EP) ..................................... 18156412
Apr. 9, 2018 (EP) ..................................... 18166231

(51) Int. Cl.
*H04R 25/00* (2006.01)
*H04R 1/40* (2006.01)
(Continued)

(52) U.S. Cl.
CPC ............... *H04R 1/40* (2013.01); *H04R 25/55* (2013.01); *H04R 25/60* (2013.01); *A61B 5/6817* (2013.01);
(Continued)

(58) Field of Classification Search
CPC .. H04R 1/26; H04R 1/1016; H04R 2225/025; H04R 25/60; H04R 25/65; H04R 25/604; H04R 11/02; H04R 11/04; H04R 2460/13
See application file for complete search history.

(56) References Cited

U.S. PATENT DOCUMENTS 5,692,059 A * 11/1997 Kruger ................. H04R 1/1016
381/151
8,116,502 B2 * 2/2012 Saggio, Jr. ........... H04R 1/1016
381/380
(Continued)

FOREIGN PATENT DOCUMENTS

EP 3 169 082 A1 5/2017
WO WO 2010/120243 A1 10/2010
(Continued)

OTHER PUBLICATIONS

European Office Action issued in Application No. EP 19155980.6 dated Nov. 9, 2020.

*Primary Examiner* — Matthew A Eason
(74) *Attorney, Agent, or Firm* — Birch, Stewart, Kolasch & Birch, LLP

(57) ABSTRACT

An in-the-ear hearing aid device is disclosed. The device at least one electro-acoustic transducer, and at least one sensor or at least one active electronic component. The at least one electro-acoustic transducer comprises a capsule enclosing a transducer sound active part and a transducer air volume. The transducer air volume is air volume which is enclosed by said capsule and which is in fluid-connection with said transducer sound active part. At least a portion of said at least one sensor or of said at least one active electronic component is provided within said transducer air volume.

17 Claims, 36 Drawing Sheets

(51) Int. Cl.
  *A61B 5/00* (2006.01)
  *H04R 5/04* (2006.01)
  *H04R 1/10* (2006.01)

(52) U.S. Cl.
  CPC ............. *H04R 1/1016* (2013.01); *H04R 5/04* (2013.01); *H04R 2225/021* (2013.01); *H04R 2225/025* (2013.01)

(56) References Cited

U.S. PATENT DOCUMENTS

| | | | | |
|---|---|---|---|---|
| 8,194,911 | B2 * | 6/2012 | Dyer | H04R 1/1016 |
| | | | | 381/382 |
| 9,042,586 | B2 * | 5/2015 | Burns | H04R 25/00 |
| | | | | 381/328 |
| 2008/0205679 | A1 * | 8/2008 | Darbut | H04R 25/554 |
| | | | | 381/328 |
| 2010/0172529 | A1 * | 7/2010 | Burns | H04R 25/50 |
| | | | | 381/328 |
| 2011/0069852 | A1 * | 3/2011 | Arndt | H04R 25/48 |
| | | | | 381/317 |
| 2014/0205122 | A1 | 7/2014 | Stoffels et al. | |
| 2015/0256917 | A1 | 9/2015 | Schelling et al. | |
| 2017/0078781 | A1 * | 3/2017 | Qian | H04R 1/1091 |
| 2017/0095165 | A1 * | 4/2017 | Hirano | H04R 1/1016 |
| 2019/0014426 | A1 * | 1/2019 | Karamuk | H04R 25/602 |

FOREIGN PATENT DOCUMENTS

| | | |
|---|---|---|
| WO | WO 2011/000375 A1 | 1/2011 |
| WO | WO 2013/156539 A1 | 10/2013 |
| WO | WO 2017/118878 A1 | 7/2017 |

* cited by examiner

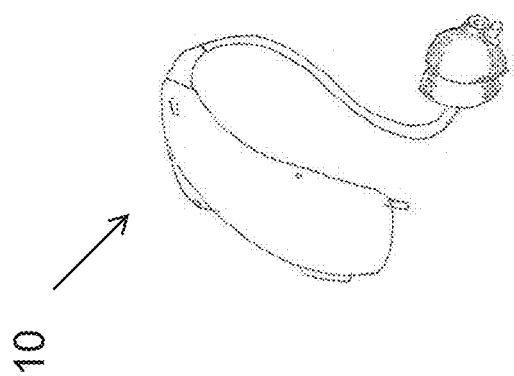
Fig. 27

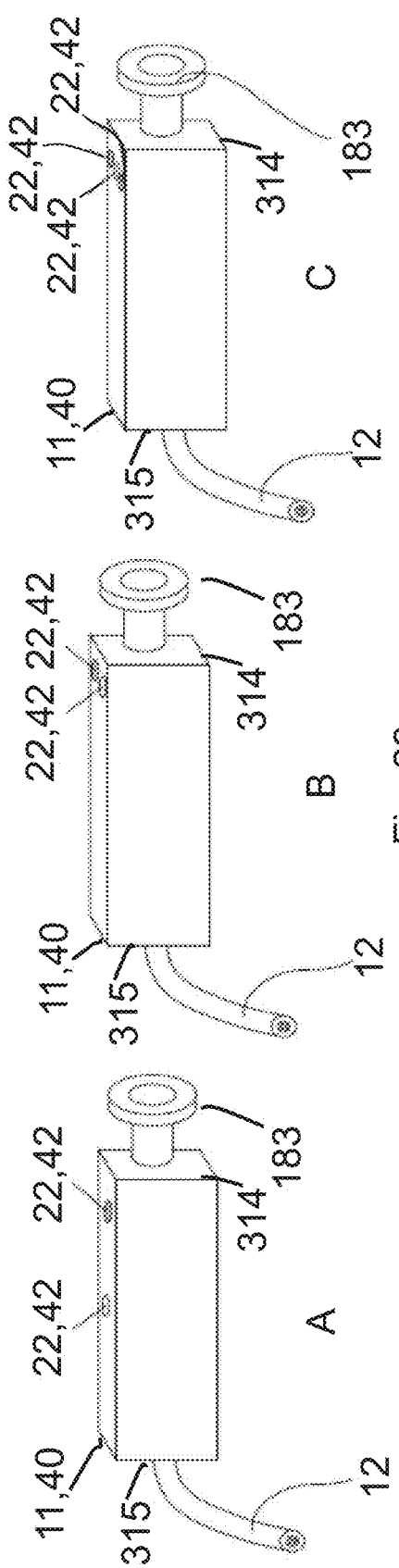
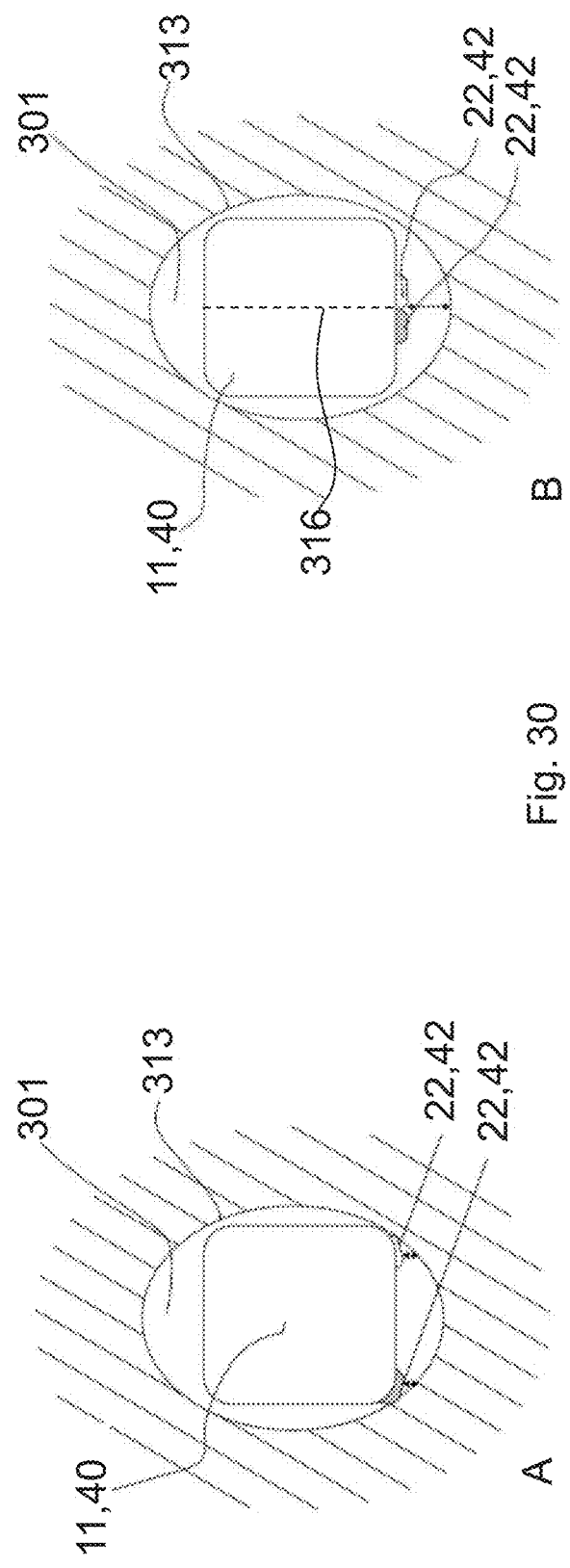
Fig. 29
Fig. 30

IN-THE-EAR HEARING AID DEVICE, A HEARING AID, AND AN ELECTRO-ACOUSTIC TRANSDUCER

TECHNICAL FIELD

The present disclosure generally relates to hearing aids having an in-the-ear hearing aid device which includes an electro-acoustic transducer, for instance, receiver-in-the-ear (RITE) hearing aids.

BACKGROUND

In-the-ear hearing aid devices comprise an exterior housing (of an in-the-ear unit thereof) and an electro-acoustic output transducer arranged therein. The electro-acoustic output transducer is called receiver and converts an electric audio signal into an acoustic sound signal. The electric audio signal may be provided by a sound processor. The sound processor may receive an electric audio input signal and process the electric audio input signal to thus generate a processed electric audio signal to be fed to the output transducer. The sound processor may be provided in a behind-the-ear (BTE) unit of the hearing aid. The electric audio input signal may be received from an electro-acoustic input transducer. The electro-acoustic input transducer may be provided in the in-the-ear unit or may be provided in the BTE unit. The electro-acoustic input transducer is called microphone and converts an acoustic sound signal into an electric audio signal.

In RITE hearing aids, the sound processor is typically arranged in the BTE unit and is connected to the electro-acoustic output transducer (and the electro-acoustic input transducer) by way of electrically conducting wires arranged in a coupling element (connection tube) that mechanically connects the in-the-ear unit to the behind-the-ear unit.

Recently, there was a development to place sensors and additional electronic components in the in-the-ear unit.

However, with adding sensors and/or additional electronic components to the in-the-ear unit, the size of the in-the-ear-unit (the outer appearance thereof) increases, which leads to that a resulting in-the-ear unit cannot anymore be placed in the ear or ear canal of a user or at least placement therein causes discomfort for the user. Furthermore, it also prevents the in-the-ear unit to enter the deep part of the ear canal where posterior auricular arteries or deep auricular arteries are located within the head of the user.

US2014205122AA discloses an example of a hearing aid assembly comprising a first part being a behind-the-ear part and a second part being an In-the-Ear part, the first part comprising a DSP, the second part comprising an electronic-auxiliary-function-unit and a receiver, wherein the electronic-auxiliary-function-unit includes a microcontroller and is arranged for storing an identification string representing the receiver, and wherein the DSP is configured to request the identification string from the microcontroller and adapt audio processing for the receiver based on the received identification string. In US2014205122AA the DSP, the electronic auxiliary function unit are arranged outside the receiver, and the disadvantage with this solution is that the size of the in-the-ear part increases due to the number of components arranged within.

Therefore, there is a need to provide a solution that addresses at least some of the above-mentioned problems. The present disclosure provides at least an alternative to the prior art.

SUMMARY

According to an aspect of the present disclosure, there is provided an in-the-ear hearing aid device. The in-the-ear hearing aid device comprises at least one electro-acoustic transducer. The in-the-ear hearing aid device further comprises at least one sensor and/or at least one active electronic component. The at least one electro-acoustic transducer comprises a capsule enclosing a transducer sound active part and a transducer air volume. Further, the transducer air volume is air volume which is enclosed by said capsule and which is in fluid-connection with said transducer sound active part. Furthermore, at least a portion of said at least one sensor and/or of said at least one active electronic component is provided within said transducer air volume.

According to a further aspect of the present disclosure, there is provided an in-the-ear hearing aid device. The in-the-ear hearing aid device comprises at least one electro-acoustic transducer. The in-the-ear hearing aid device further comprises at least one sensor and/or at least one active electronic component. The at least one electro-acoustic transducer comprises a capsule enclosing a transducer sound active part and a transducer air volume. Further, the transducer air volume is air volume which is enclosed by said capsule and which is in fluid-connection with said transducer sound active part. Furthermore, at least a portion of said at least one sensor and/or of said at least one active electronic component is provided within the capsule and within said transducer air volume.

The advantage of providing or arranging the at least one sensor and/or the at least one active electronic component within the capsule and within said transducer air volume is that the size of the in-the-ear hearing aid device would not increase or increase significantly less when comparing to known prior art where the at least one sensor and/or the at least one active electronic component is placed outside the capsule, i.e. within a housing of the in-the-ear hearing aid device but not within the capsule of the at least one electro-acoustic transducer including a diaphragm The in-the-ear hearing aid device may comprise one or more signal processors or microcontrollers configured to receive physiological information or biometric signals from a body of a user of the in-the-ear-hearing aid device or the electro-acoustic transducer. The one or more signal processors may be configured to process the physiological information or the biometric signal into a processed signal which may be used for monitoring the health of the user, environmental monitors, and for therapy.

Preferably, the transducer air volume may be air volume which is enclosed by said capsule and which is in fluid-connection with said transducer sound active part and with said capsule.

At least part of said capsule may form an exterior housing of said in-the-ear hearing aid device defining an outer contour of said in-the-ear hearing aid device.

The capsule may form a housing of said at least one electro-acoustic transducer.

The capsule may include a receiver outlet of the in-the-ear hearing aid device, wherein a passage through said receiver outlet is in fluid-connection with an outlet opening in said housing of said at least one electro-acoustic transducer, wherein said outlet opening is in fluid-connection with said transducer sound active part.

The capsule may include an elastic dome of the in-the-ear hearing aid device to fit into an ear canal of a user, wherein a passage through said elastic dome is in fluid-connection with said receiver outlet. The elastic dome may be attached to the capsule.

The capsule may include a connection tube of the in-the-ear hearing aid device, wherein a passage through said connection tube is in fluid-connection with an opening in said housing of said at least one electro-acoustic transducer, wherein said opening is in fluid-connection with said transducer sound active part.

The passage through said connection tube may be in fluid-connection with an opening in a housing of a behind-the-ear hearing aid device.

The capsule may include a microphone inlet of the in-the-ear hearing aid device, wherein a passage through said microphone inlet is in fluid-connection with an inlet opening in said housing of said at least one electro-acoustic transducer, wherein said inlet opening is in fluid-connection with said transducer sound active part.

The at least one electro-acoustic transducer may be one of a microphone and a receiver.

The transducer sound active part may comprise at least one of a membrane, a diaphragm, an electromagnetic mechanism, and a sound vibrating unit.

At least a portion of said at least one sensor and at least a portion of said at least one active electronic component may be provided within said transducer air volume, wherein a line of sight between said portion of said at least one sensor and said portion of said at least one active electronic component is shielded by a portion of said electro-acoustic transducer.

At least a portion of a first sensor and at least a portion of a second sensor may be provided within said transducer air volume, wherein a line of sight between said portion of said first sensor and said portion of said second sensor is shielded by a portion of said electro-acoustic transducer or by said portion of said at least one active electronic component.

Furthermore, the shielding may be provided by guiding means, wherein a first guiding mean is configured to guide a biometric signal, i.e. a signal generated by a body of the user in response to a signal generated by said at least one active electronic component, to said sensor A second guiding mean may be configured to guide an emitted signal, such as a light signal, from the at least one active electronic component to the body of the user, e.g. the ear canal of the user. A guiding mean may be an optical fiber or a hollow plastic or metal tube.

The capsule may comprise at least one measurement opening. In such case, the at least one measurement opening may be provided with an electromagnetic filter configured to prevent electromagnetic waves having a frequency lower than a predetermined noise shielding frequency from entering said capsule through said at least one measurement opening.

The electromagnetic filter may comprise at least one of a mesh or an optically transparent material.

The predetermined noise shielding frequency may be anyone of not audible frequencies.

The at least one sensor may comprise at least one of a temperature sensing element, a light sensing element, a sound sensing element, a humidity sensor, a moisture sensing element, a blood oximetry sensor including at least two light emitting elements and a light sensing element, a blood pressure sensor, a blood sugar sensor, a pulse sensor, a hydration sensor, a galvanic skin response electrode, an electroencephalography electrode, and an electrooculography electrode.

The at least one sensor may be a footstep sensor, a heart rate sensor, a pulse sensor, an ECG sensor, a pulse oximeter sensor, or a biological sensor. The biological sensor may include a pulse oximeter and/or temperature sensor, a blood alcohol level sensor, a blood glucose sensor, a bilirubin sensor, a blood pressure sensor, an electroencephalogram sensor, an Adenosine Triphosphate (ATP) sensor, a lactic acid sensor, a hemoglobin sensor, a hematocrit sensor, or other biological sensor. The electro-acoustic transducer may further include a chemical sensor. The electro-acoustic transducer may further include at least one inertial sensor. The inertial sensor may be an accelerometer, a gyrometer, a gyro sensor, a magnetometer or other sensor.

The in-the-ear hearing aid or the electro-acoustic transducer may comprise at least one footstep sensor configured to sense footsteps of the user wearing the electro-acoustic transducer or the in-the-ear hearing aid, and to produce a footstep signal in response to the sensed footsteps. One or more signal processors comprised by the in-the-ear hearing aid and/or the electro-acoustic transducer may be configured to receive physiological signal and footstep signal from one or more sensors provided within said transducer air volume. The signal processors may be configured to process the physiological signal to produce at least one processed signal containing cleaner physiological information from the person using the footstep signal. The signal processors may be configured to process the footstep signal to produce at least one processed footstep signal containing cleaner information about footsteps of the person. In one example, the physiological information may be similar to a biometric signal.

The in-the-ear hearing aid or the electro-acoustic transducer may be used within the field of personal health and environmental monitors, for example, for gauging overall health and metabolism during exercise, athletic training, dieting, daily life activities, sickness, and physical therapy.

Detection or monitoring of neuropsychiatric disorders, namely depression and anxiety disorders, such as PTSD, is accomplished by the in-the-ear hearing aid device or the electro-acoustic transducer. In this example, a group of sensors is provided within said transducer air volume, where the group of sensors may comprise a blood pressure sensor and a heart rate sensor. A signal processor configured to receive the physiological information (or biometric signals) from the blood pressure sensor and the heart rate sensor may detect or monitor an increase in heart rate and blood pressure of the user wearing the in-the-ear hearing aid device or the electro-acoustic transducer. A first increase rate of the increase in the heart rate may be above a first threshold, and a second increase rate of the increase in the blood pressure may be above a second threshold, and in this situation, the user may have Post-Traumatic Stress Disorder (PTSD). The detection or monitoring of PTSD may be further improved by connecting the in-the-ear hearing aid device or the electro-acoustic transducer to an external device wirelessly or wired, where the external device provides information on what the user is seeing to the signal processor. The signal processor may be placed in the in-the-ear hearing aid device or in the electro-acoustic transducer, or the signal processor may be configured to transmit the processed physiological information, i.e. the blood pressure and heart rate, to another signal processor in the external device. The another signal processor or the signal processor may be configured to combine the measure of the blood pressure and the heart rate with the information on what the user is seeing for detecting PTSD. The information on what the user is seeing may be generated by a camera, a virtual reality glass, a monitor or any kind of a device configured to provide an image containing the information on what the user is seeing.

The information on what the user is seeing may be replaced or combined with what the user is listening too. The user may receive an acoustical sound from the electro-acoustic transducer, from the external device or from another electro-acoustic transducer within a hearing aid device. Thereby, the detection or monitoring of PTSD may be further improved by the signal processor configured to combine the measure of the blood pressure and the heart rate with the information on what the user is listening too.

A portable monitoring device comprising a hearing aid device having a housing, at least one microphone for receiving ambient sound, an audio signal processor configured for processing a signal from the microphone, and the electro-acoustic transducer, said portable monitoring device further comprising an EEG monitoring system for monitoring EEG signals of a person using the hearing aid, and wherein said EEG monitoring system may be partly arranged in said transducer air volume, said EEG monitoring system comprising
 said at least one sensor configured for measuring one or more EEG signals from the person carrying the EEG monitor, said at least one sensor may be multiple electrodes, being arranged partly or completely on the outer surface of the capsule of the electro-acoustic transducer or an outer wall of the capsule comprises partly or completely said at least one sensor, and
 an EEG signal processing mean for analysing the one or more EEG signals, said audio signal processing mean being adapted for, based on the EEG signal, identifying or predicting specific biological incidences, in said person, said audio signal processing mean comprising decision means for deciding, based on said analysed EEG signal, when an alarm or information must be provided to said person, wherein said acoustic signal processing means being arranged in said housing: and the housing comprises means for providing said alarm or information through said output transducer or via a wireless link to an external device.

For many hearing impaired persons using a hearing aid it may be difficult to handle this small high tech product. This may especially be a problem to elderly persons. If these persons are also equipped with an EEG monitoring system, which also needs correct handling in order to function properly, the risk of incorrect handling of at least one of these two devices will most likely increase significantly. This imposes a risk of missing an alarm of an upcoming biological incidence, such as hypoglycemia, or of not having the possible optimal hearing.

Therefore, it will often be a problem to equip elderly persons with both a hearing aid and an EEG monitoring system, both being equipment to which they must pay attention and handle in specific different ways in order to obtain the benefits of these devices. Also, more devices arranged on the body of a person increase the risk of overlooking one. Further, a hearing aid user often needs two hearing aids.

The above problem has been solved by arranging the EEG monitoring system in said transducer air volume of the electro-acoustic transducer.

Furthermore, the advantage of arranging the EEG monitoring system in said transducer air volume is that the size of the electro-acoustic transducer does not increase because the EEG monitoring system is utilizing air volume which is not occupied by other electronics components.

Thereby, if the electro-acoustic transducer is placed in the in-the-ear hearing aid device, the user will not feel more uncomfortable when wearing the in-the-ear hearing aid device when comparing to an in-the-ear hearing aid device with a regular electro-acoustic transducer without the EEG monitoring system.

The portable monitoring device comprising adjustment means for adjusting the sound level of a sound message according to the acoustic background noise level in order to make the sound message clearly discernible over the background noise.

The external device may be a smartphone configured to display the alarm or play the sound message. This is specially an advantage when a parent or an adult to the user of the portable monitoring device wants to receive the alarm or the information. Thereby, it is possible for the parent or the adult to monitor the health of the user distantly.

Said biological incidence may be hypoglycemia.

The EEG monitoring system may be adapted for a wireless connection to an EEG processing unit comprising the EEG signal processing means and being part of the EEG monitoring system.

The EEG monitoring system may comprise an electronic module, and said electronic module may be connected with the at least one sensor, and further being connected with communication means for transmitting the EEG signal to the EEG processing unit.

The at least one active electronic component may comprise at least one of a light emitting diode, a pre-processor, a digital sound processor, an amplifier, a pre-amplifier, an AD-converter, a DA-converter, a sensor processing circuitry, a sensor fusion circuitry, a digital speaker communication bus, a bus controller circuitry, a memory, and a microcontroller.

The transducer air volume may be separated into a first transducer air volume and a second transducer air volume not in fluid-connection with said first transducer air volume.

In such case, the first transducer air volume is larger in volume than said second transducer air volume. Further, in such case, the portion of said at least one sensor or of said at least one active electronic component may be provided within said first transducer air volume. The first transducer air volume is in fluid-connection to a volume outside the housing of said at least one electro-acoustic transducer via the outlet opening an/or via the inlet opening. Thereby, the volume of the first transducer air volume is actual a sum of the first transducer air volume within said housing and the volume outside said housing. Therefore, by placing at least a portion of said at least one sensor and/or of said at least one active electronic component in the first transducer air volume will not result in an increase of the volume of the housing because the acoustical performance of said at least one active electronic component is not affected by the occupation of volume by the at least a portion of said at least one sensor and/or of said at least one active electronic component.

At least a portion of at least another sensor and/or of at least another active electronic component may be provided within said second transducer air volume. Said second transducer air volume is smaller than said first transducer air volume, however, by placing a limited number of at least the portion of at least another sensor and/or of at least another active electronic component within said second transducer air volume has a slightly impact on the acoustical performance of the at least one electro-acoustic transducer. The impact may not be noticeable for the user of the transducer.

Alternatively, the portion of said at least one sensor or of said at least one active electronic component may be provided within said second transducer air volume.

According to a further aspect of the present disclosure, there is provided a hearing aid. The hearing aid comprises any form of the above discussed in-the-ear hearing aid device. The hearing aid further comprises a behind-the-ear hearing aid device. The hearing aid further comprises a coupling element configured to mechanically and/or electrically connect said in-the-ear hearing aid device and said behind-the-ear hearing aid device.

According to a further aspect of the present disclosure, there is provided an electro-acoustic transducer. The electro-acoustic transducer comprises at least one sensor or at least one active electronic component. The electro-acoustic transducer further comprises a capsule enclosing a transducer sound active part and a transducer air volume. The transducer air volume is air volume which is enclosed by said capsule and which is in fluid-connection with said transducer sound active part. At least a portion of said at least one sensor or of said at least one active electronic component is provided within said transducer air volume.

By occupying part of the air volume within the electro-acoustic transducer with at least the portion of said at least one sensor and/or of said at least one active electronic component then the size of the electro-acoustic transducer does not increase, and thereby, it is possible to create an intelligent electro-acoustic transducer without the need of increasing the size of the electro-acoustic transducer. The electro-acoustic transducer is therefore suitable for being placed in small space area, such as in an ear canal, a smartphone, a smartwatch, a hearing device, such as a headphone, a headset, or any kind of electronic device with size restriction.

Preferably, the transducer air volume may be air volume which is enclosed by said capsule and which is in fluid-connection with said transducer sound active part and with said capsule.

The at least one electro-acoustic transducer may be one of a microphone and a receiver.

The transducer sound active part may comprise at least one of a membrane, a diaphragm, an electromagnetic mechanism, and a sound vibrating unit.

At least a portion of said at least one sensor and at least a portion of said at least one active electronic component may be provided within said transducer air volume, wherein a line of sight between said portion of said at least one sensor and said portion of said at least one active electronic component is shielded by a portion of said electro-acoustic transducer or by said portion of said at least one active electronic component.

Furthermore, the shielding may be provided by guiding means, wherein a first guiding mean is configured to guide a biometric signal, i.e. a signal generate by a body of the user in response to a signal generated by said at least one active electronic component, to said sensor A second guiding mean may be configured to guide an emitted signal, such as a light signal, from the at least one active electronic component to the body of the user, e.g. the ear canal of the user. A guiding mean may be an optical fiber or a hollow plastic or metal tube.

At least a portion of a first sensor and at least a portion of a second sensor may be provided within said transducer air volume, wherein a line of sight between said portion of said first sensor and said portion of said second sensor is shielded by a portion of said electro-acoustic transducer.

The capsule may comprise at least one measurement opening, and said at least one measurement opening is provided with an electromagnetic filter configured to prevent electromagnetic waves having a frequency lower than a predetermined noise shielding frequency from entering said capsule through said at least one measurement opening.

The advantage of having an electromagnetic filter, such as an EMI mesh, is that light is able to pass through the mesh while filtering EM noise. Thereby, it is possible to place light emitting sensors within the capsule without inducing EM noise to the electro-acoustic transducer.

The at least one sensor may comprise at least one of a temperature sensing element, a light sensing element, a sound sensing element, a moisture sensing element, a blood oximetry sensor including at least two light emitting elements and a light sensing element, a blood pressure sensor, a blood glucose sensor, an insulin sensor, a pulse sensor, a hydration sensor, a galvanic skin response electrode, an electroencephalography electrode, and an electrooculography electrode. Furthermore, the at least one sensor may be one or more biosensors configured for measure and quantify ketone levels of the blood of a person.

The at least one active electronic component may comprise at least one of a light emitting diode, a pre-processor, a digital sound processor, an amplifier, a pre-amplifier, an AD-converter, a DA-converter, a sensor processing circuitry, a sensor fusion circuitry, a digital speaker communication bus, a bus controller circuitry, a memory, and a microcontroller.

The transducer air volume may be separated into a first transducer air volume and a second transducer air volume not in fluid-connection with said first transducer air volume. Then, the first transducer air volume is larger in volume than said second transducer air volume, and the portion of said at least one sensor or of said at least one active electronic component is provided within said first transducer air volume. The first transducer air volume is in fluid-connection to a volume outside the capsule of said at least one electro-acoustic transducer via the outlet opening. Thereby, the volume of the first transducer air volume is actual a sum of the first transducer air volume within said capsule and the volume outside said capsule. Therefore, by placing at least a portion of said at least one sensor and/or of said at least one active electronic component in the first transducer air volume will not result in an increase of the volume of the capsule because the acoustical performance of said at least one active electronic component is not affected by the occupation of volume by the at least a portion of said at least one sensor and/or of said at least one active electronic component.

Said transducer air volume is separated into a first transducer air volume and a second transducer air volume by said transducer sound active part. Furthermore, a first group of one or more sensors may be placed within the first transducer air volume and a second group of multiple sensors may be placed within the second transducer air volume or vice versa, and wherein the first group and the second group are arranged such that the sensors of both groups are arranged in a trigonometric structure configured for generating a biometric signal, e.g. including foot step detection.

In the example where the electro-acoustic transducer is positioned in the ear canal, the position of said at least one sensor and/or of said at least one active electronic component is relevant in order for obtaining an optimal detection of physiological information, i.e. biometric signals, from the body of the user with, i.e. the signal-to-noise ratio of the biometric signal or the physiological information is sufficient to obtain reliable physiological measures, such as heart rate, pulse, blood glucose, insulin, blood pressure, EEG, oxygen saturation, PTSD measure and/or body temperature etc.

The capsule has a first end and a second end, wherein the outlet opening or the inlet opening is positioned closest to the first end. Said at least one sensor and/or said at least one active electronic component may be arranged closest to the first end. Said at least one sensor and/or said at least one active electronic component arranged closest to the first end or arranged at the first end is positioned deep into the ear canal of the user. The obtained advantage is a better signal-to-noise ratio of the physiological information or biometric signal. In an optical system, where the at least one sensor is a photodetector and the at least one active electronic component is one or more light emitting diodes, the improved signal-to-noise ratio is obtained due to less stray light from the surroundings interfering with the measurement of the physiological information or the biometric signal.

The capsule may have at least one sensor and/or the at least one active electronic component placed partly within the transducer air volume and on an inner surface of a wall of the capsule, or on an outer surface of a wall of the capsule where the wiring to the at least one sensor and/or the at least one active electronic component enters the transducer air volume. Both the inner surface of the wall and the outer surface of the wall may have a corner and an edge. Additionally, the at least one sensor and/or the at least one active electronic component may be arranged at or near the corner and/or at or near the edge. Thereby, a distance between the skin of the ear canal and the at least one sensor and/or the at least one active electronic component is minimized when the electro-acoustic transducer is placed within the ear canal, e.g. when the electro-acoustic transducer is comprised by an in-the-ear hearing aid device. The advantage of the minimized distance is that the quality of the physiological information or the biometric signal is improved.

In another example, the inner surface of the wall of the capsule or the outer surface of the wall of the capsule may have a centre axis, wherein the at least one sensor and/or the at least one active electronic component may be arranged around the centre axis. The advantage is that the fabrication of the electro-acoustic transducer becomes simpler.

In the vicinity of the ear canal several main arteries are located within the head of a person, the so-called Superficial temporal artery, Anterior auricular artery, Maxillary artery, Posterior auricular artery, Internal carotid artery and External carotid artery. The ear canal has a longitudinal axis extending from the opening of the ear canal towards the eardrum of the ear canal. The ear canal has a transverse axis extending orthogonal or partially orthogonal to the longitudinal axis. Where the longitudinal axis and the transverse axis intersects each other within the ear canal defines a centre point in the ear canal. Each main artery is positioned relative to the ear canal as following;

External carotid artery or Internal carotid artery is positioned below the ear canal and within a line of sight angle defined from the centre point in the ear canal directed along the transverse axis, and where the line of sight angle is between 45° and 120°, between 90° and 110°, and between 35° and 160°, Internal carotid artery is partly positioned below and above the ear canal and within a line of sight angle defined from the centre point in the ear canal directed along the transverse axis or the longitudinal axis inwards the ear canal, and where the line of sight angle is between 45° and 120°, between 90° and 110°, and between 35° and 160°, Posterior auricular artery is positioned below the ear canal and within a line of angle defined from the centre point in the ear canal directed along the transverse axis, and where the line of sight angle is between 10° and 45°, between 5° and 25°, and between 90° and 110°, Superficial temporal artery is positioned above the ear canal and within a line of sight angle defined from the centre point in the ear canal directed along the transverse axis and in a forward direction towards a face of the user, and where the line of sight angle is between 10° and 45°, between 5° and 25°, and between 90° and 110°, and Anterior auricular artery and Maxillary artery, are positioned within a line of sight angle defined from the centre point in the ear canal directed along the transverse axis and in a forward direction towards a face of the user, and where the line of sight angle is between 10° and 45°, between 5° and 25°, and between 90° and 110°.

The capsule enclosing the transducer air volume may comprise a longitudinal axis and a transverse axis, wherein the longitudinal axis of the capsule and the longitudinal axis of the ear canal is extending in parallel or partially parallel, and wherein the transverse axis of the capsule and the transverse axis of the ear canal is extending in parallel or partially parallel.

The at least one sensor may have a first line of sight and/or the at least one active electronic component may have a second line of sight. The at least one sensor and/or the at least one active electronic component may be arranged within the transducer air volume such that the first line of sight and/or the second line of sight is directed towards one or more of the main arteries.

The at least one sensor may be arranged such that the first line of sight is directed within the line of sight angle towards one or more of the main arteries.

In one example, the at least one active electronic component may be arranged such that the second line of sight is directed within the line of sight angle towards one or more of the main arteries.

The inlet opening or the outlet opening may have a mechanical interface configured to receive an earpiece. Normally, the mechanical interface is symmetric in all directions, i.e. a user of the in-the-ear hearing aid device has the possibility of mounting the earpiece to the mechanical interface such that the at least one sensor and/or the at least one active electronic component is positioned wrongly within the ear canal of the user.

The mechanical interface may have one or two symmetrical axes, wherein the number of possible angles for mounting the earpiece to the mechanical interface has reduced to one or two ways, respectively. Thereby, the usability has improved because the possibility of placing the earpiece such that the at least one sensor and/or the at least one active electronic component is arranged wrongly within the ear canal has reduced significantly. Where only one symmetrical axis, then it is not possible for the user to mount the earpiece wrongly to the mechanical interface.

The capsule may have both the outlet opening and the inlet opening, where the electro-acoustic transducer may be a microphone and a receiver.

The electro-acoustic transducer may comprise an optical system including the at least one sensor which may be a photodetector, and the at least one active electronic component which may be one or more light emitting diodes. Several problems may occur in the optical system, such as light from outside may ruin the measurement of the at least one sensor, light from the light emitting diode(s) may be seen from outside when the user is in darkness, reflections from the skin surface of the ear canal, and light from outside exiting through the skin of the ear canal and in to the at least one sensor. To solve one or more of the problems, the capsule may comprise an outer guiding mean for both the at least one sensor and the at least one active electronic component, wherein the outer guiding mean may be mounted on to an outer surface of a wall of the capsule or implemented into the earpiece provided on the mechanical interface. The outer guiding mean may comprise a light guiding material. A different solution to one or more of the mentioned problems could be to provide an earpiece to the mechanical interface or the capsule, where the shape of the earpiece is configured to prevent light from outside to interfere with the at least one sensor measurement. Another earpiece may be provided to the capsule, wherein the at least one sensor and/or the at least one active electronic component may be arranged between the another earpiece and the earpiece.

The sensors may further be able to measure or monitor changes in the user-behaviour of the hearing aid including the sensors. Information collected by the sensors in the in-the-ear hearing aid can be transferred into predictive algorithms included in a processor of the hearing aid, and allow to provide better service to the end-user with, for example, better remote fitting services

BRIEF DESCRIPTION OF DRAWINGS

The objects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each object may each be combined with any or all features of the other objects. These and other objects, features and/or technical effect will be apparent from and elucidated with reference to the illustrations described hereinafter in which:

FIG. 27 illustrates a receiver-in-the-ear hearing aid in a communication scenario according to an embodiment of the disclosure;

FIG. 29 illustrates different positions of the at least one sensor and/or the at one active electronic component within the transducer air volume;

FIG. 30 illustrates different positions of the at least one sensor and/or the at one active electronic component within the transducer air volume;

DETAILED DESCRIPTION

Figure 1:
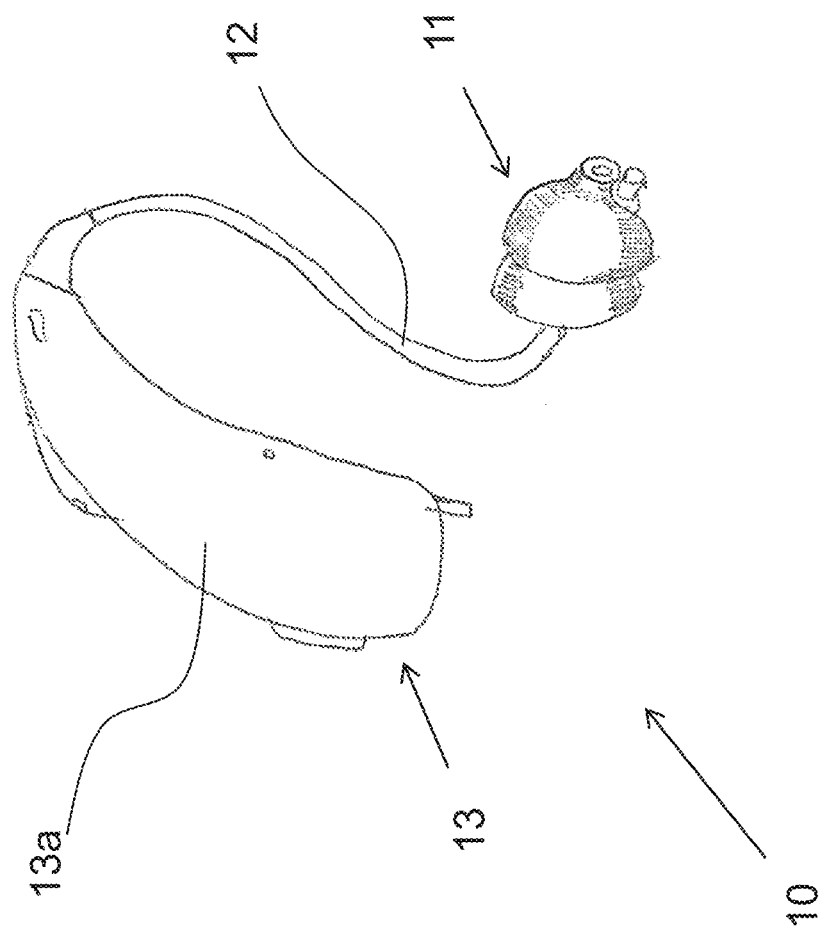
FIG. 1 illustrates a receiver-in-the-ear hearing aid according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device or a hearing aid device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing aid device is adapted to be worn in any known way. This may include i) arranging a unit of the hearing aid device behind the ear with a tube leading air-borne acoustic signals into the ear canal or with a receiver/loudspeaker arranged close to or in the ear canal such as in a Behind-the-Ear type hearing aid, and/or ii) arranging the hearing aid device entirely or partly in the pinna and/or in the ear canal of the user such as in a In-the-Ear type hearing aid or In-the-Canal/Completely-in-Canal type hearing aid, or iii) arranging a unit of the hearing aid device attached to a fixture implanted into the skull bone such as in Bone Anchored Hearing Aid or Cochlear Implant, or iv) arranging a unit of the hearing aid device as an entirely or partly implanted unit such as in Bone Anchored Hearing Aid or Cochlear Implant.

A "hearing system" refers to a system comprising one or two hearing aid devices, and a "binaural hearing system" refers to a system comprising two hearing aid devices where the devices are adapted to cooperatively provide audible signals to both of the user's ears. The hearing system or binaural hearing system may further include auxiliary device(s) that communicates with at least one hearing aid device, the auxiliary device affecting the operation of the hearing aid devices and/or benefiting from the functioning of the hearing aid devices. A wired or wireless communication link between the at least one hearing aid device and the auxiliary device is established that allows for exchanging information (e.g. control and status signals, possibly audio signals) between the at least one hearing aid device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid device. The remote control is adapted to control functionality and operation of the at least one hearing aid devices. The function of the remote control may be implemented in a Smartphone or other electronic device, the Smartphone/electronic device possibly running an application that controls functionality of the at least one hearing aid device.

In general, a hearing aid device includes i) an input unit such as a microphone for receiving an acoustic signal from a user's surroundings and providing a corresponding input audio signal, and/or ii) a receiving unit for electronically receiving an input audio signal. The hearing aid device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing aid devices, the output unit may include one or more output electrodes for providing the electric signals such as in a Cochlear Implant.

The electro-acoustic output transducer may comprise a driver, e.g. a diaphragm or a moving magnetic armature, that moves according to the electric audio signal driving the electro-acoustic output transducer to thus generate air movements that can be perceived as acoustic sound. In the present document, the driver is also named transducer sound active part. The driver of the electro-acoustic output transducer is arranged in an air-filled volume. The air filled volume may include a volume on both sides of e.g. the diaphragm of a driver of the output transducer. At least one part of the air-filled volume the driver acts on is fluid connected to a sound outlet of the in-the-ear hearing aid. The sound outlet is defined by an opening of the exterior housing surrounding the electro-acoustic output transducer.

Figure 5:
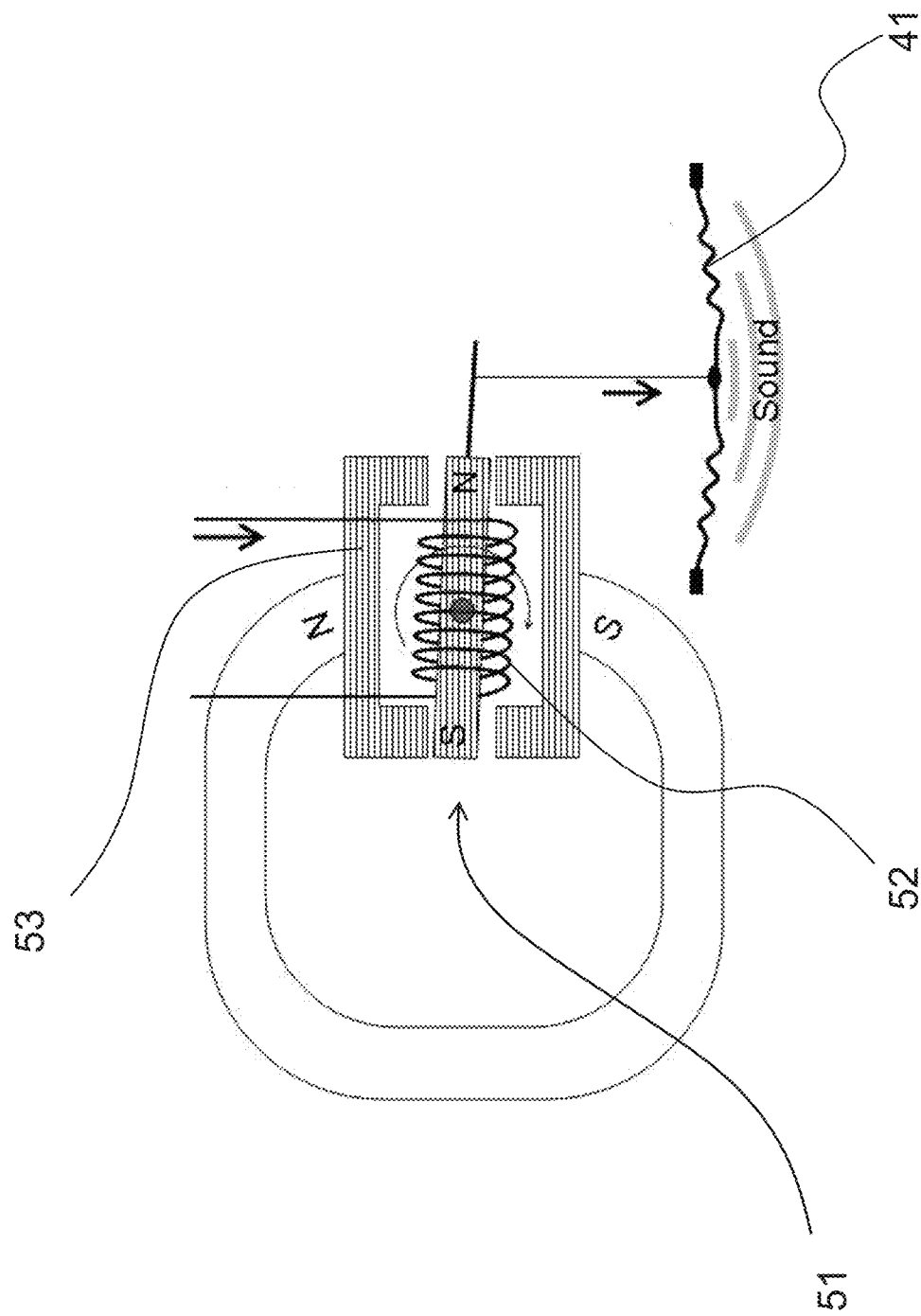
FIG. 5 illustrates a transducer sound active part according to an embodiment of the disclosure.

FIG. 5 illustrates a transducer sound active part according to an embodiment of the disclosure.

The electro-acoustic output transducer schematically illustrated in this Figure comprises a driver that is configured to drive the air next to the driver to thus create sound waves. The driver may comprise a diaphragm 41 that is driven by an electromagnetic actuator 51 comprising an electric coil 52 and a magnet 53. The electric coil 52 and the magnet 53 are configured to allow relative movement between each other in response to an electric signal that causes a magnetic flux in the coil 52. Thus, the electromagnetic actuator 51 can convert an electric audio signal into mechanic vibrations that can generate acoustic sound waves. Accordingly, an electric audio signal can be converted into an acoustic sound signal by means of the electromechanical actuator 51 and the diaphragm 41. One known type of an electro-acoustic output transducer is a balanced-armature speaker. Next to the diaphragm 41 or other moving part of the electro-acoustic output transducer an air-filled acoustic volume is provided that contains the air that is driven by the driver when operated. The air-filled acoustic volume may be fluid connected to a sound outlet of an exterior housing of the in-the-ear hearing aid device.

A comparable structure may be present in an electro-acoustic input transducer (i.e. a microphone), where the parts receiving air movements that can be perceived as acoustic sound and converting them into electric audio signals correspond to the transducer sound active part of the electro-acoustic input transducer.

Typically, the electro-acoustic output transducer is arranged in a transducer capsule encapsulating the electro-acoustic output transducer and defining the air-filled volume the driver acts on.

Now referring to FIG. 1 which illustrates a receiver-in-the-ear hearing aid device according to an embodiment of the disclosure.

According to FIG. 1, the receiver-in-the-ear hearing aid 10 comprises an in-the-ear hearing aid device 11, a connection tube 12, and a behind-the-ear hearing aid device 13. The behind-the-ear hearing aid device 13 is enclosed by a housing 13a of the behind-the-ear hearing aid device 13.

As mentioned above, recently, there was a development to place sensors and additional electronic components in the in-the-ear unit, in particular, in the ear canal of a user wearing the respective hearing aids. However, while the addition of sensors or other electronic components demand space, the ear canals of the users still have the same sizes. Hence, the sensors/components are to be accommodated in the in-the-ear hearing aid device of roughly the same size as earlier devices.

Figure 2:
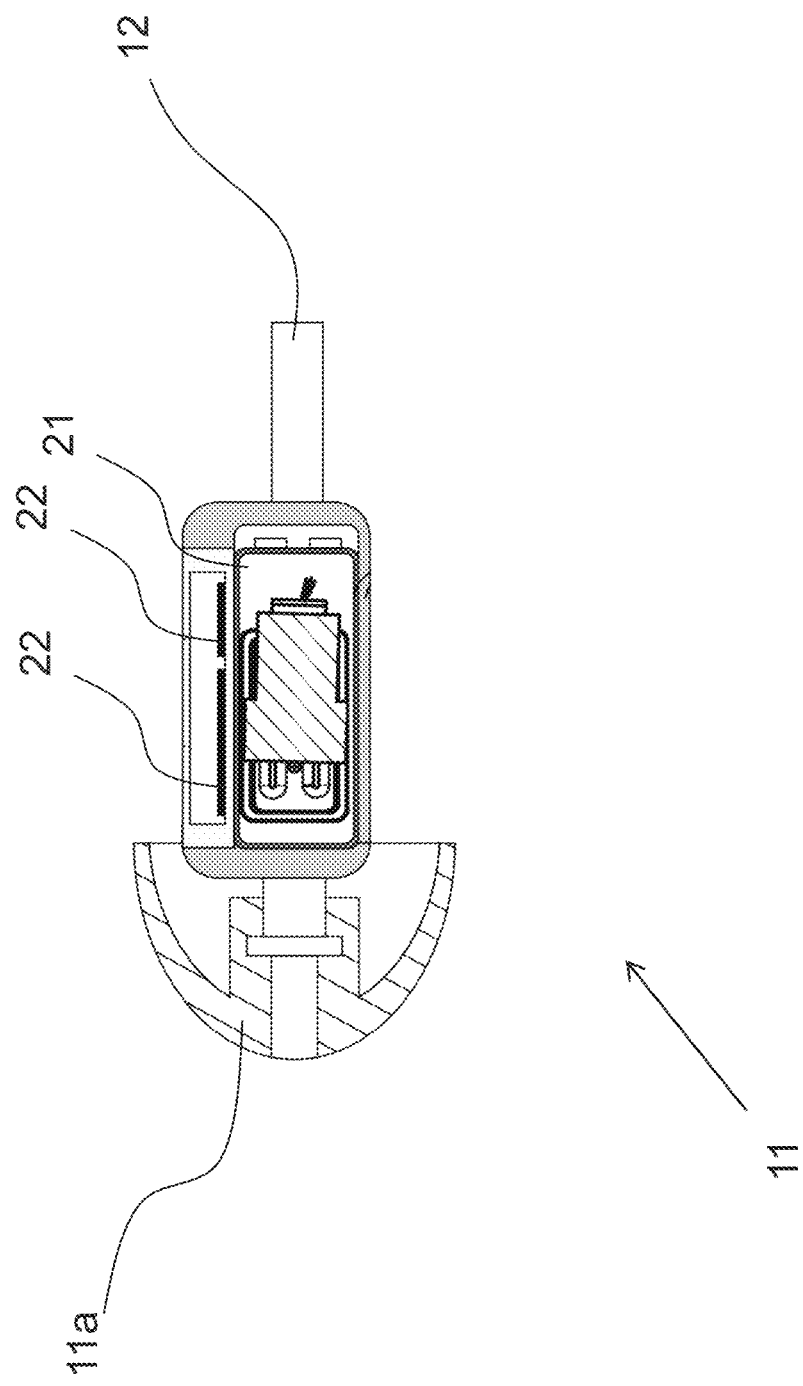
FIG. 2 illustrates an in-the-ear part (unit) of a receiver-in-the-ear hearing aid.

Now referring to FIG. 2 which illustrates an in-the-ear part (unit) of a receiver-in-the-ear hearing aid.

In particular, in FIG. 2 an in-the-ear hearing aid device 11 is illustrated including a (an elastic) dome 11a to fit into an ear canal of a user. The in-the-ear hearing aid device 11 further comprises a transducer 21 as well as sensors/components 22.

An option of implementing sensors/components 22 in the in-the-ear hearing aid device is filling those standard sensors into an in-the-ear hearing aid device housing (speaker unit housing) while using the box shaped acoustic transducers/speakers 21. Here, both the sensor(s) and the acoustic transducers has an air volume in/around each of them.

Figure 3:
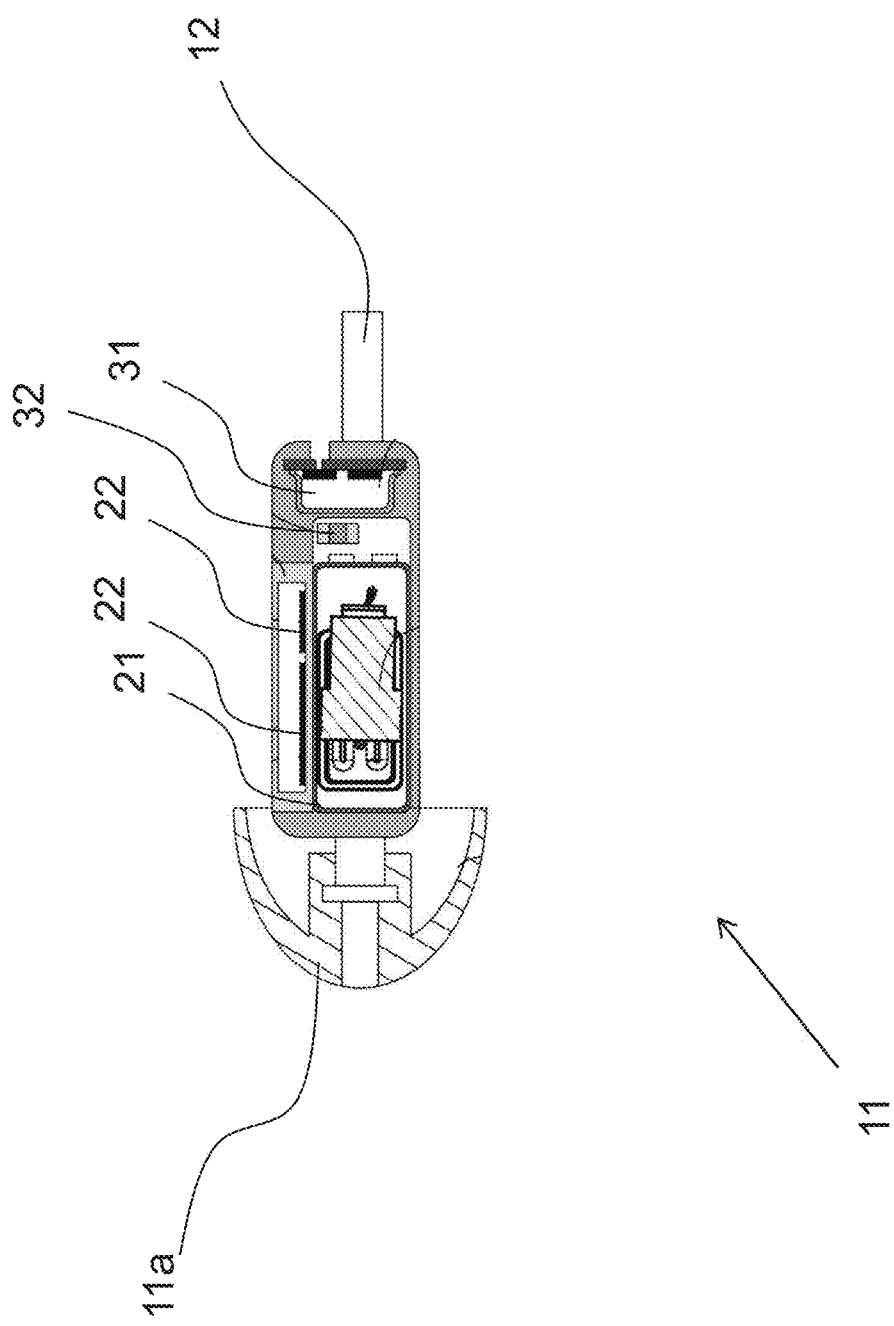
FIG. 3 illustrates an in-the-ear part (unit) of a receiver-in-the-ear hearing aid.

Now referring to FIG. 3 which illustrates an in-the-ear part (unit) of a receiver-in-the-ear hearing aid.

In particular, FIG. 3 illustrates an in-the-ear hearing aid device 11 as shown in FIG. 2, where additionally a microphone (input transducer) 31 is arranged as well as further sensors/components 32.

Figure 4:
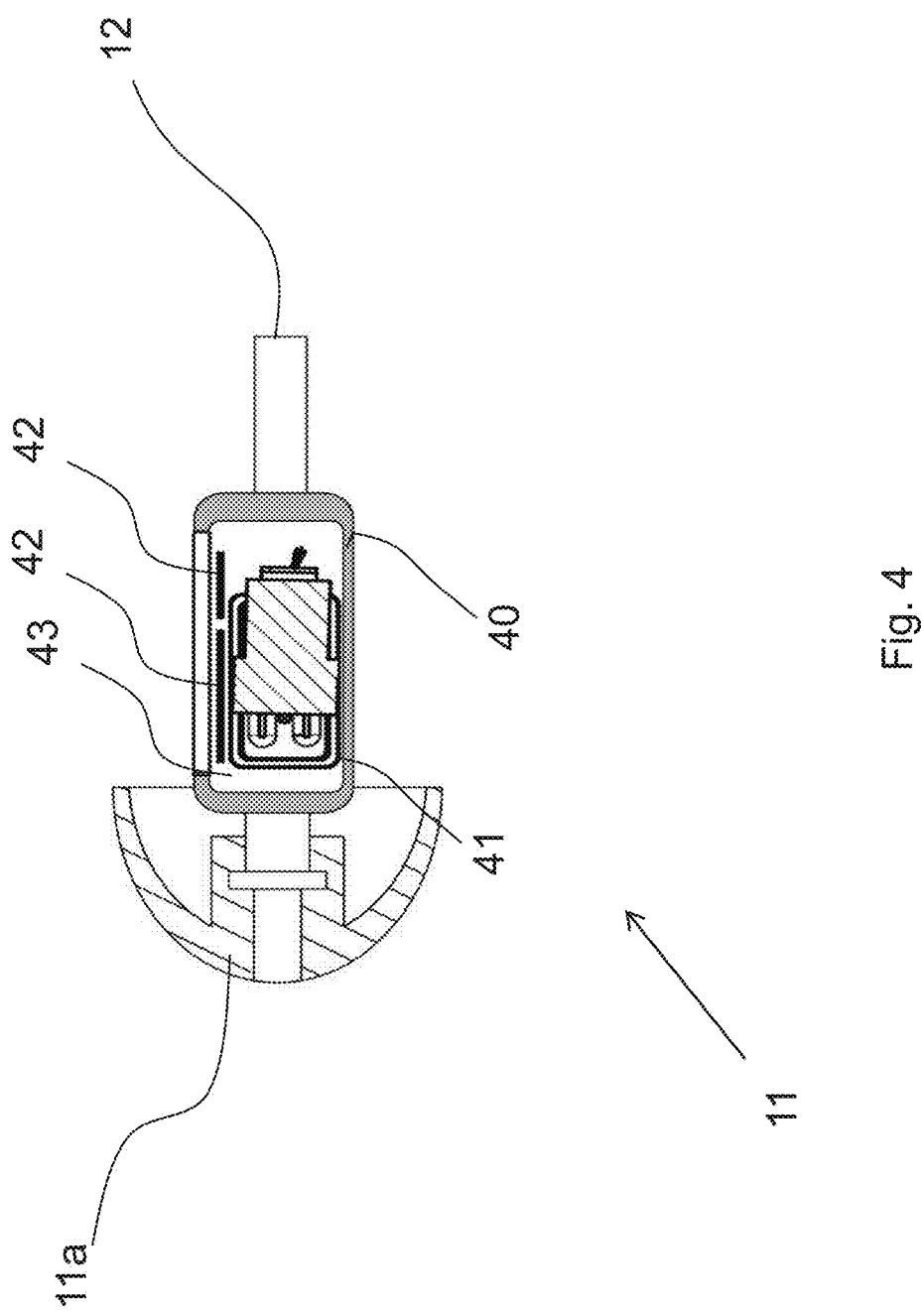
FIG. 4 illustrates an in-the-ear part (unit) of a receiver-in-the-ear hearing aid according to an embodiment of the disclosure.

Now referring to FIG. 4 which illustrates an in-the-ear part (unit) of a receiver-in-the-ear hearing aid according to an embodiment of the disclosure.

As can be seen in FIG. 4, the sensors/components 42 are placed within a transducer air volume which is enclosed by capsule 40 and is in fluid connection with a transducer sound active part 41.

In other words, the sensors/components are integrated in the acoustic volumes of the acoustic transducers.

In this way, the empty air volumes around the transducers can be utilized (at least) twice. Only the actual volume of the solid material in the sensors needs to be added to the acoustic volume. Thereby, clearance for tolerances, distance for optical focus, cavities for wires can be reduced significantly, making a sensor enabled speaker unit (in-the-ear hearing aid device 11) close to the same size as the normal speaker unit.

In view of a considerable air volume typically held by electro-acoustic transducers, an effect of the at least one sensor on the acoustic characteristics of the transducer is not noticeable to the user.

The integration of the "naked" acoustic transducer mechanisms may be accompanied with more details in the speaker unit housing corresponding to the capsule 40 of the in-the-ear hearing aid device 11.

In so doing, the speaker unit (in-the-ear hearing aid device 11) housing does not have double wall thickness but instead may consist of only the capsule 40 of the in-the-ear hearing aid device 11.

With speaker and microphone acoustic volumes integrated in housing/capsule, an improved ear-shaped speaker unit (in-the-ear hearing aid device 11) can be made with the same (or improved) performance.

Namely, when omitting standard housings of microphones and instead embedding the "interior" of the microphones respectively into the capsule of the in-the-ear hearing aid device 11, for example corners normally protruding can be avoided, and potentially even larger acoustic volumes can be provided for the microphones while the outer shape of the in-the-ear hearing aid device 11 (the capsule 40 thereof) can still be improved to the needs of an ear canal.

At least a portion of the electro-acoustic transducer may protrude into the elastic dome 11a. According to a specific embodiment of the present disclosure, the electro-acoustic transducer may be enclosed by the elastic dome 11a.

The capsule 40 with integrated acoustic transducer chambers and sensor/component chambers can be made in injection molded plastic or it can be made (even thinner and thereby smaller) out of metal.

The metal may be coated to prevent ESD problems.

The metal may be e.g. CNC milled, deep drawn sheet metal, MIM molded or die cast.

The metal may be e.g. stainless steel, aluminum or titanium, but is not limited to such material.

Thus, the in-the-ear hearing aid device 11 (the acoustic transducer(s) thereof) can be integrated in combination with (other) sensors. Any sensor could be integrated (hydration, blood pressure, temperature, galvanic skin resistance, electroencephalography (EEG), etc., each considering the respective needs.

The sensor 42 arranged within the transducer air volume is preferably a temperature sensor.

Namely, many body conditions and diseases affect the body temperature throughout a certain period. Normal temperature measurements are snapshots in time of the temperature, e.g. in the morning or in the evening, while in particular a permanent temperature measurement can reveal a temperature development and thus allows for example the distinction of sudden and continuous temperature changes.

By constantly monitoring the body temperature, any uncommon body conditions can be seen immediately. Further, for example hypothermia during outdoor activities in the wintertime or hyperthermia during physical activities in the summer time can be detected.

Things like blood sugar also affects the temperature. For elderly people, temperature might be particularly relevant to monitor often. Temperature is as well a valuable parameter to know in common health monitoring.

The ear canals are a good place for constantly measuring the temperature. Since hearing aids are constantly on the ears, often used by elderly people, while health monitoring gives advantages in relation to immediate reaction to health worsening, ears are a preferable place for measuring temperature.

It is preferred to have the thermistor near the front of the electro-acoustic transducer (innermost in the ear canal) since the temperature at this point is closest to the body temperature (especially when wearing a closed earpiece).

By having a thermometer on the inner side of the elastic dome 11a of the in-the-ear hearing aid device 11, the body temperature can be monitored very accurate.

In the example where the thermometer is arranged on the inner side of the elastic dome 11a, the thermometer is connected to a signal processor arranged within the transducer air volume 43. The connection may be between a first contact plate mounted on the elastic dome or on the thermometer and a second contact plate mounted on the capsule and wherein an electrical connection is between the second contact plate and the signal processor. The first contact plate and the second contact plate may be replaced with a galvanic coupling. The first contact plate and the second plate may touch each other.

Thus, placing a temperature sensor in an in-the-ear hearing aid is advantageous, since the ear is a preferably place to monitor temperature during a full day, the temperature is a good vital sign, the temperature drops a bit just before you get sick, and such measured temperature may provide a sign of metabolism, which might influence doses of medication on a current day.

In general, the temperature sensor provided within the in-the-ear hearing aid may be used to sense body temperature, for fitness purposes, for providing a temperature monitoring visual (e.g. for relatives, medical professionals), for health research, for health monitoring in case of chronic decease, for sensing if hearing instruments is on ear/or off ear, for wear monitoring, i.e. to test how long time the instruments have been on the ear each day, for auto off/ power safe control (e.g. turn off if temperature decreases by a certain amount after instrument have been above 36° C.), for recharge control (e.g. sense overheating during recharging which is most relevant for IIC's), for general testing if the device is overheating.

In addition, information on the temperature (history) may also be user to confirm guarantee cases e.g. by checking whether the device has been stored under a too hot condition.

As a temperature sensor, a thermistor may be utilized, which is a resistor having a known temperature behavior. A prominent of such thermistor is known as PT1000.

A thermistor is a good way to measure the temperature in the ear, since they can be small, accurate, gives a simple output signal and uses very low power.

Further, temperature sensors integrated in integrated circuits may be utilized.

Further, temperature transistors (e.g. by evaluating a basis-emitter voltage thereof) may be used as such temperature sensor.

Finally, also temperature diodes may be used as a temperature sensor to be arranged within the transducer air volume according to embodiments of the disclosure.

Infrared temperature measuring devices can also be utilized, but these use more power, give a more complicated signal and are significantly larger, thus raising serious challenges with having it constantly in the ear at the same time as having a speaker unit.

However, although the sensor 42 arranged within the transducer air volume is preferably a temperature sensor, sensors in relation to determination of pulse, blood sugar, blood pressure, electrooculography, oxygen saturation are preferable as well.

Subsequently, several options for placement of sensors or other electronic components are introduced, each providing specific advantages corresponding to specific needs of respective sensors/components.

Figure 6:
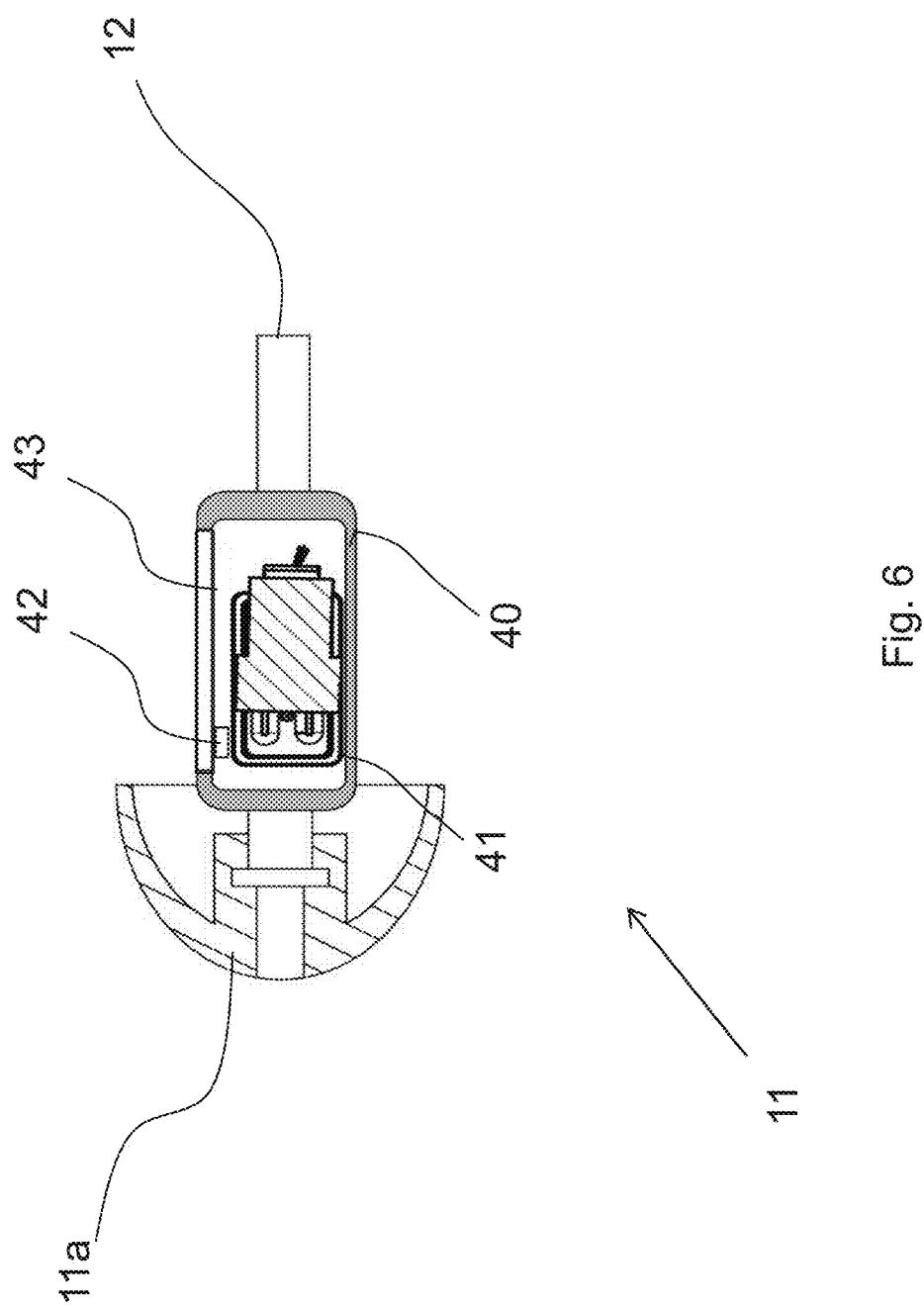
FIG. 6 illustrates an in-the-ear part (unit) of a receiver-in-the-ear hearing aid according to an embodiment of the disclosure.

Now referring to FIG. 6 which illustrates an in-the-ear part (unit) of a receiver-in-the-ear hearing aid according to an embodiment of the disclosure.

As can be seen in FIG. 6, at least one sensor or at least one active electronic component 42 is placed within the transducer air volume 43. The transducer air volume 43 is air volume which is enclosed by said capsule 40 (enclosing at least the transducer sound active part 41) and which is in fluid-connection with said transducer sound active part 41 (and may preferably by in fluid-connection with said capsule).

Here, "within" means directly within (i.e. in contact with and surrounded by) the transducer air volume, or having a housing within (i.e. in contact with and surrounded by) the transducer air volume. Further, "within" also includes protruding into said transducer air volume (with a portion or housing thereof). In other words, the at least one sensor or said at least one active electronic component or a housing thereof at least protrudes into the transducer air volume.

The sensor/component is connected to the transducer (i.e. electronic/sound active part thereof) and/or to the connection tube 12 (wires enclosed therein) via litz wires and/or via printed circuit boards and/or via flexible flat cables and/or via laser direct structuring (LSD/MID) on plastic. The connection of the sensor/component 42 is not limited to the mentioned options.

Figure 7:
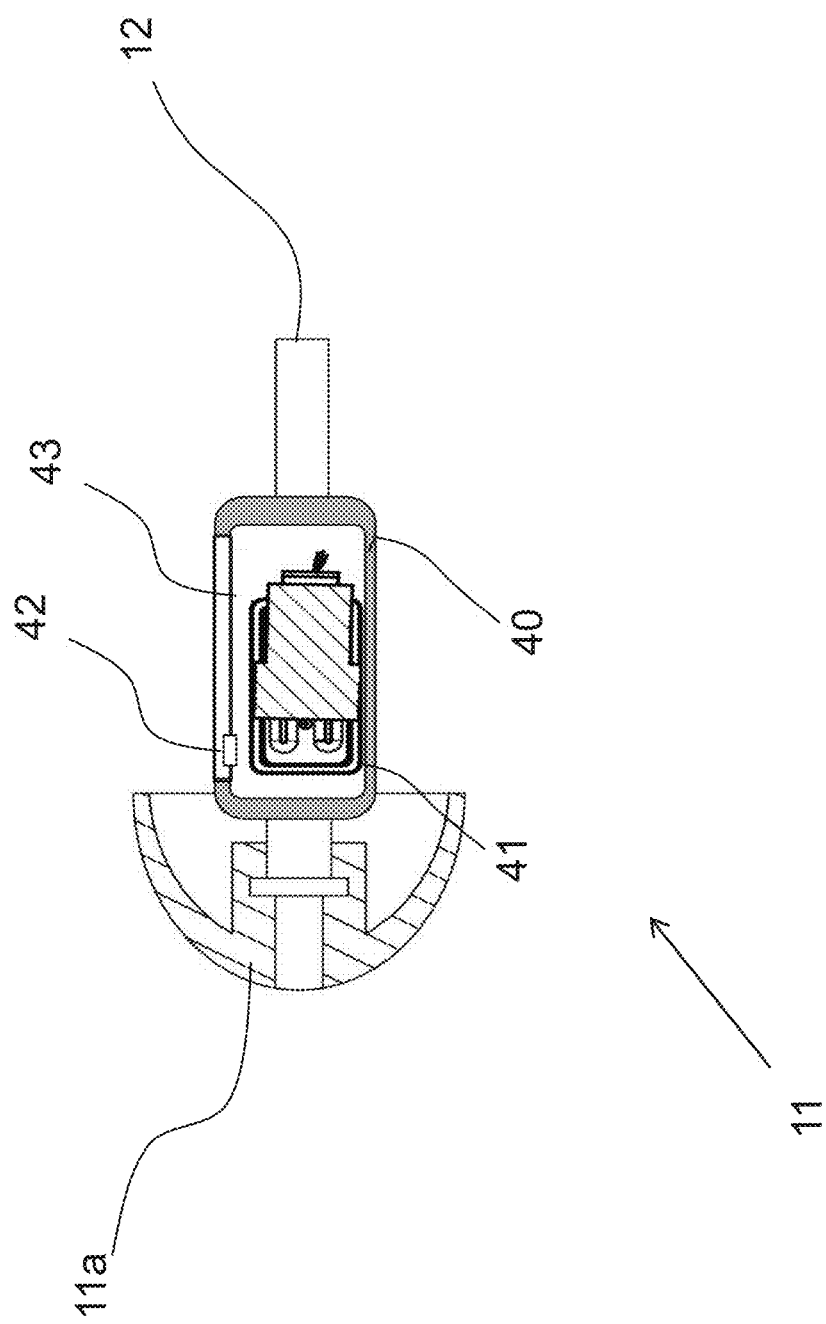
FIG. 7 illustrates an in-the-ear part (unit) of a receiver-in-the-ear hearing aid according to an embodiment of the disclosure.

Now referring to FIG. 7 which illustrates an in-the-ear part (unit) of a receiver-in-the-ear hearing aid according to an embodiment of the disclosure.

As can be seen in FIG. 7, the sensor/component 42 may protrude into the capsule 40 while still being within the transducer air volume 43.

Figure 8:
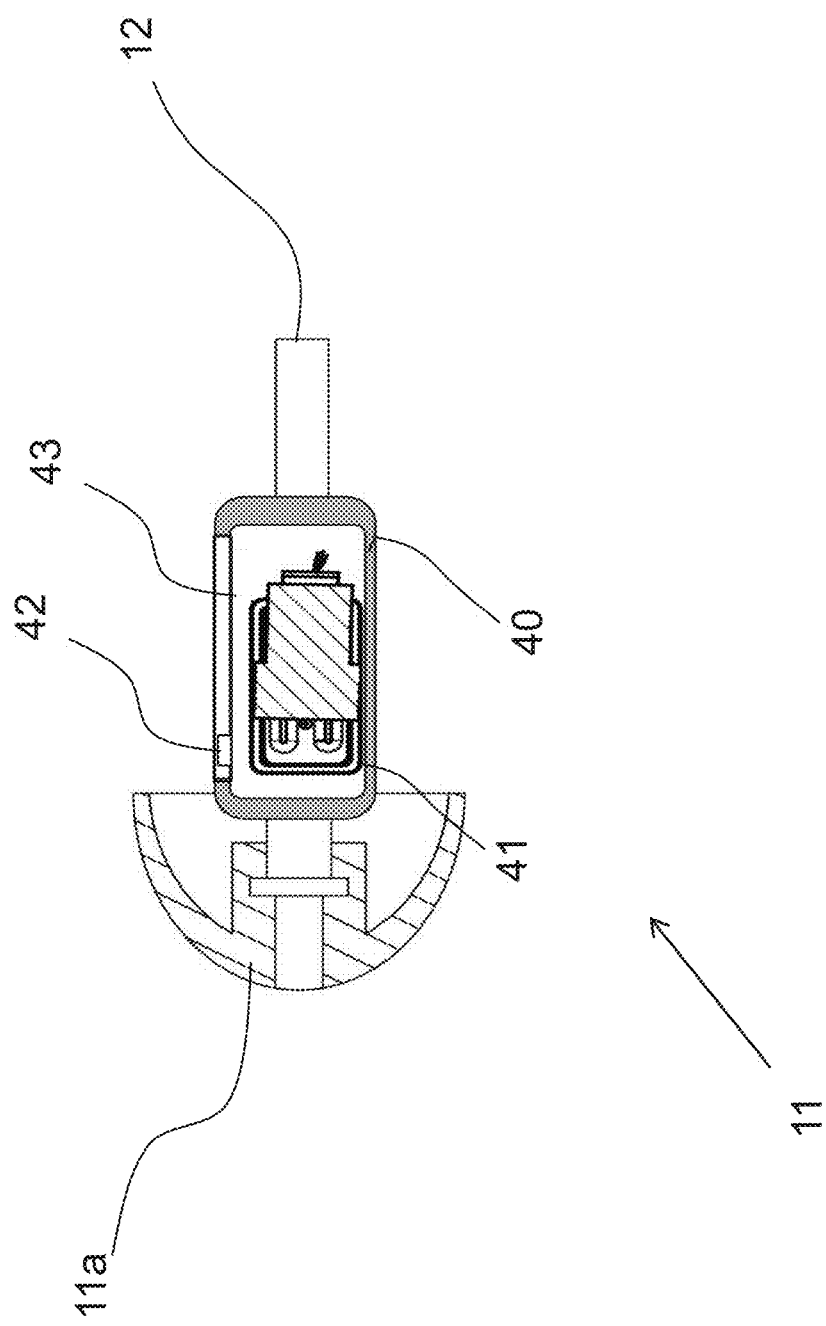
FIG. 8 illustrates an in-the-ear part (unit) of a receiver-in-the-ear hearing aid according to an embodiment of the disclosure.

Now referring to FIG. 8 which illustrates an in-the-ear part (unit) of a receiver-in-the-ear hearing aid according to an embodiment of the disclosure.

Comparable, as can be seen in FIG. 8, the sensor/component 42 may be nearly embedded in the capsule 40 while still being within the transducer air volume 43.

Figure 9:
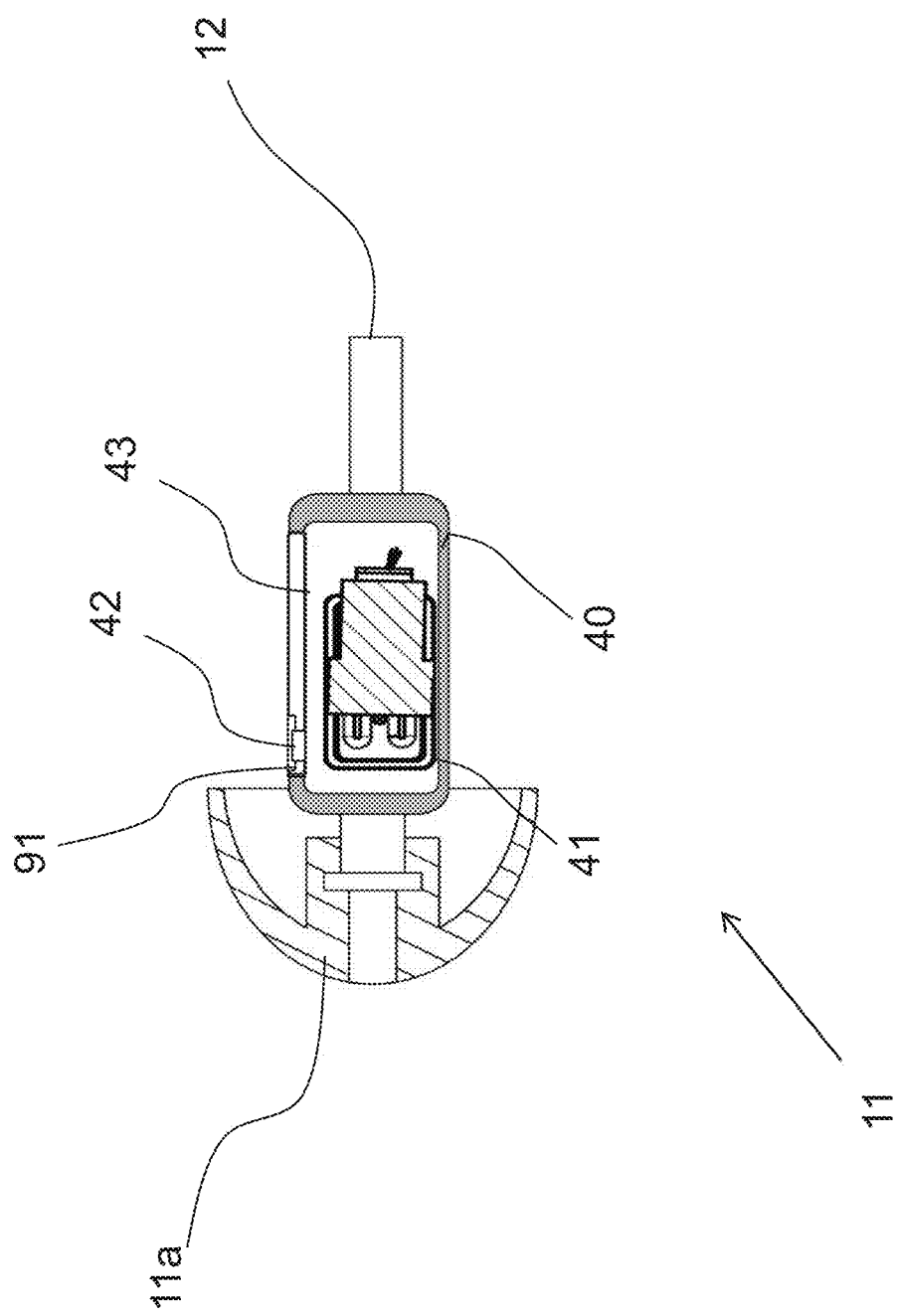
FIG. 9 illustrates an in-the-ear part (unit) of a receiver-in-the-ear hearing aid according to an embodiment of the disclosure.

Now referring to FIG. 9 which illustrates an in-the-ear part (unit) of a receiver-in-the-ear hearing aid according to an embodiment of the disclosure.

As can be seen in FIG. 9, the sensor/component 42 may penetrate the capsule 40 while still being within the transducer air volume 43. The capsule may have a recess 91 at the position where the sensor/component 42 penetrates the capsule 40.

Figure 10:
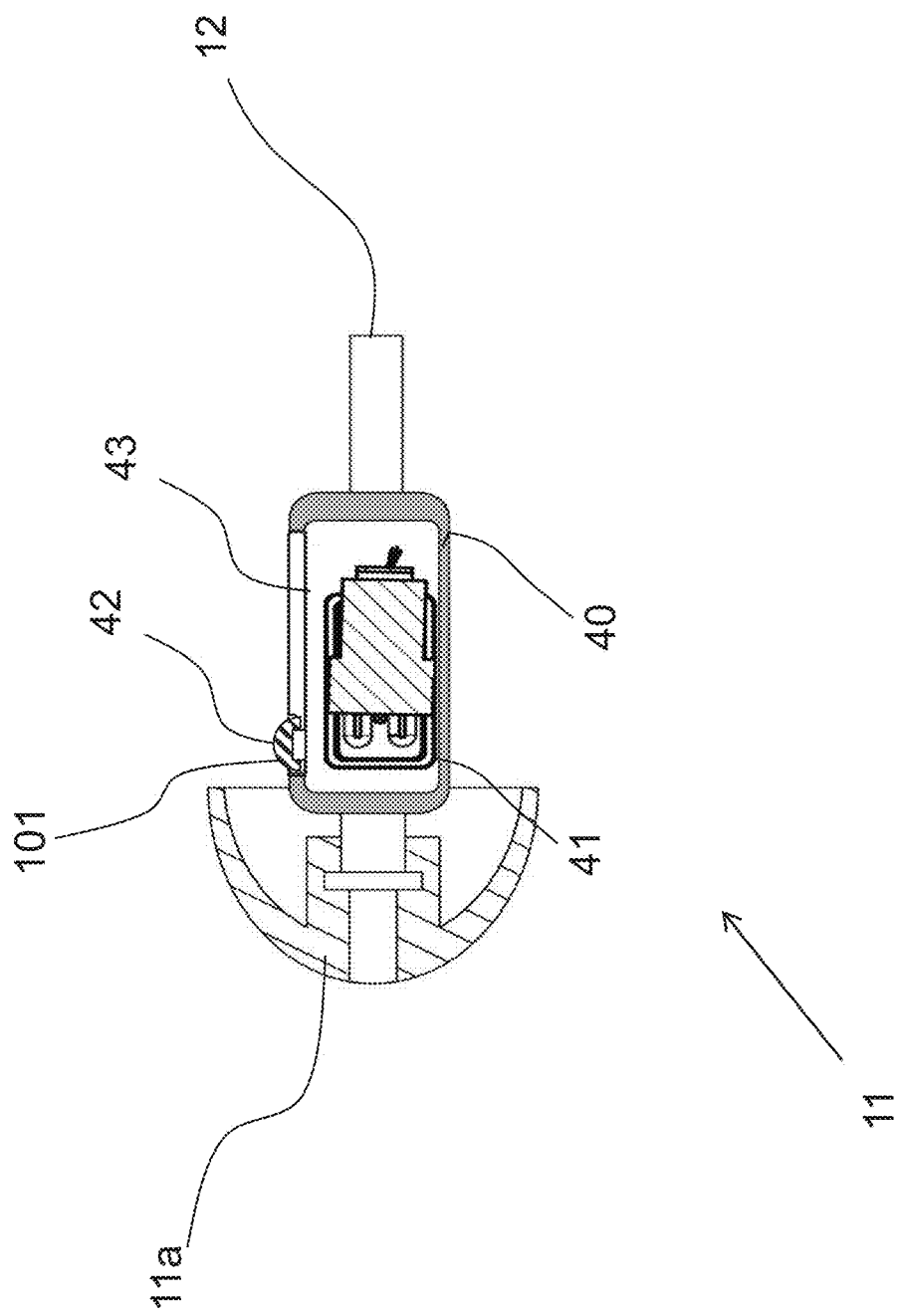
FIG. 10 illustrates an in-the-ear part (unit) of a receiver-in-the-ear hearing aid according to an embodiment of the disclosure.

Now referring to FIG. 10 which illustrates an in-the-ear part (unit) of a receiver-in-the-ear hearing aid according to an embodiment of the disclosure.

As can be seen in FIG. 10, the sensor/component 42 may penetrate the capsule 40 while still being within the transducer air volume 43. The sensor/component 42 may be covered by a cover element 101 at the position where the sensor/component 42 penetrates the capsule 40. The cover element may have characteristics facilitating or at least allowing functionalities of the sensor/component 42. For example, the cover element 101 may be translucent and/or translucent while protecting the sensor/component 42 from mechanical impacts. The characteristics of the cover element 101 are not limited to the mentioned examples.

Figure 11:
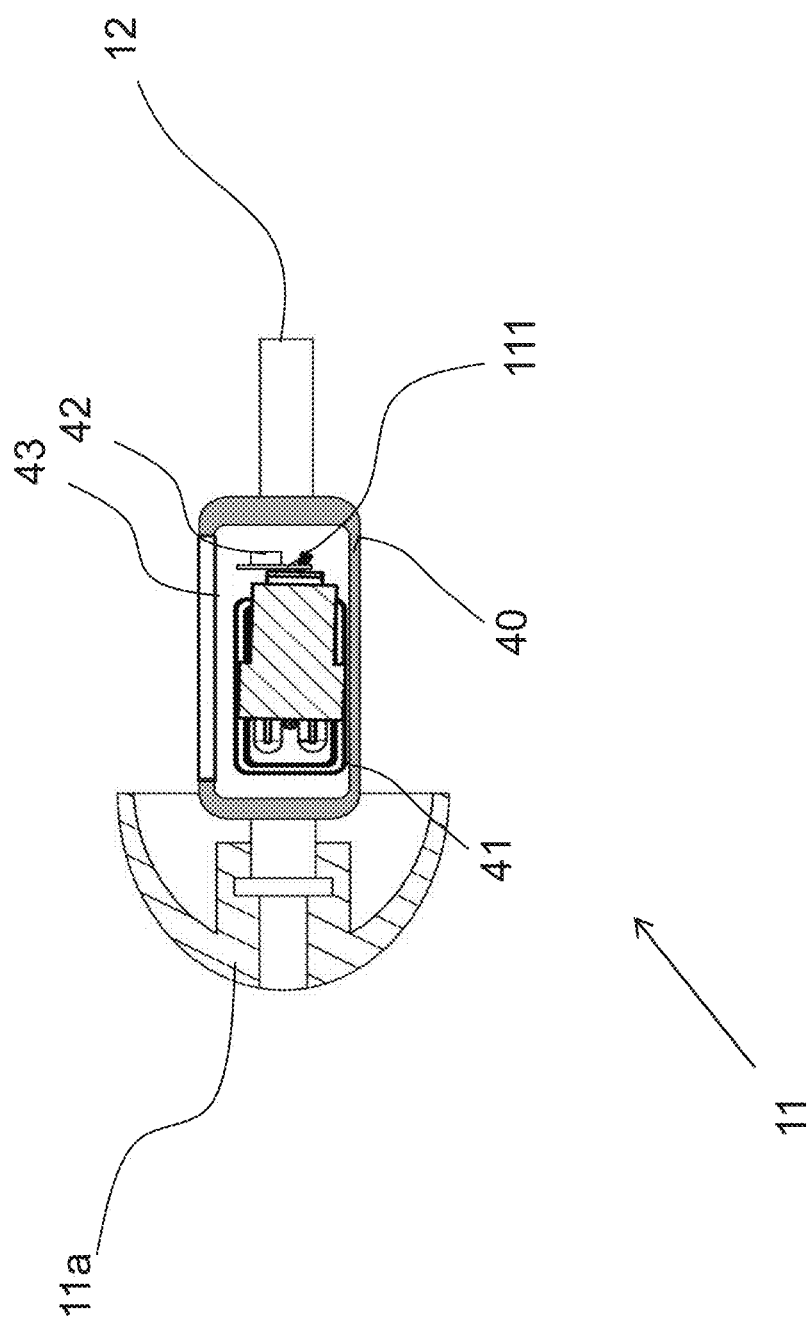
FIG. 11 illustrates an in-the-ear part (unit) of a receiver-in-the-ear hearing, aid according, to an embodiment of the disclosure.

Now referring to FIG. 11 which illustrates an in-the-ear part (unit) of a receiver-in-the-ear hearing aid according to an embodiment of the disclosure.

As can be seen in FIG. 11, the sensor/component 42 may be provided in the back of the electro-acoustic transducer instead of in front of it.

The sensor/component 42 may be provided anywhere within the capsule as long as being within the transducer air volume.

Figure 12:
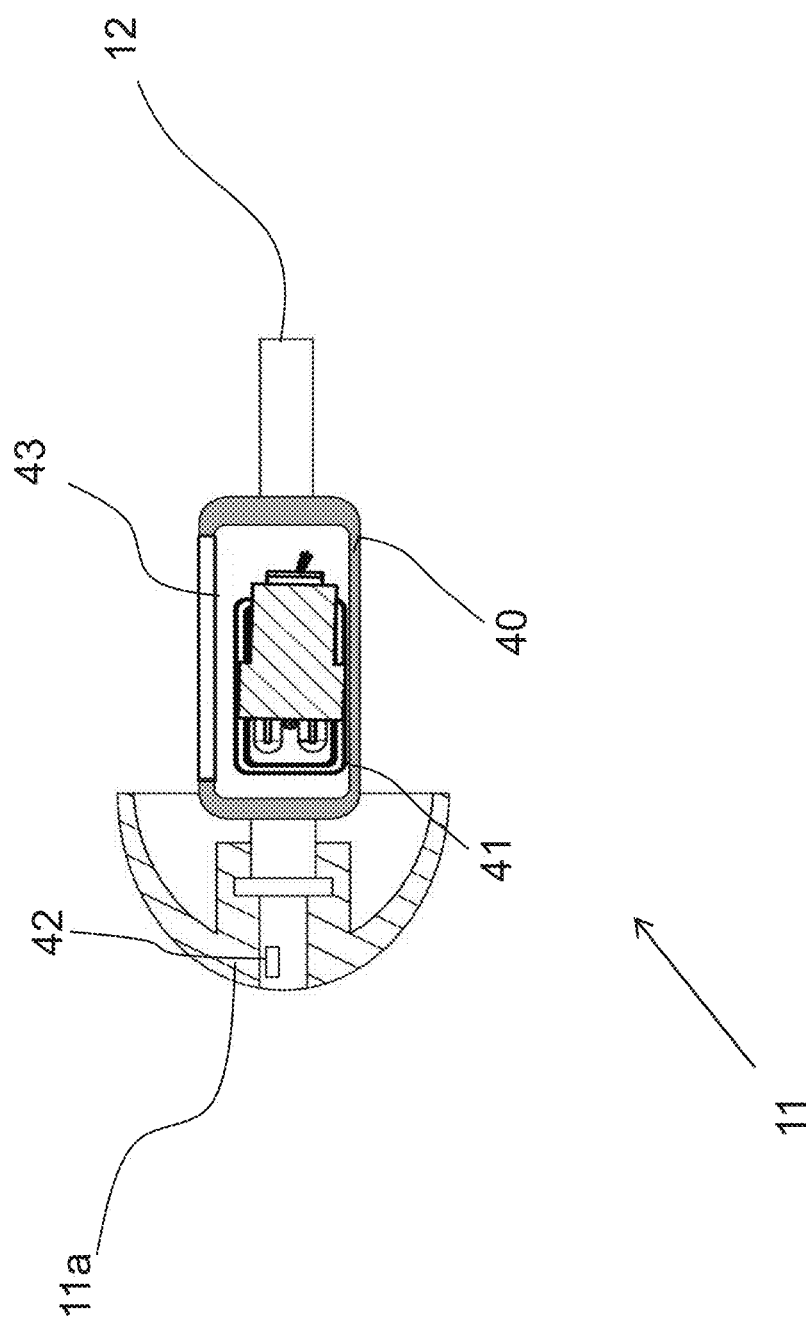
FIG. 12 illustrates an in-the-ear part (unit) of a receiver-in-the-ear hearing aid according to an embodiment of the disclosure.

Now referring to FIG. 12 which illustrates an in-the-ear part (unit) of a receiver-in-the-ear hearing aid according to an embodiment of the disclosure.

As can be seen in FIG. 12, the elastic dome 11a may have a passage therethrough. The capsule 40 defined by enclosing the transducer air volume may include the elastic dome. The passage through the dome may be in fluid-connection with a receiver outlet of the in-the-ear hearing aid device 11, while the receiver outlet of the in-the-ear hearing aid device 11 is in fluid-connection with the transducer sound active part.

Hence, the sensor (or active electronic component) may be provided within the transducer air volume within the passage of the elastic dome 11a.

Consequently, when worn by the user, the user's ear canal may be in fluid-connection with the transducer sound active part.

Figure 13:
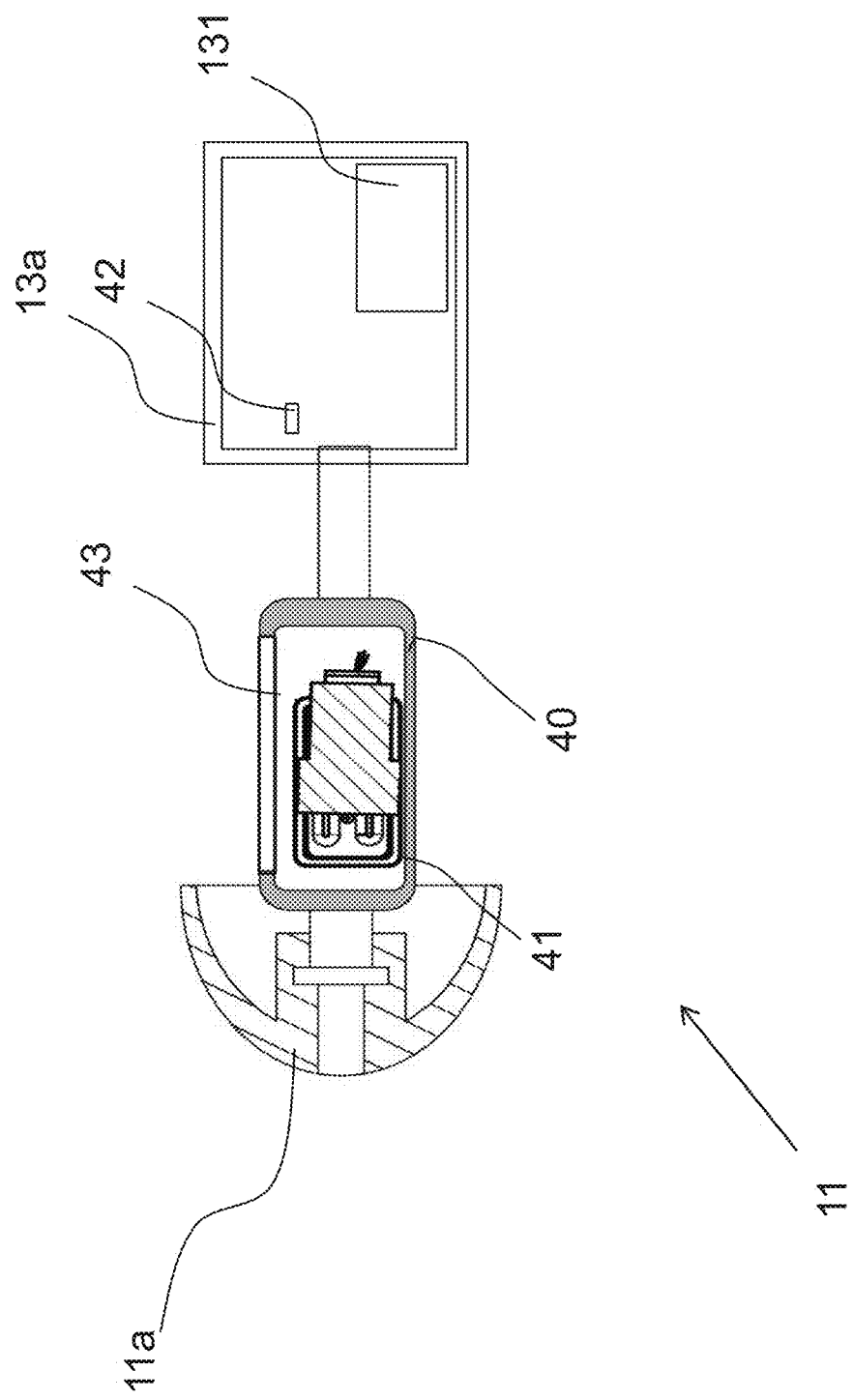
FIG. 13 illustrates an in-the-ear part (unit) of a receiver-in-the-ear hearing aid according to an embodiment of the disclosure.

Now referring to FIG. 13 which illustrates an in-the-ear part (unit) of a receiver-in-the-ear hearing aid according to an embodiment of the disclosure.

As can be seen in FIG. 12, the connection tube 12 may be connected to a behind-the-ear hearing aid device 13 and in particular with a housing 13a thereof accommodating a unit 131 (e.g. a processor) of the behind-the-ear hearing aid device 13. A volume thereof in fluid-connection with a volume in the connection tube which in turn is in fluid connection with the transducer sound active part may thus house the sensor (or active electronic component) 42 as well.

Figure 14:
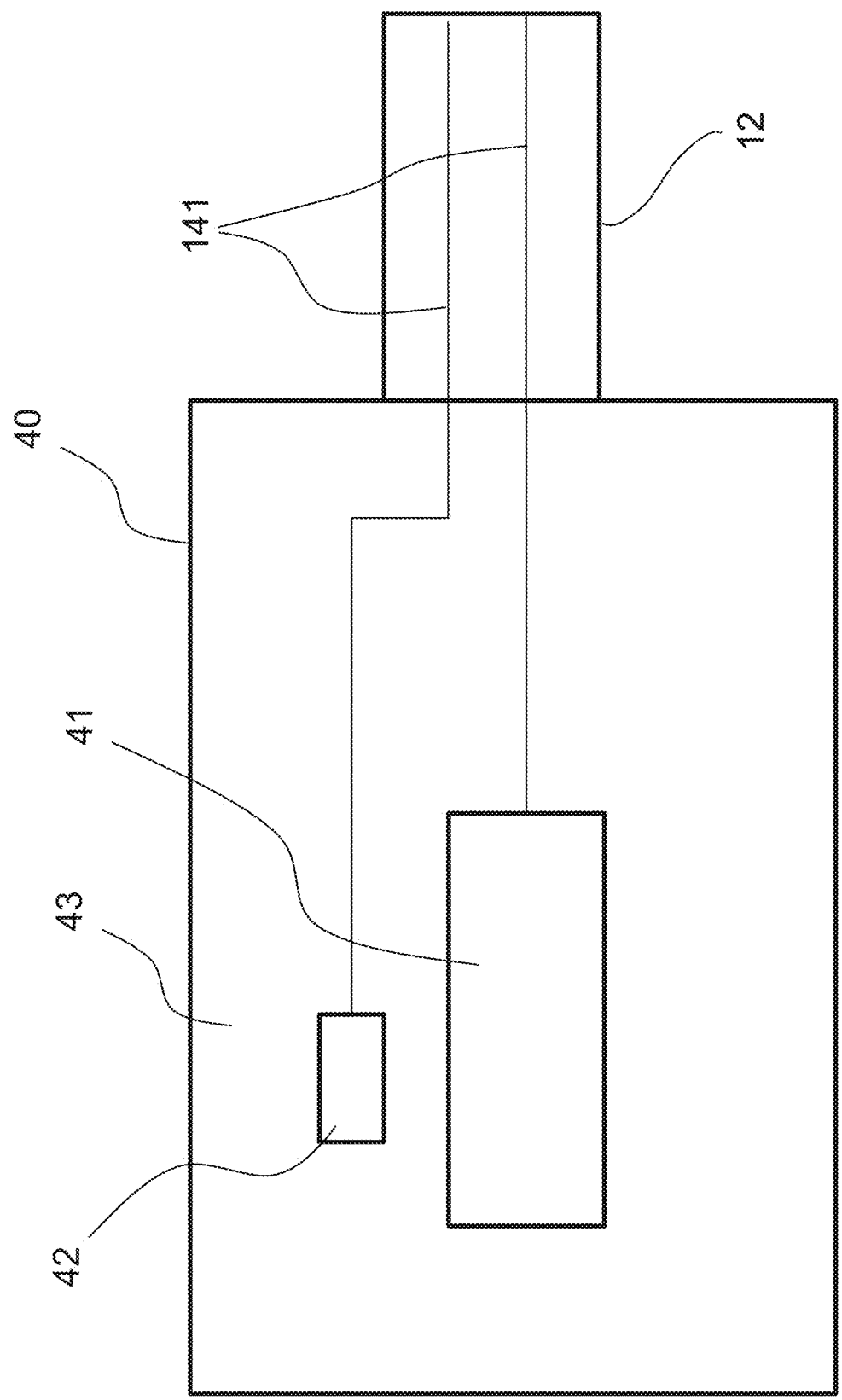
FIG. 14 illustrates an in-the-ear part (unit) of a receiver-in-the-ear hearing aid according to an embodiment of the disclosure.

Now referring to FIG. 14 which illustrates an in-the-ear part (unit) of a receiver-in-the-ear hearing aid according to an embodiment of the disclosure.

In particular, FIG. 14 illustrates schematically a potential electrical layout of an in-the-ear hearing aid device 11 comprising the transducer sound active part 41 (which may also include transducer electronics driven by input signals) and an additional element 42, e.g. a sensor (preferably a temperature sensor) or an active electronic component. Both the transducer sound active part 41 and the additional element 42 are enclosed by the capsule 40 of the transducer. In particular, the additional element 42 is placed within the transducer air volume 43.

Both the transducer sound active part 41 and the additional element 42 are connected to a wiring 141 which may pass through the connection tube to the above-mentioned behind-the-ear hearing aid device and particular electronic components thereof, e.g. a sound processor and/or a sensor control part.

The transducer electronics/transducer sound active part 41 may belong to an output transducer (receiver) in fluid-connection with an outlet opening or may belong to an input transducer (microphone) in fluid-connection with an inlet opening.

In other words, the additional element 42 may be placed in transducer air volume 43 of an electro-acoustic output transducer (receiver, speaker) or may be placed in transducer air volume 43 of an electro-acoustic input transducer (microphone).

Figure 15:
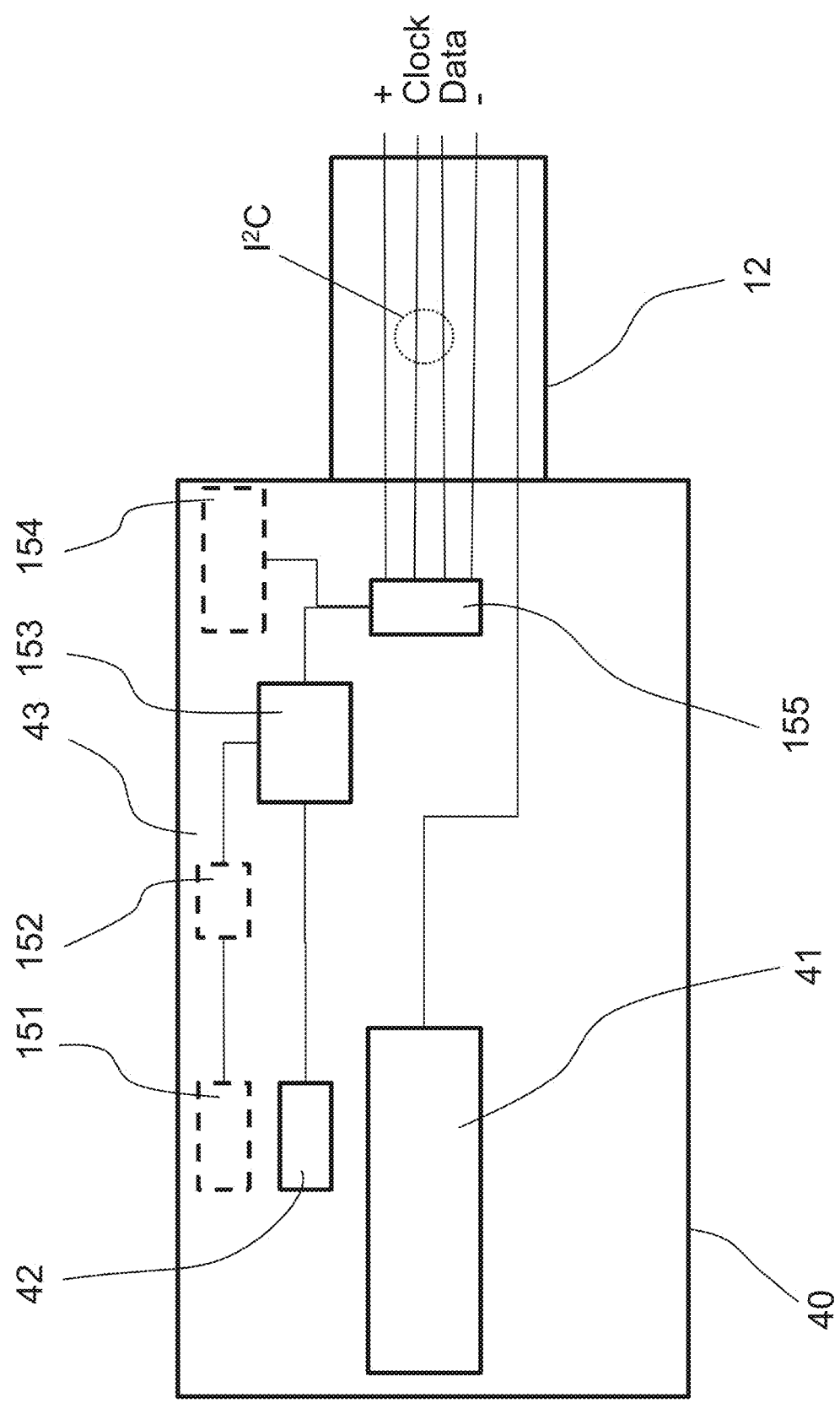
FIG. 15 illustrates an in-the-ear part (unit) of a receiver-in-the-ear hearing aid according to an embodiment of the disclosure.

Now referring to FIG. 15 which illustrates an in-the-ear part (unit) of a receiver-in-the-ear hearing aid according to an embodiment of the disclosure.

Namely, beside for sensors in the acoustic volume, the transducer air volume can also be used for pre-processors (digital signal processors, DSP's), pre-amplifiers, and AD/DA-converters (AD: analogue-digital; DA: digital-analogue) for e.g. electroencephalography (EEG) electrodes, galvanic skin response electrodes, electrooculography (EOG) electrodes, a digital speaker communication bus to the behind the ear unit, etc.

FIG. 15 illustrates schematically a potential electrical layout of an in-the-ear hearing aid device 11 with digital and analogue linkage to the potential behind-the-ear hearing aid device.

Namely, while in FIG. 15 the electro-acoustic transducer 41 is connected via an analogue connection, further elements may be connected via a digital connection, in particular a digital bus, for example an I$^2$C bus comprising wiring for power, ground, I$^2$C clock and I$^2$C data, wherein at least three different states of the bus are applied in different time slots, where a first state is for transfer of power, a second state is for transmission of signal from a behind-the-ear hearing device to the in-the-ear hearing aid device, and a third state is for transmission of signal from the in-the-ear hearing aid device to the behind-the-ear hearing device.

When separating in time the power transfer from the data transfer the risk of noise problems is reduced. The term different time slots refers to this separation in time of power transfer and data or signal transfer in both directions. At the same time the invention facilitates a two wire bus without the need of any further electrical wires.

A bus is here understood to be a digital communication line which can be set up for communication between different units, suitable for carrying signals in more than one direction. The bus is a serial databus, and is here also understood to be able to transfer power.

In an embodiment of a hearing aid, a fourth state of the bus is added which is set to low, i.e. to "0", in order for the first state for power transfer to start with a rising edge. Such a rising edge occurring at a known place in the sequence is important in order to interpret the signal on the bus.

The first state for transfer of power takes up at least 50%, preferably at least 70%, of the time on the bus. This has been found to result in a sufficiently small power loss and a not too large capacitor for supplying power in the rest of the time.

the electro-acoustic transducer in the in-the-ear hearing aid device is connected such that it will not draw any power in the time where data is transferred on the bus, but only in the time where power is transferred. This can be achieved by short-circuiting the receiver during the transfer of data. The advantage of this will be that the receiver will not need to draw power from a capacitor in the electro-acoustic transducer or in the in-the-ear hearing aid device during the time where there is no transfer of power from the behind-the-ear hearing device. This means that the capacitor in the electro-acoustic transducer or in the in-the-ear hearing aid device can be made much smaller, since it will only need to supply power to the electronic circuit of the ear plug part. A smaller capacitor will also have smaller physical dimensions, whereby the electro-acoustic transducer or the in-the-ear hearing aid device can be made smaller. There are possible variations of this embodiment, e.g. where the receiver draws power in a smaller part of the time where data is transferred.

The additional elements placed within the transducer air volume may thus include, for example, a sensor, preferably a temperature sensor 42, linked via an AD converter 153, other sensors 151 (e.g. electrodes for EEG measurements or galvanic skin resistance measurements, light sensors for pulse or blood oxidation measurements, microphones, moisture sensors, capacitive touch sensors), a pre-amplifier 152 associated with a respective other sensor, the AD converter 153, RITE detection components 154, and sensor fusion circuitry 155, where at least a portion of the additional elements are connected to the mentioned digital bus via the sensor fusion circuitry 155.

The at least one electro-acoustic transducer 41, and at least one sensor 42 and/or the at least one active electronic component (151-154) are connected to the wires 141 via a multiplexer (155). For example, the sensor signals may be merged with audio signals transmitted to the electro-acoustic transducer 41 and transmitted via the same wires 141, by transmitting the sensor signals outside a passband of the electro-acoustic transducer 41, e.g. below 100 HZ and above 10 KHz.

Figure 16:
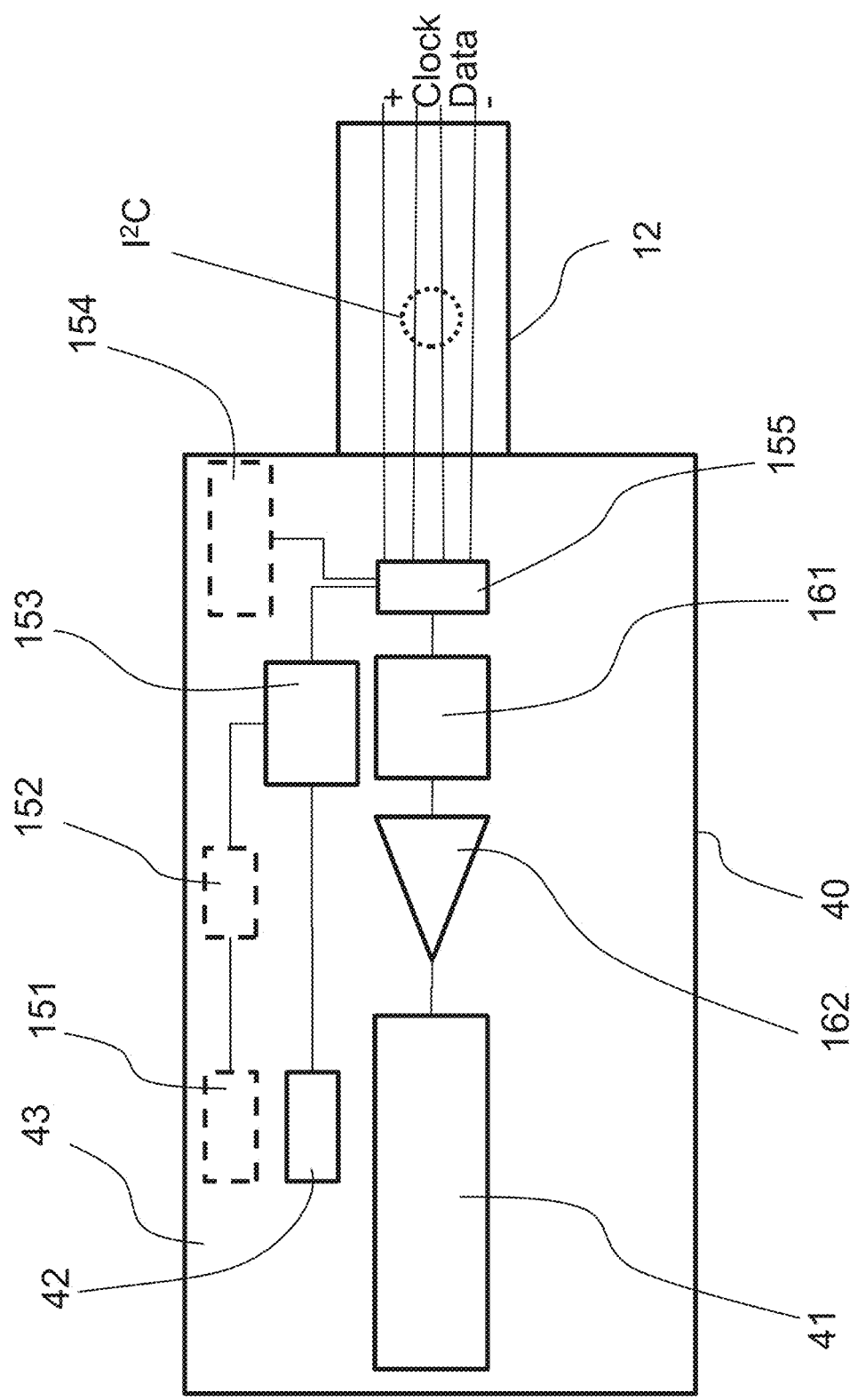
FIG. 16 illustrates an in-the-ear part (unit) of a receiver-in-the-ear hearing aid according to an embodiment of the disclosure.

Now referring to FIG. 16 which illustrates an in-the-ear part (unit) of a receiver-in-the-ear hearing aid according to an embodiment of the disclosure.

FIG. 16 illustrates schematically a potential electrical layout of an in-the-ear hearing aid device 11 with digital linkage to the potential behind-the-ear hearing aid device.

Namely, while in FIG. 15 the electro-acoustic transducer 41 is connected via an analogue connection, in FIG. 16 both the further elements and the electro-acoustic transducer 41 may be connected via a digital connection, in particular a digital bus, for example an I²C bus comprising wiring for power, ground, I²C clock and I²C data.

The additional elements placed within the transducer air volume may thus include, for example, a sensor, preferably a temperature sensor 42, linked via an AD converter 153, other sensors 151 (e.g. electrodes for EEG measurements or galvanic skin resistance measurements, light sensors for pulse or blood oxidation measurements, microphones, moisture sensors, capacitive touch sensors), a pre-amplifier 152 associated with a respective other sensor, the AD converter 153, RITE detection components 154, a DA converter 161 and an amplifier 162 for driving the electro-acoustic transducer 41, and sensor fusion circuitry 155, where at least a portion of the additional elements are connected to the mentioned digital bus via the sensor fusion circuitry 155.

A portion of the additional elements (e.g. the pre-amplifier 152, the AD converter 153, the RITE detection components 154, the DA converter 161, the amplifier 162, and the sensor fusion circuitry 155) may be integrated in an integrated circuit (IC).

Figure 17:
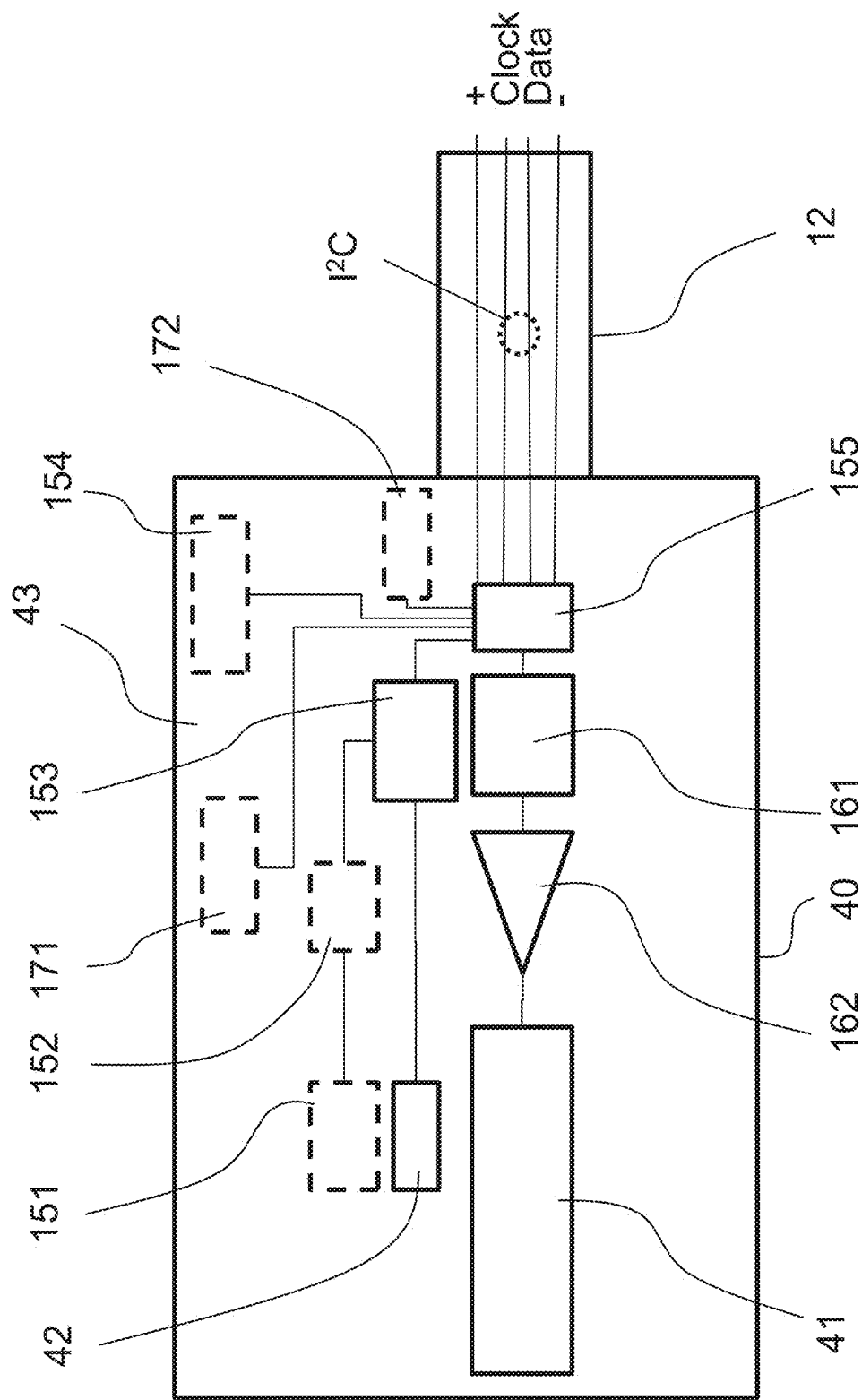
FIG. 17 illustrates an in-the-ear part (unit) of a receiver-in-the-ear hearing aid according to an embodiment of the disclosure.

Now referring to FIG. 17 which illustrates an in-the-ear part (unit) of a receiver-in-the-ear hearing aid according to an embodiment of the disclosure.

FIG. 17 illustrates schematically a potential electrical layout of an in-the-ear hearing aid device 11 with digital linkage to the potential behind-the-ear hearing aid device.

Just like with FIG. 16, in FIG. 17 both the further elements and the electro-acoustic transducer 41 are connected via a digital connection, in particular a digital bus, for example an I2C bus comprising wiring for power, ground, I2C clock and I2C data.

In addition to the additional elements placed within the transducer air volume of the in-the-ear hearing aid device 11 illustrated in FIG. 16, the in-the-ear hearing aid device 11 of FIG. 17 may further comprise a digital sensor 171 directly connected to the sensor fusion circuitry 155 and a memory 172 for example storing calibration data in relation to the electro-acoustic transducer and/or sensors or other active electronic components placed within the transducer air volume 43.

A portion of the additional elements (e.g. the pre-amplifier 152, the AD converter 153, the RITE detection components 154, the DA converter 161, the amplifier 162, the sensor fusion circuitry 155, and the memory 172) may be integrated in an integrated circuit (IC).

Figure 18:
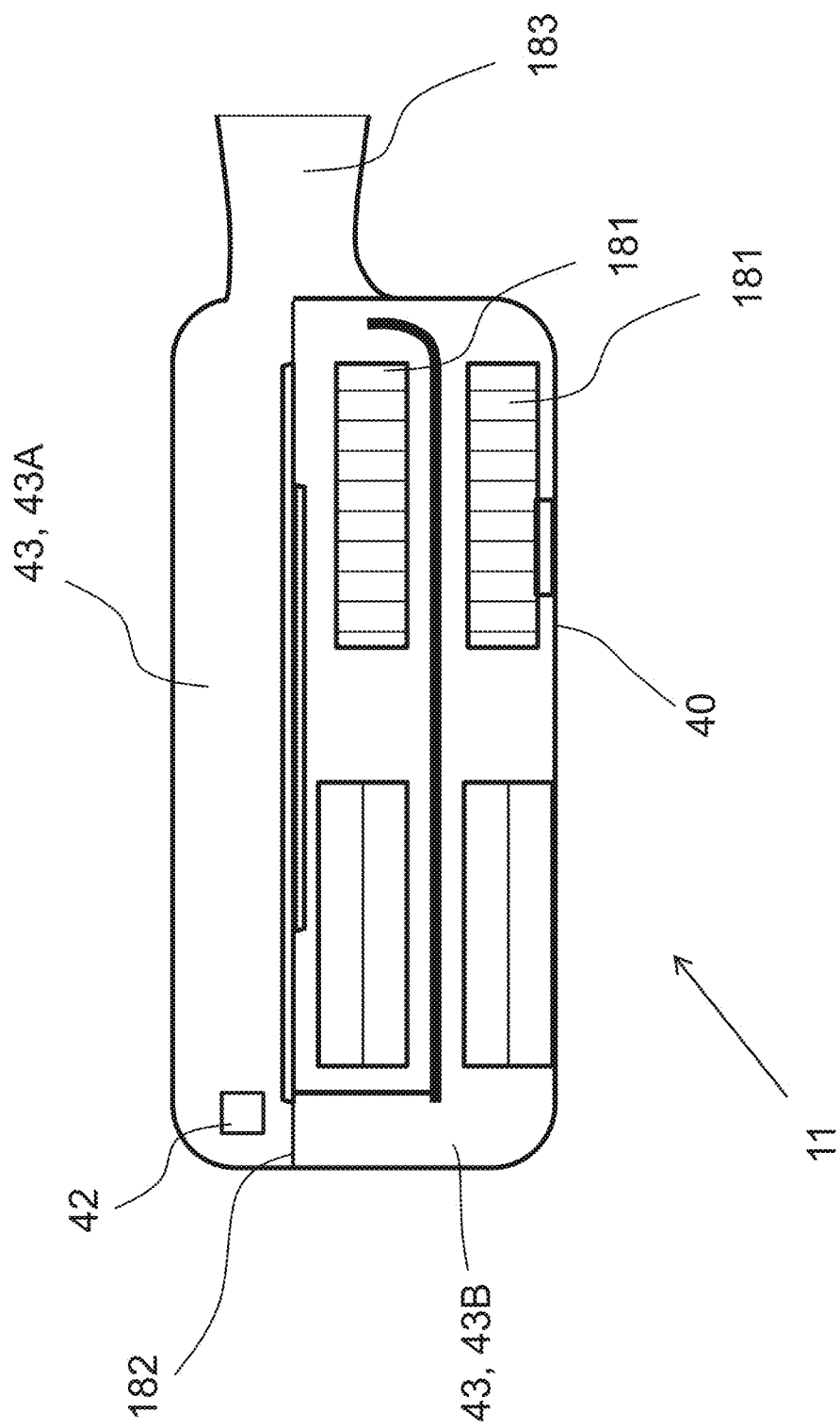
FIG. 18 illustrates an in-the-ear part (unit) of a receiver-in-the-ear hearing aid according to an embodiment of the disclosure.

Now referring to FIG. 18 which illustrates an in-the-ear part (unit) of a receiver-in-the-ear hearing aid according to an embodiment of the disclosure.

As is illustrated in FIG. 18, the transducer air volume 43 of the in-the-ear hearing aid device 11 may be separated into two transducer air volumes which are not in fluid-connection with each other, a first transducer air volume 43A and a second transducer air volume 43B.

The two transducer air volumes may be separated from each other by a separation part 182. The separation part may be at least a portion of the transducer sound active part. For example, the separation part 182 may be the membrane (diaphragm) of an electro-acoustic output transducer.

In FIG. 18, the transducer air volume 43 is separated into an upper transducer air volume (e.g. first transducer air volume) and a lower transducer air volume (e.g. second transducer air volume). However, the two transducer air volumes are not limited to being arranged one above the other. Contrary thereto, the two transducer air volumes may also be arranged side by side or in any other relation to each other as long as being enclosed by the capsule 40 and being not in fluid connection to each other. Nevertheless, for ease of illustration and understanding, in the following is referred to upper and lower transducer air volumes, but the explanation is applicable as well two transducer air volumes in any other relation mentioned above.

One of the two transducer air volumes may be in fluid connection with a (sound) inlet/outlet 183 of the in-the-ear hearing aid.

Elements 181 of the transducer, e.g. magnets and coils, may be arranged in one of the two separated transducer air volumes.

At least one sensor (or active electronic component) 42 may be placed within one of the two separated transducer air volumes.

In FIG. 18, the at least one sensor (or active electronic component) 42 is placed within the upper transducer air volume.

Figure 19:
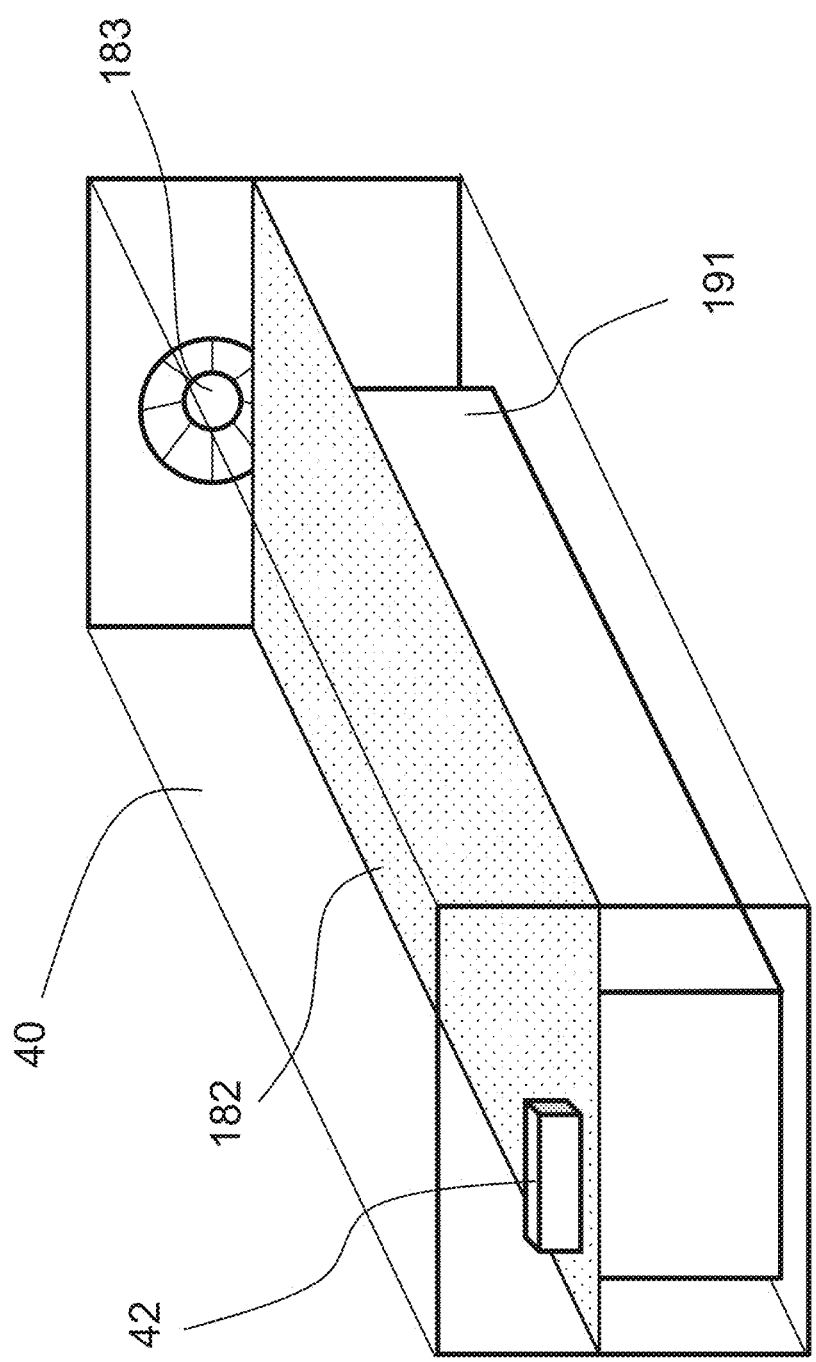
FIG. 19 illustrates an in-the-ear part (unit) of a receiver-in-the-ear hearing aid according to an embodiment of the disclosure.

Now referring to FIG. 19 which illustrates an in-the-ear part (unit) of a receiver-in-the-ear hearing aid according to an embodiment of the disclosure.

In particular, FIG. 19 illustrates another view of the in-the-ear hearing aid device 11 shown in FIG. 18.

The elements 181 of the transducer may be grouped together to a group of elements 191 of the transducer. This group of elements may be enclosed by a respective housing, as shown in FIG. 19, but is not limited to such implementation.

Figure 20:
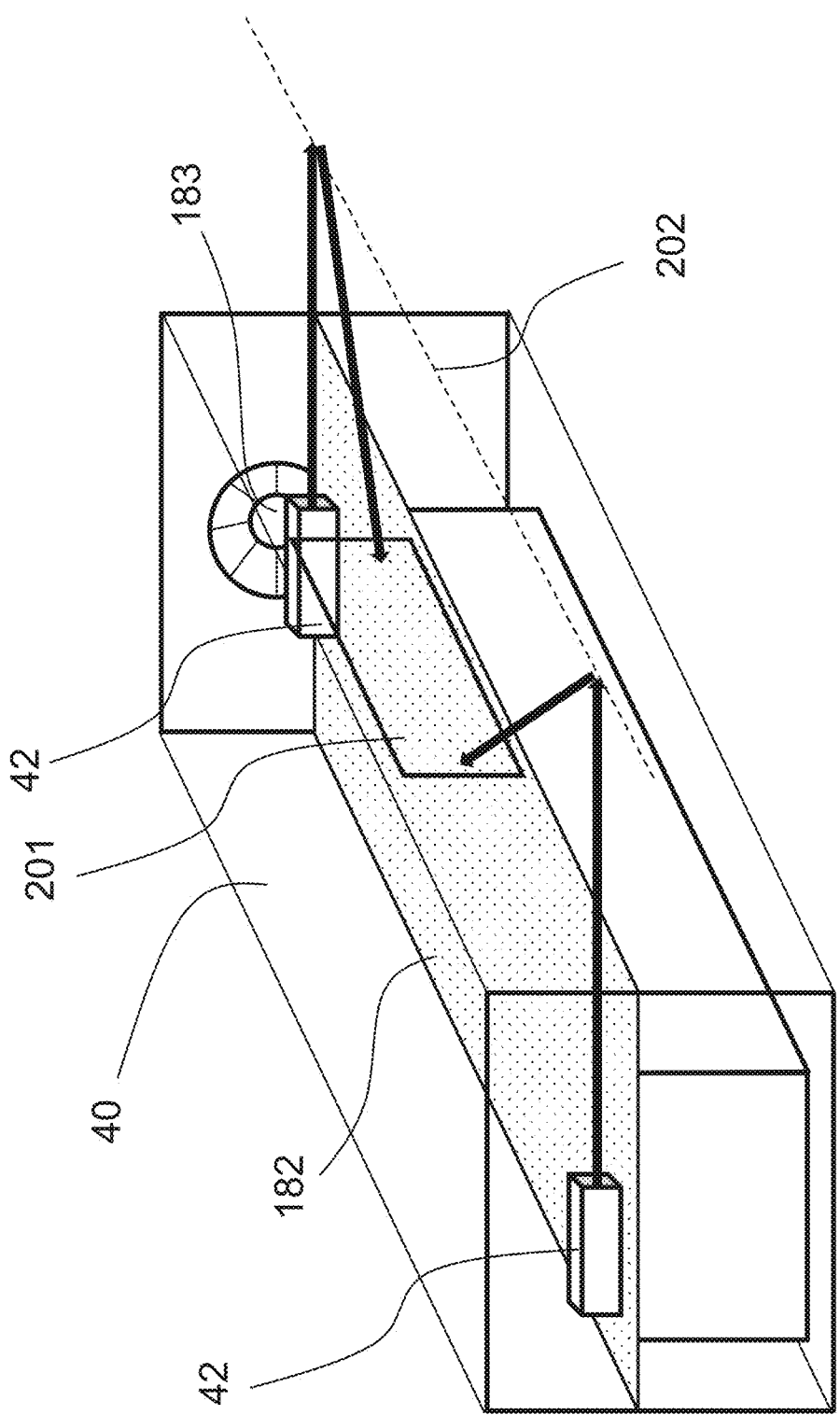
FIG. 20 illustrates an in-the-ear part (unit) of a receiver-in-the-ear hearing aid according to an embodiment of the disclosure.

Now referring to FIG. 20 which illustrates an in-the-ear part (unit) of a receiver-in-the-ear hearing aid according to an embodiment of the disclosure.

As can be seen in FIG. 20, more than one sensors (or active electronic components) 42 may be placed within the upper transducer air volume.

For specific measurement applications, at least an emitting device and a receiving device are necessary.

In the example shown in FIG. 20, two emitting devices 42 (e.g. light emitting diodes) and one receiving device 201 (e.g. light receiving element) are arranged to measure any characteristic of measurement object 202 e.g. using light (indicated by arrows in FIG. 20) reflected from the measurement object 202. The measurement may be effected through openings or specifically featured walls of the capsule. Measurement applications are not limited to such arrangement.

Figure 21:
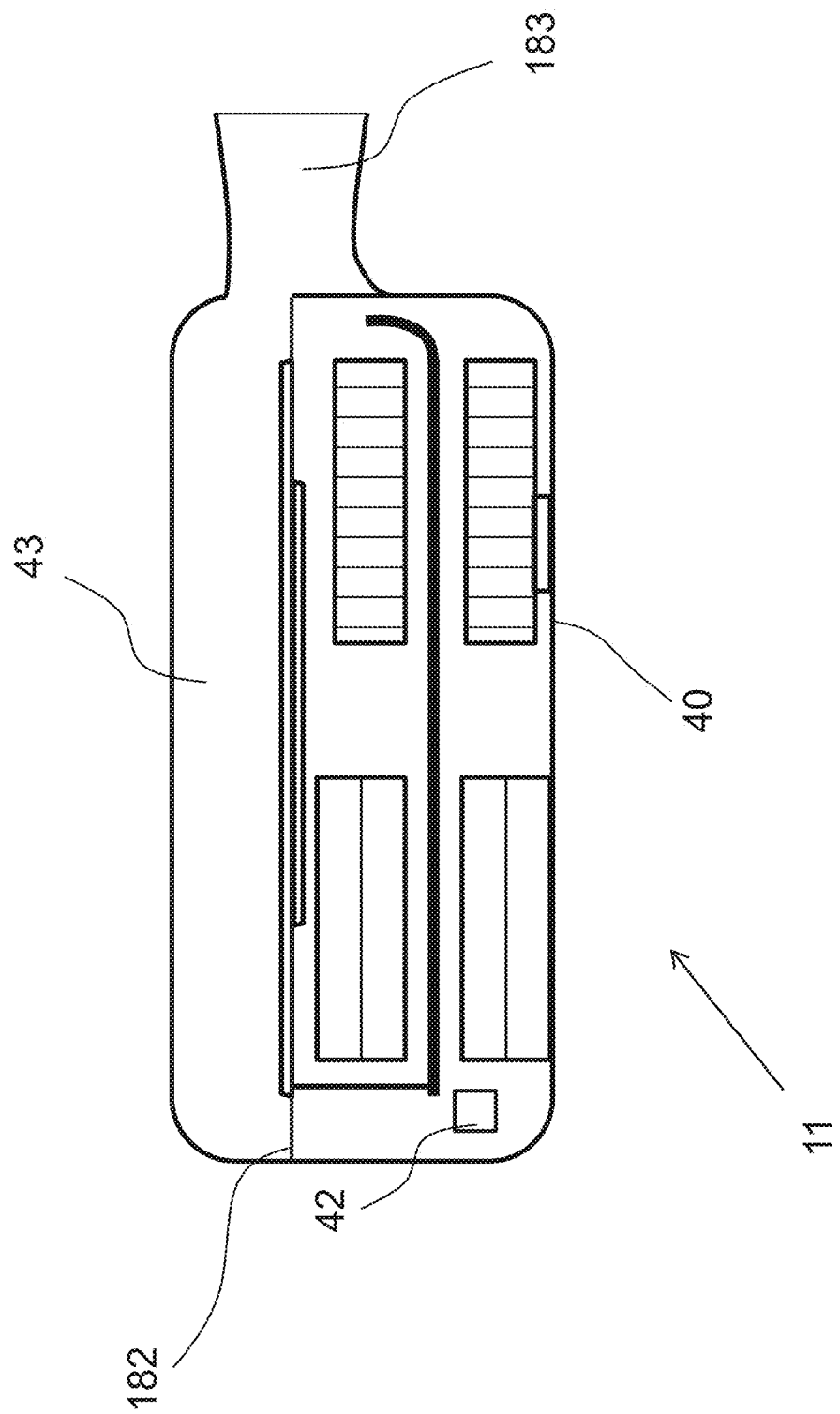
FIG. 21 illustrates an in-the-ear part (unit) of a receiver-in-the-ear hearing aid according to an embodiment of the disclosure.

Now referring to FIG. 21 which illustrates an in-the-ear part (unit) of a receiver-in-the-ear hearing aid according to an embodiment of the disclosure.

Contrary to FIG. 18, in FIG. 21, the at least one sensor (or active electronic component) 42 is placed within the lower transducer air volume.

The at least one sensor may be placed within the larger of the two separated transducer air volumes. Since in such case the at least sensor is arranged within the larger of the two transducer air volumes, an effect of the at least one sensor on the acoustic characteristics of the transducer is not noticeable to the user.

Figure 22:
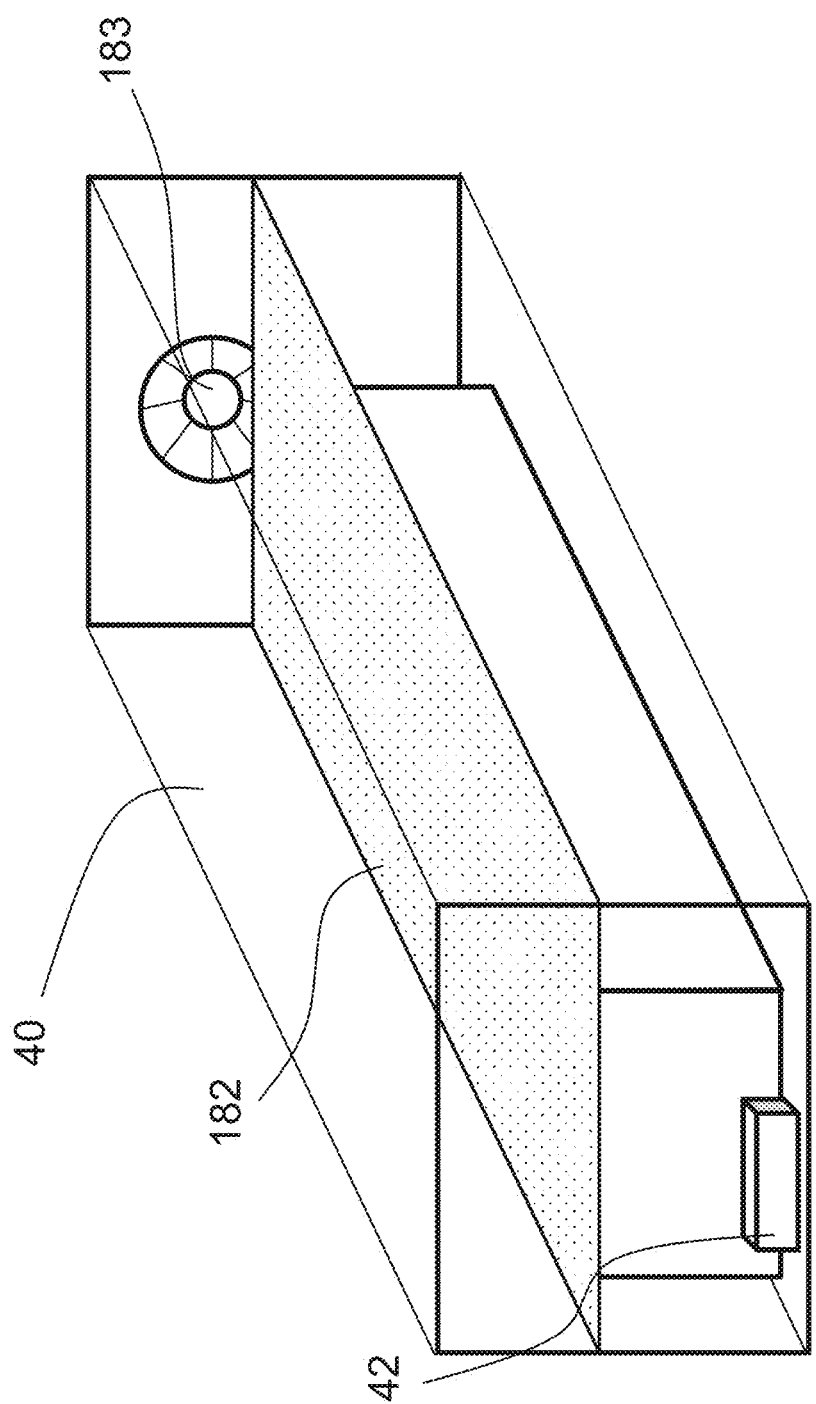
FIG. 22 illustrates an in-the-ear part (unit) of a receiver-in-the-ear hearing aid according to an embodiment of the disclosure.

Now referring to FIG. 22 which illustrates an in-the-ear part (unit) of a receiver-in-the-ear hearing aid according to an embodiment of the disclosure.

In particular, FIG. 22 illustrates another view of the in-the-ear hearing aid device 11 shown in FIG. 21.

Figure 23:
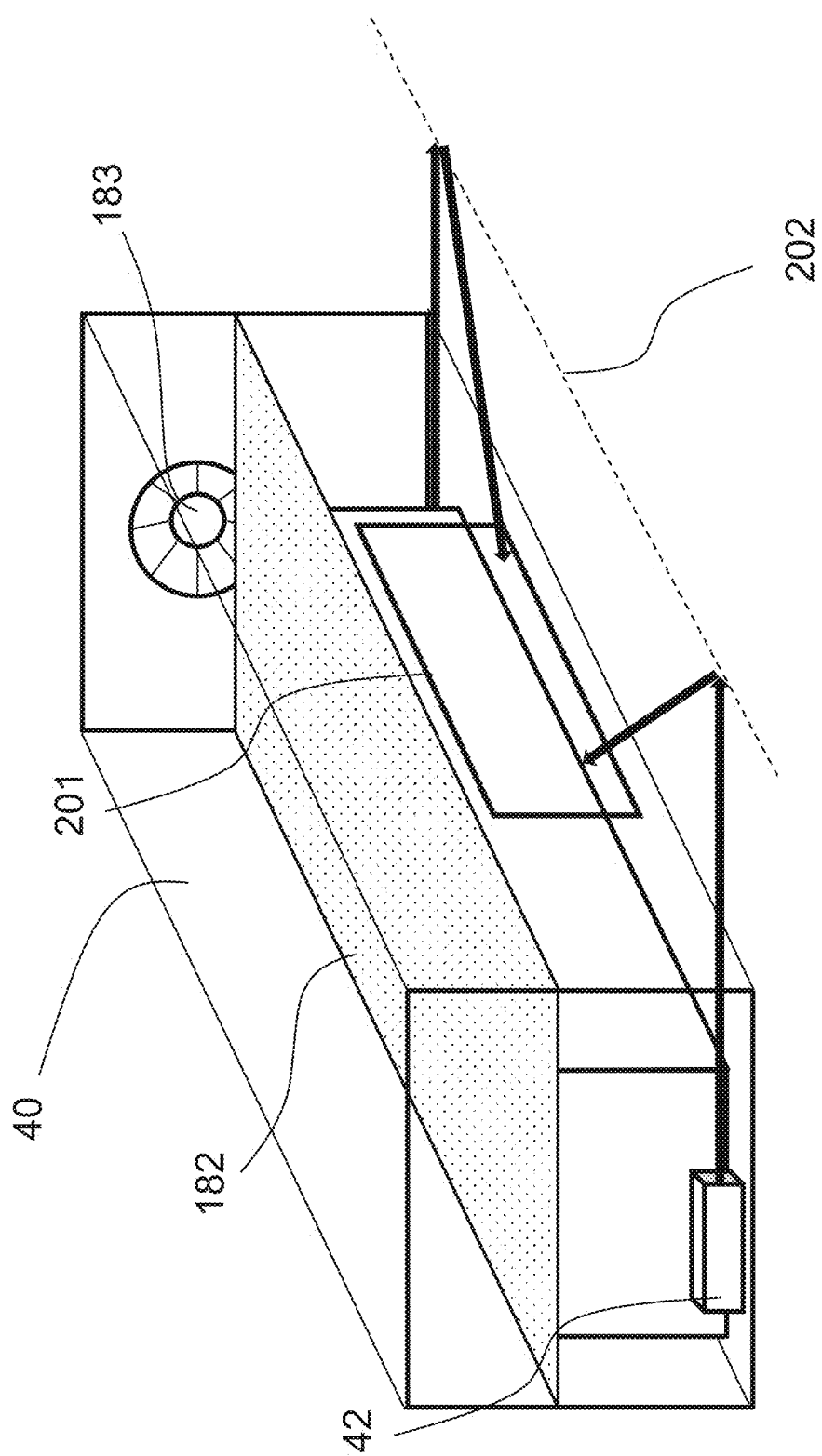
FIG. 23 illustrates an in-the-ear part (unit) of a receiver-in-the-ear hearing aid according to an embodiment of the disclosure.

Now referring to FIG. 23 which illustrates an in-the-ear part (unit) of a receiver-in-the-ear hearing aid according to an embodiment of the disclosure.

As can be seen in FIG. 23, more than one sensors (or active electronic components) 42 may be placed within the upper transducer air volume.

For specific measurement applications, at least an emitting device and a receiving device are necessary.

However, the output of the at least one emitting device may disturb the receiving performance of the at least one receiving device. Accordingly, in the example illustrated in FIG. 23, a line of sight between the at least one emitting device and the at least one receiving device is shielded. The line of sight may be shielded by a portion of the electro-acoustic transducer, e.g. the group of elements 191 or the respective housing thereof. However, the shielding may be effected by other elements as well, for example by any of the additional sensors (or active electronic components) 42. The shielding is not limited to the lower transducer air volume. Namely, such shielding can also be effected in case the elements necessary for measurement are arranged within the upper transducer air volume. Further, one of the at least one emitting device and the at least one receiving device may be placed within the upper transducer air volume while the other of the at least one emitting device and the at least one receiving device is placed within the lower transducer air volume. In such way, the shielding may be effected by the separation part 182.

In the example shown in FIG. 23, two emitting devices 42 (e.g. light emitting diodes) and one receiving device 201 (e.g. light receiving element) are arranged in the lower transducer air volume to measure any characteristic of measurement object 202 e.g. using light (indicated by arrows in FIG. 20) reflected from the measurement object 202. The receiving device 201 may be made large by providing the same on a surface or part of the capsule. The measurement may be effected through openings or specifically featured walls of the capsule. Measurement applications are not limited to such arrangement.

Figure 24:
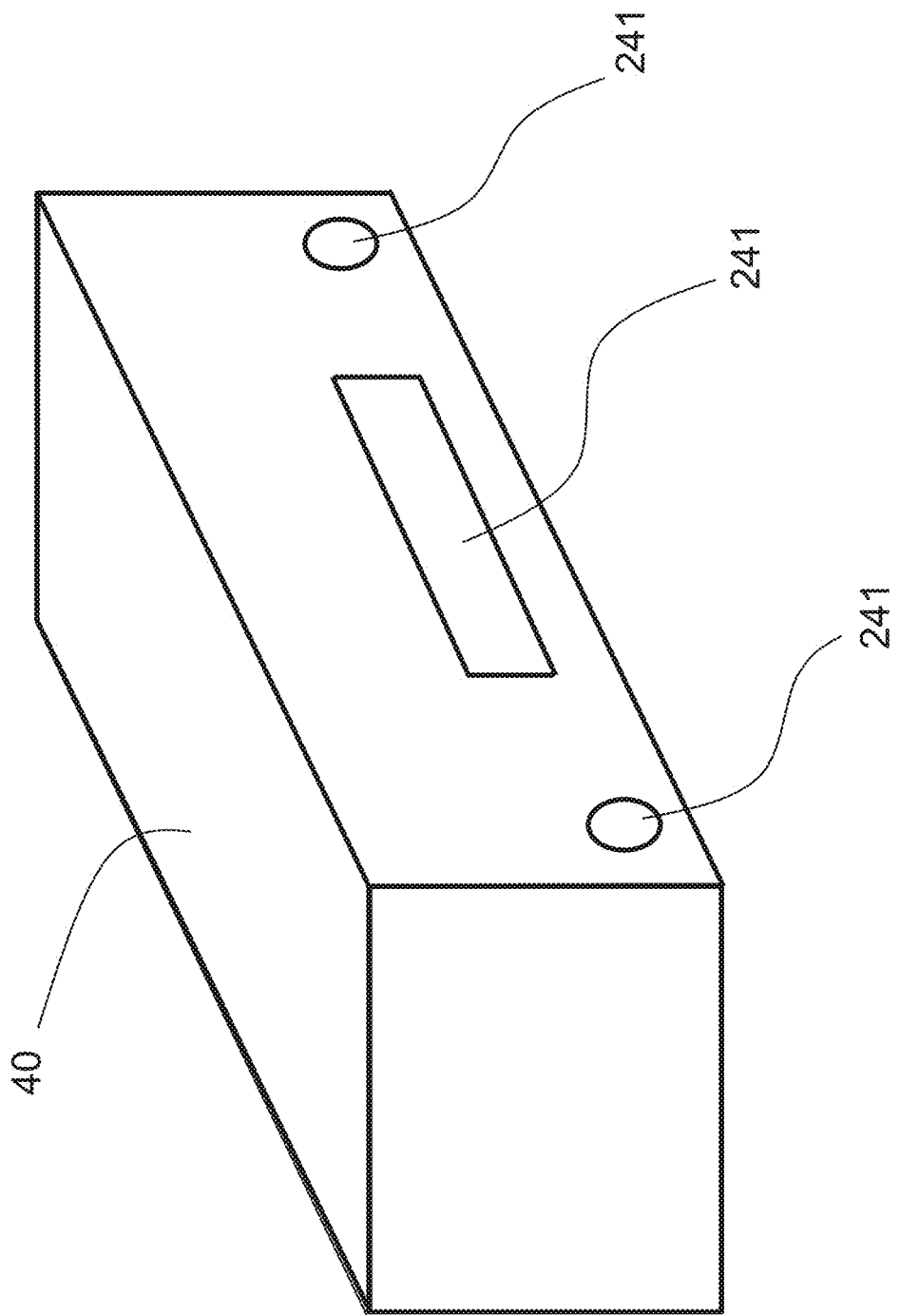
FIG. 24 illustrates an in-the-ear part (unit) of a receiver-in-the-ear hearing aid according to an embodiment of the disclosure.

Now referring to FIG. 24 which illustrates an in-the-ear part (unit) of a receiver-in-the-ear hearing aid according to an embodiment of the disclosure.

In particular, FIG. 24 illustrates openings or specifically featured walls of the capsule 40 of the in-the-ear hearing aid device 11.

As can be seen in FIG. 24, the capsule 40 may comprise openings 241 corresponding to intended effective directions/ranges of the emitting devices and receiving devices arranged within the transducer air volume 43 enclosed by the capsule 40.

In order to protect the interior from impacts from the outside of the in-the-ear hearing aid device 11, instead of providing openings 241 in the capsule 40, the regions of (a respective wall of) the capsule may have a characteristic allowing the intended effect of the emitting devices and receiving devices arranged within the transducer air volume 43. For example, the capsule 40 may be provided with optically transparent regions 241.

The regions 241 of the capsule having the characteristic allowing the intended effect of the emitting devices and receiving devices arranged within the transducer air volume 43 may have a function to shield the interior of the capsule (e.g. coils and magnets of the electro-acoustic transducer) from electromagnetic waves of a specified wave range to avoid any disturbance of the acoustic performance of the electro-acoustic transducer. For example, the regions 241 may be designed such that electromagnetic waves having a frequency lower than a predetermined noise shielding frequency are prevented from entering the capsule through the regions, while e.g. light is still allowed to exit and enter the capsule via the regions 241.

As is illustrated in FIG. 24, such regions 241 may be provided by optically transparent material.

Figure 25:
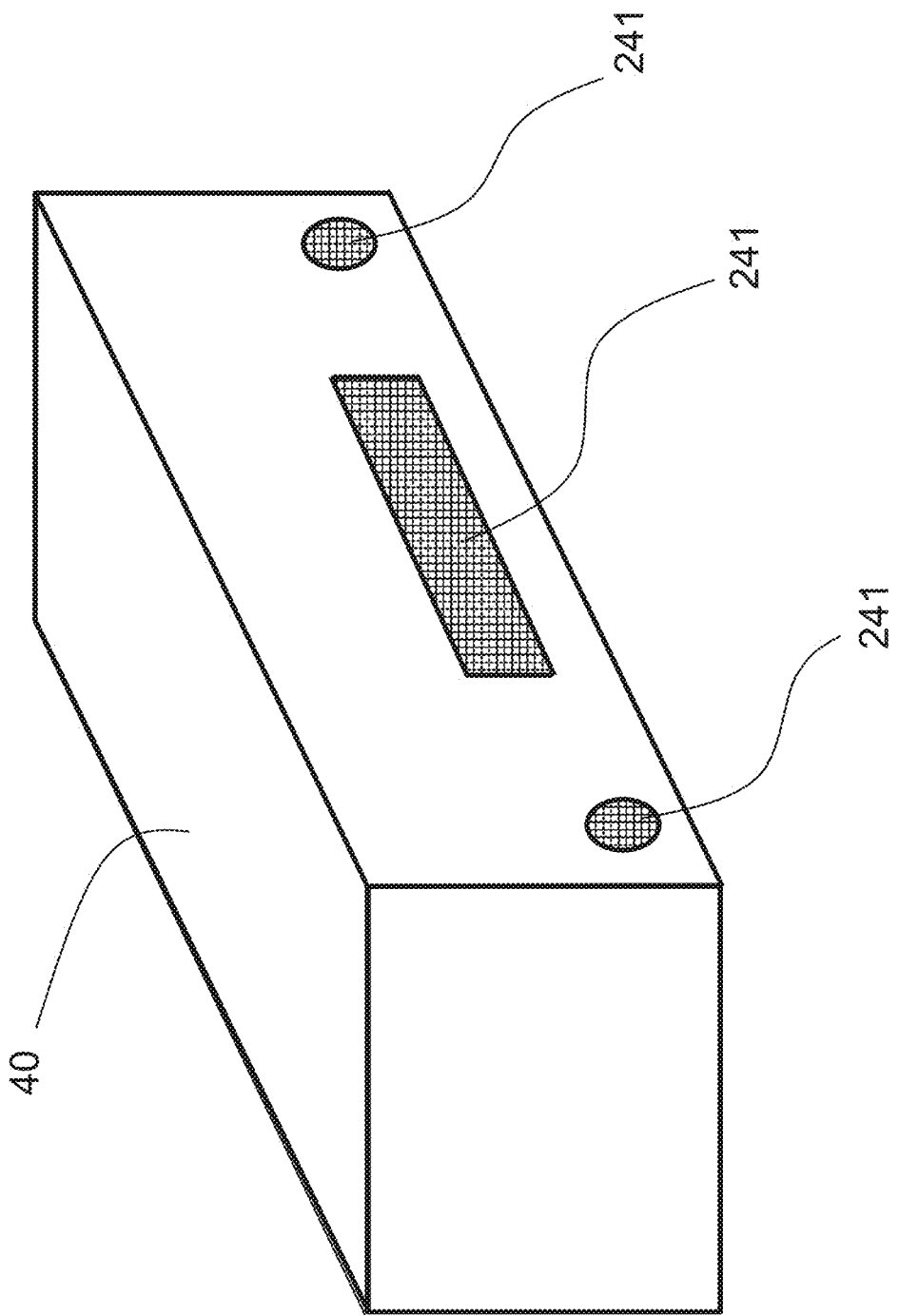
FIG. 25 illustrates an in-the-ear part (unit) of a receiver-in-the-ear hearing aid according to an embodiment of the disclosure.

Now referring to FIG. 25 which illustrates an in-the-ear part (unit) of a receiver-in-the-ear hearing aid according to an embodiment of the disclosure.

As is illustrated in FIG. 25, such regions 241 may be provided by a mesh ensuring that electromagnetic waves having a frequency lower than a predetermined noise shielding, frequency are prevented from entering the capsule through the regions, while e.g. light is still allowed to exit and enter the capsule via the regions 241.

Figure 26:
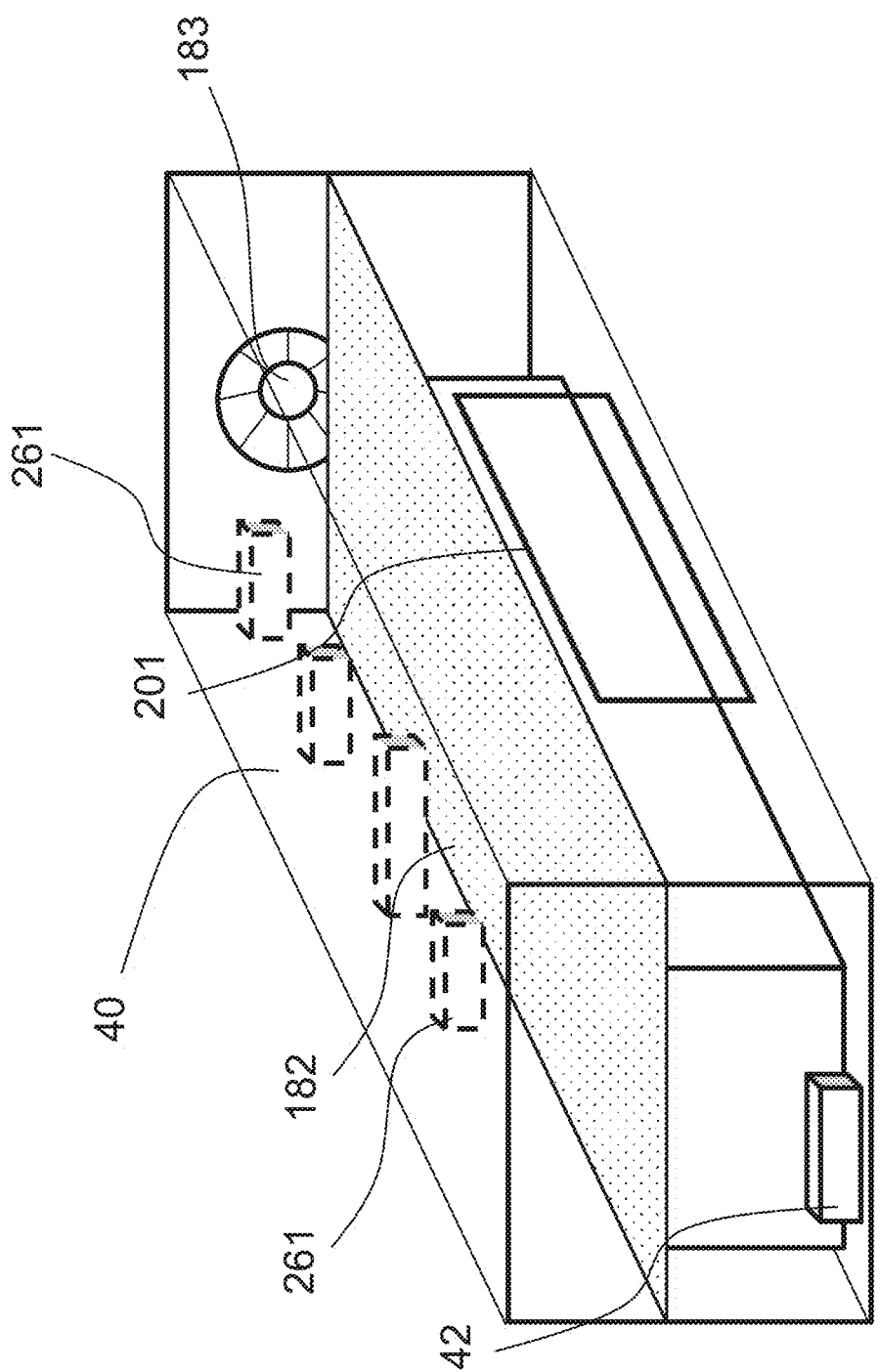
FIG. 26 illustrates an in-the-ear part (unit) of a receiver-in-the-ear hearing aid according to an embodiment of the disclosure.

Now referring to FIG. 26 which illustrates an in-the-ear part (unit) of a receiver-in-the-ear hearing aid according to an embodiment of the disclosure.

As is illustrated in FIG. 26, additional elements may be distributed over both of the upper and lower (first and second) transducer air volume.

For example, while a measurement arrangement as explained with reference to FIG. 23 is provided within the lower transducer air volume, additional sensors and/or active electronic components 261 may be provided within the upper transducer air volume. The positioning of the measurement arrangement additional sensors and/or active electronic components 261 is however not limited to the example shown in FIG. 26.

If sensors/components are placed in both volumes (i.e. within the upper and lower transducer air volumes), the wiring between the components/sensors in both volumes may go through the separation part 182 (e.g. the diaphragm) or may be guided by an outside surface of the capsule. For example, a wire may exit the second volume through a wall of the capsule and then enter the first volume through a wall of the capsule. The wire outside the capsule may be guided via a guiding portion (tube or any kind of a hollow portion). The guiding portion may be mounted to the outside surface of the capsule or may be built into the wall of the capsule. The guiding portion may also be placed on the inside of the capsule going through separation part 182 (e.g. the diaphragm).

Now referring to FIG. 27 which illustrates a receiver-in-the-ear hearing aid in a communication scenario according to an embodiment of the disclosure.

As can be seen in FIG. 27, the receiver-in-the-ear hearing aid shown in FIG. 1 and further specified in relation to any of the foregoing Figures can be configured for communication (preferably wireless communication) with an external device 271.

The external device may for example be a Smartphone. A communication part of the receiver-in-the-ear hearing aid which is configured for communication with an external device may be provided, for example, in in-the-ear hearing aid device 11 or in the behind-the-ear hearing aid device 13 and may comprise, for example, a transmission and/or reception controlling circuitry and an antenna. While it is preferable to provide the communication part in the behind-the-ear hearing aid device 13 for keeping the in-the-ear hearing aid device 11 as small as possible, it is also possible to integrate the communication part with a sensor (e.g. the temperature sensor) provided in the in-the-ear hearing aid device 11. At least, the sensor (e.g. the temperature sensor) provided in the in-the-ear hearing aid device 11 is connected to the communication part.

By means of the communication part, the sensor (e.g. the temperature sensor) may be connected with the external device e.g. via wireless local area network (WLAN), Bluetooth low energy, Nearlink or other techniques and can share the temperature (in general, the measurement result) wirelessly to the external device. The connection between the sensor and/or the active electronic component and the external device may be initiated by the sensor and/or the active electronic component or by the external device.

The connection may be established by a signal processor arranged within the transducer air volume or in a hearing aid device based on a security signal provided by a security mean. The security mean may receive a request signal from the external device, wherein the request signal includes an identification code identifying the external device. The security mean may accept the request signal if the identification (ID) code is identical to a stored ID code in a volatile memory/none-volatile memory being arranged within the transducer air volume or a hearing aid device.

The thus shared measurement result may be transmitted via the internet to other devices, and/or may be displayed on the external device or on separate devices.

The measurement results may thus also be shared with known online or offline health or fitness applications provided by the external device or any server connected to the internet. For example, the measurement results may be shared with a (an online) public health system.

The measurement results can thus also be shared with relatives or with the medical professionals, e.g. a doctor.

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In an aspect, a data processing system comprising a processor adapted to execute the computer program for causing the processor to perform at least some (such as a majority or all) of the steps of the method described above and in the claims.

Figure 28:
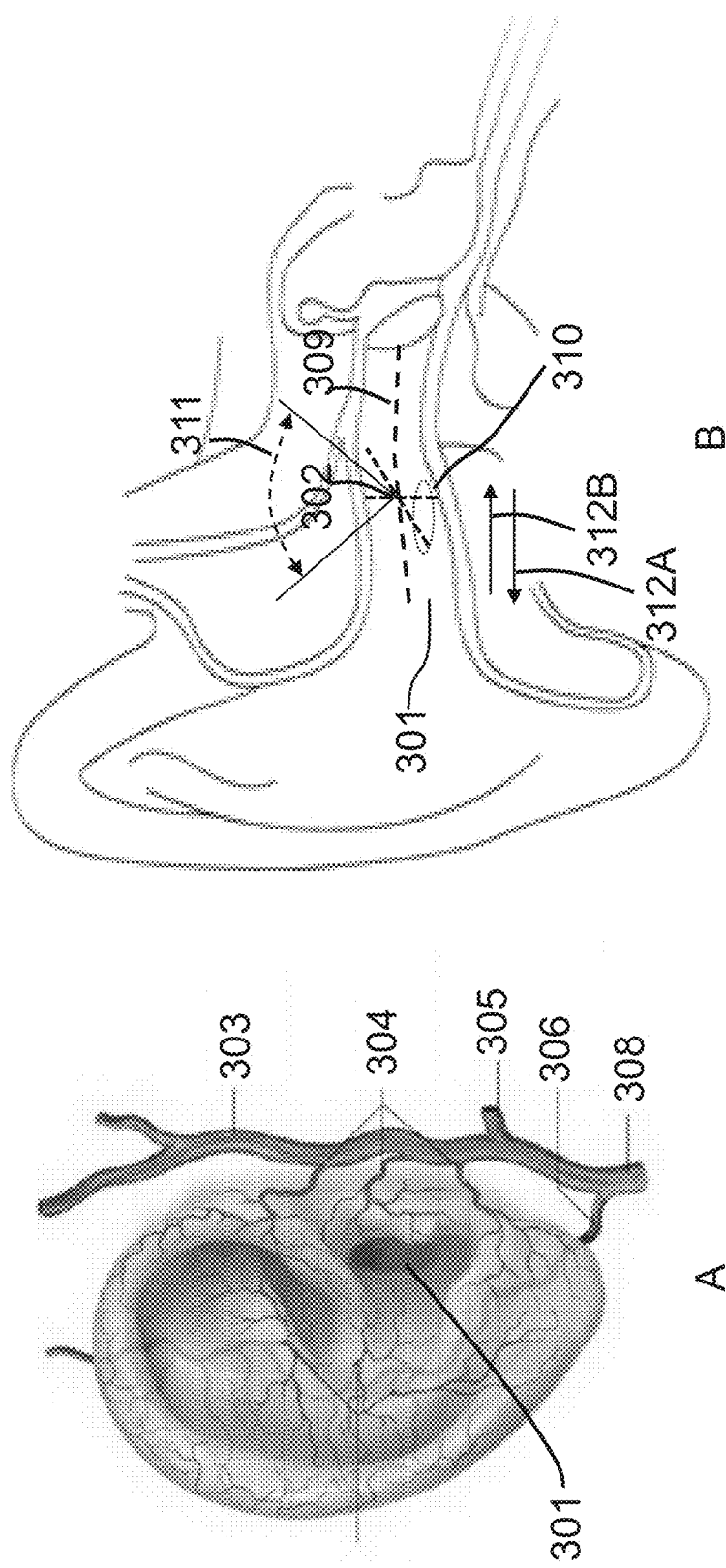
FIG. 28 illustrates an ear canal and main arteries within a head of a user.

FIG. 28A illustrates the main arteries located in vicinity to an ear canal 301, the so-called Superficial temporal artery 303, Anterior auricular artery 304, Maxillary artery 305, Posterior auricular artery 306, Internal carotid artery 307 (not shown in the figure) and External carotid artery 308.

FIG. 28B illustrates the ear canal 301 having a longitudinal axis 309 extending from the opening of the ear canal 301 towards 312B the eardrum of the ear canal 301. The ear canal 301 has a transverse axis 310 extending orthogonal or partially orthogonal to the longitudinal axis 309. Where the longitudinal axis 309 and the transverse axis 310 intersects each other within the ear canal 301 defines a centre point 302 in the ear canal 301. Each main artery (304, 305, 306, 307, 308) is positioned relative to the ear canal 301 as following;

External carotid artery 308 or Internal carotid artery 307
is positioned below the ear canal 301 and within a line of sight angle 311 defined from the centre point 302 in the ear canal 301 directed along the transverse axis 310, and where the line of sight angle 311 is between 45° and 120°, between 90° and 110°, and between 35° and 160°, Internal carotid artery 307 is partly positioned below and above the ear canal 301 and within a line of sight angle 311 defined from the centre point 302 in the ear canal 301 directed along the transverse axis 310 or the longitudinal axis 309 inwards 312B the ear canal 301, and where the line of sight angle 311 is between 45° and 120°, between 90° and 110°, and between 35° and 160°, Posterior auricular artery 306 is positioned below the ear canal 301 and within a line of angle 311 defined from the centre point 302 in the ear canal 301 directed along the transverse axis 310, and where the line of sight angle 311 is between 10° and 45°, between 5° and 25°, and between 90° and 110°, Superficial temporal artery 303 is positioned above the ear canal 301 and within a line of sight angle 311 defined from the centre point 302 in the ear canal 301 directed along the transverse axis 310 and in a forward direction towards a face of the user, and where the line of sight angle 311 is between 10° and 45°, between 5° and 25°, and between 90° and 110°, and Anterior auricular artery 304 and Maxillary artery 305, are positioned within a line of sight angle 311 defined from the centre point 302 in the ear canal 301 directed along the transverse axis 310 and in a forward direction towards a face of the user, and where the line of sight angle 311 is between 10° and 45°, between 5° and 25°, and between 90° and 110°.

FIG. 29 illustrates different positions of the at least one sensor 22, 42 and/or the at one active electronic component 22, 42 within the transducer air volume 43. The capsule 40 or the in-the-ear hearing aid device 11 has a first end 314 and a second end 315, wherein the outlet opening or inlet opening 183 is positioned closest to the first end 314. FIG. 29A illustrates said at least one sensor 22, 42 and said at least one active electronic component arranged within the transducer air volume 43 and on an inner surface of a wall of the capsule 11, 40, or on an outer surface of a wall of the capsule 11, 40 where the wiring to the at least one sensor 22, 42 and/or the at least one active electronic component 22, 42 enters the transducer air volume 43. FIG. 29B illustrates said at least one sensor 22, 42 and said at least one active electronic component 22, 42 arranged closest to the first end 314. FIG. 29C illustrates a further example, where said at least one sensor 22, 42 and two active electronic components 22, 42 are arranged closest to the first end 314.

The at least one sensor 22, 42 and/or the at least one active electronic component 22, 42 may be placed partly within the transducer air volume 43 and on an inner surface of a wall of the capsule 11, 40, or on an outer surface of a wall of the capsule 11, 40 where the wiring to the at least one sensor 22, 42 and/or the at least one active electronic component 22, 42 enters the transducer air volume 43.

FIG. 30 illustrates different positions of the at least one sensor 22, 42 and/or the at one active electronic component 22, 42 within the transducer air volume 43. Both the inner surface of the wall and the outer surface of the wall of the capsule 11, 40 may have a corner and an edge. FIG. 30A illustrates the at least one sensor 22, 42 and/or the at least one active electronic component 22, 42 arranged at the corner or at the edge of the capsule 11, 40, thereby, the sensor and/or the active electronic component 22, 42 are placed near the skin 313 of the ear canal 301.

FIG. 30B illustrates a centre axis 316 of a wall of the capsule 11, 40. The at least one sensor 22, 42 and/or the at least one active electronic component 22, 42 may be arranged around the centre axis 316.

Figure 31:
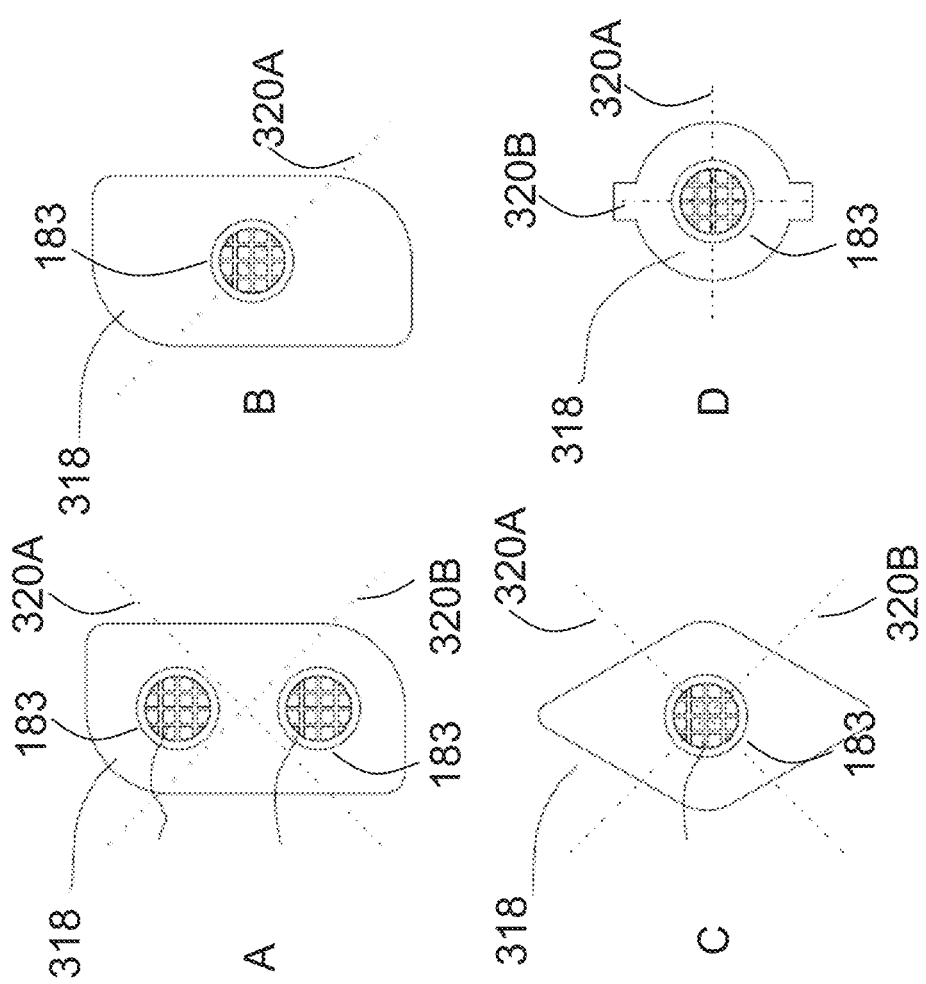
FIG. 31 illustrates a mechanical interface of the capsule or the in-the-ear hearing aid device.

FIG. 31 illustrates a mechanical interface 318 of the capsule 40 or the in-the-ear hearing aid device 11. The inlet opening 183 or the outlet opening 183 may have a mechanical interface 318 configured to receive an earpiece 11a. Normally, the mechanical interface 183, 318 is symmetric in all directions, i.e. a user of the in-the-ear hearing aid device 40 has the possibility of mounting the earpiece 11a to the mechanical interface 318 such that the at least one sensor 22, 42 and/or the at least one active electronic component 22, 42 is positioned wrongly within the ear canal 301 of the user.

FIG. 31A illustrate the mechanical interface 318 having two symmetrical axes 320A, 320 B, wherein the number of possible angles for mounting the earpiece 11a to the mechanical interface 318 has reduced to one or two ways, respectively. The shape of the mechanical interface 318 provides the two symmetrical axes 320A, 320B. Thereby, the usability has improved because the possibility of placing the earpiece 11a such that the at least one sensor 22, 42 and/or the at least one active electronic component 22, 42 is arranged wrongly within the ear canal 301 has reduced significantly.

Furthermore, FIG. 31A illustrates the capsule 11, 40 having both the outlet opening 183 and the inlet opening 183.

FIG. 31B illustrates the mechanical interface 318 with one symmetrical axis 320A.

FIG. 31C illustrates another example of the mechanical interface 318 with two symmetrical axes 320A and 320B.

FIG. 31D illustrates another example of the mechanical interface 318 with two symmetrical axes 320A and 320B.

Figure 32:
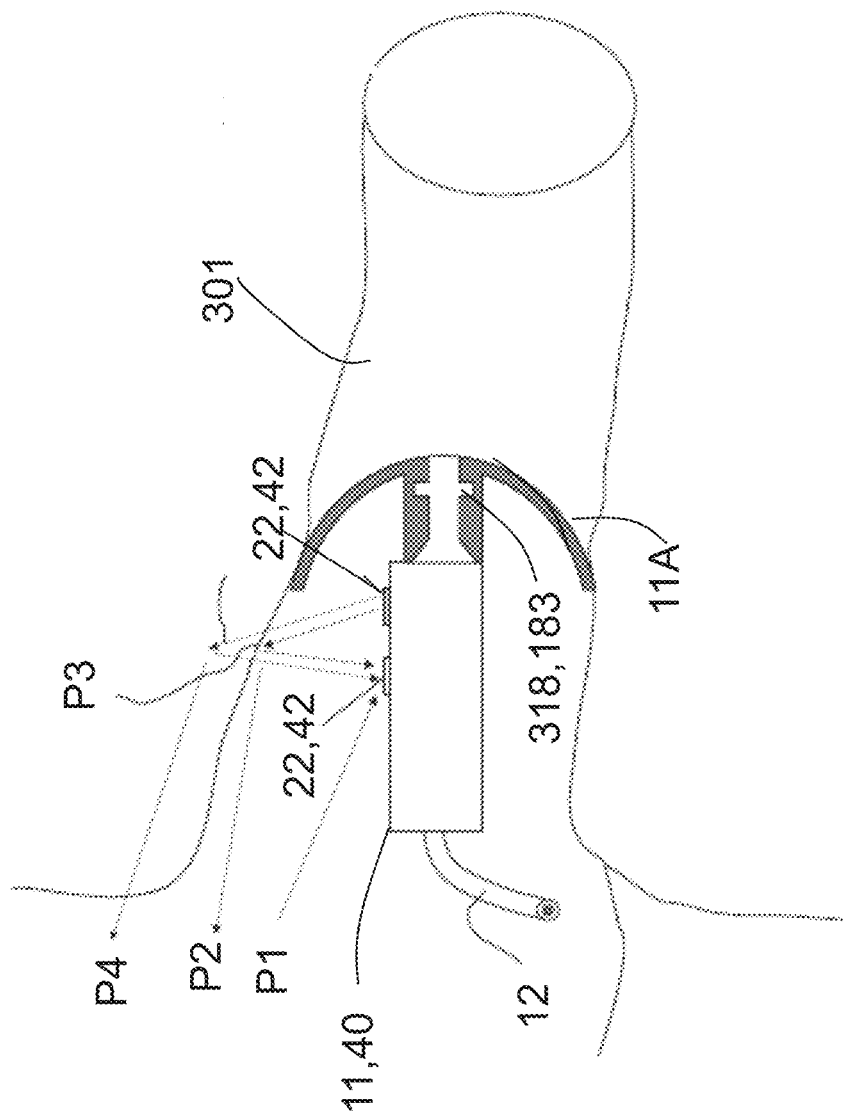
FIG. 32 illustrates an in-the-ear hearing aid device comprising an optical system.

FIG. 32 illustrates for the in-the-ear hearing aid device 11 comprising an optical system including the at least one sensor 22, 42 which may be a photodetector, and the at least one active electronic component 22, 42 which may be one or more light emitting diodes. Several problems may occur in the optical system, such as light from outside may ruin the measurement of the at least one sensor P1, light from the light emitting diode(s) may be seen from outside when the user is in darkness P2, reflections from the skin surface 313 of the ear canal 301, P3, and light from outside exiting through the skin of the ear canal 301 and in to the at least one sensor P4.

Figure 33:
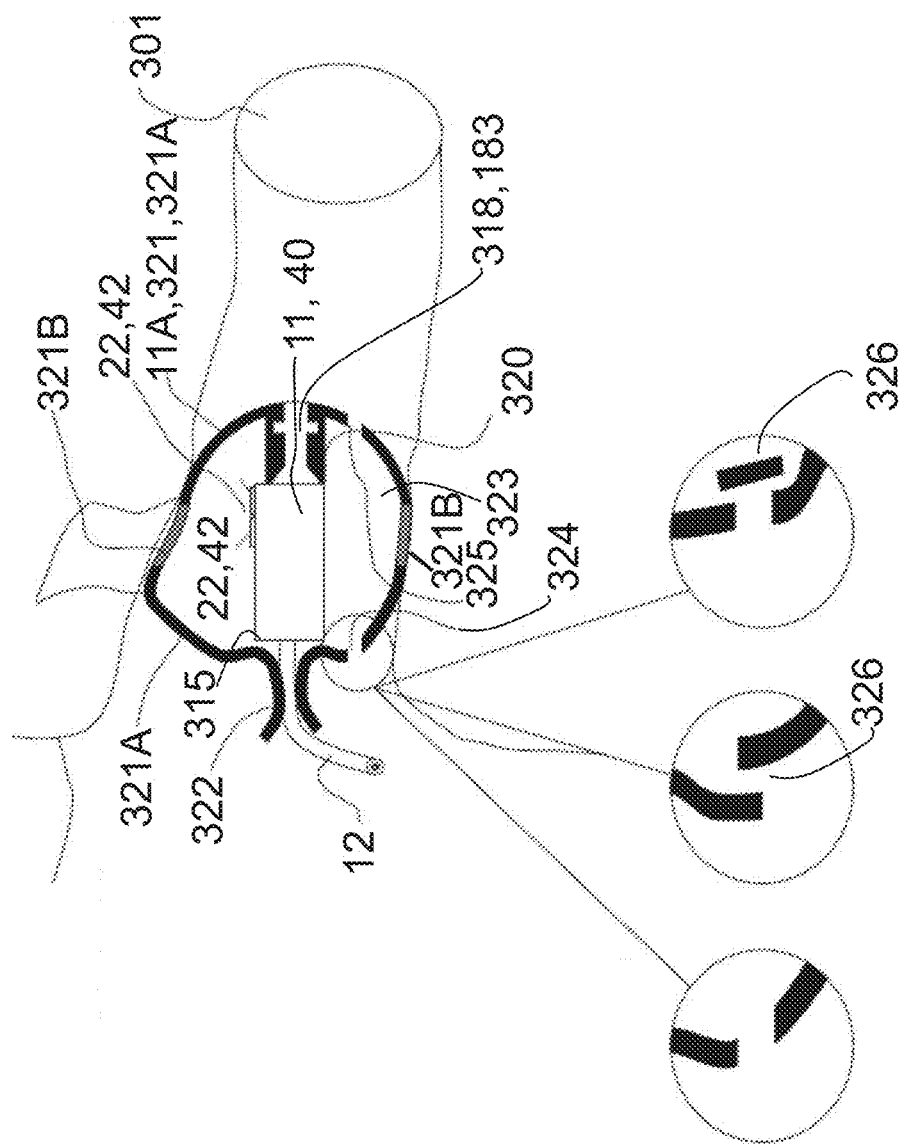
FIG. 33 illustrates the in-the-ear hearing aid device with an earpiece.

FIG. 33 illustrates the in-the-ear hearing aid device 11 with an earpiece 11A. The earpiece 11A comprises a receiving mean 320 configured to be attached to the mechanical interface 318 of the in-the-ear hearing aid device 11. The earpiece 11A comprises a flexible portion 321 configured to encircle the in-the-ear hearing aid device 11, and the earpiece 11A comprises a sealing portion 322 connected to the flexible portion 321, wherein the sealing portion 322 is configured to seal around the connection tube 12 or around the second end 315 of the capsule 40 or the in-the-ear hearing aid device 11. The sealing portion 322 is configured to prevent light from the surroundings to reach the sensor 22, 42.

The flexible portion 321 may be made of a flexible material, such as a foam, memory foam, silicon or any kind of a flexible material suitable for an-in-the-ear hearing aid device 11.

The flexible portion 321 may comprise a first section 321A being coloured such that any light is prevented from entering a volume 323 encircled by the earpiece 11A. The colour of the first section 321A may be black. The flexible portion 321 may comprise a second section 321B being coloured such that the light emitted from a light emitting diode (LED) 22,42, i.e. the at least one active electronic component 22, 42, is able to be transmitted through the earpiece 11A and to the body of the user. Furthermore, the second section 321B is further configured to allow physical information and/or biometric signals generated based on the light emitted by the LED 22, 42 to pass through the earpiece 11A and to reach the sensor 22, 42.

The earpiece 11A may comprise a first vent 324 and a second vent 325, where the first vent 324 has a line of sight directed outwards, and the second vent 325 has a line of sight directed inwards. The vents 324, 325 are configured to reduce or eliminate occlusion effect.

When the earpiece 11A is in the ear canal 301, the first vent 324 is exposed to unwanted light since it is pointing outwards, and the second vent 325 is not exposed to unwanted light, for example from the sun, because it is pointing inwards, e.g. towards the tympanic membrane of the ear canal 301. Therefore, if the first vent 324 is a straight hole then unwanted light from the sun will not be prevented from entering the volume 323 enclosed by the flexible portion 321. Therefore, the first vent 324 may have an obstacle 326 configured to prevent light from entering the first vent.

Figure 34:
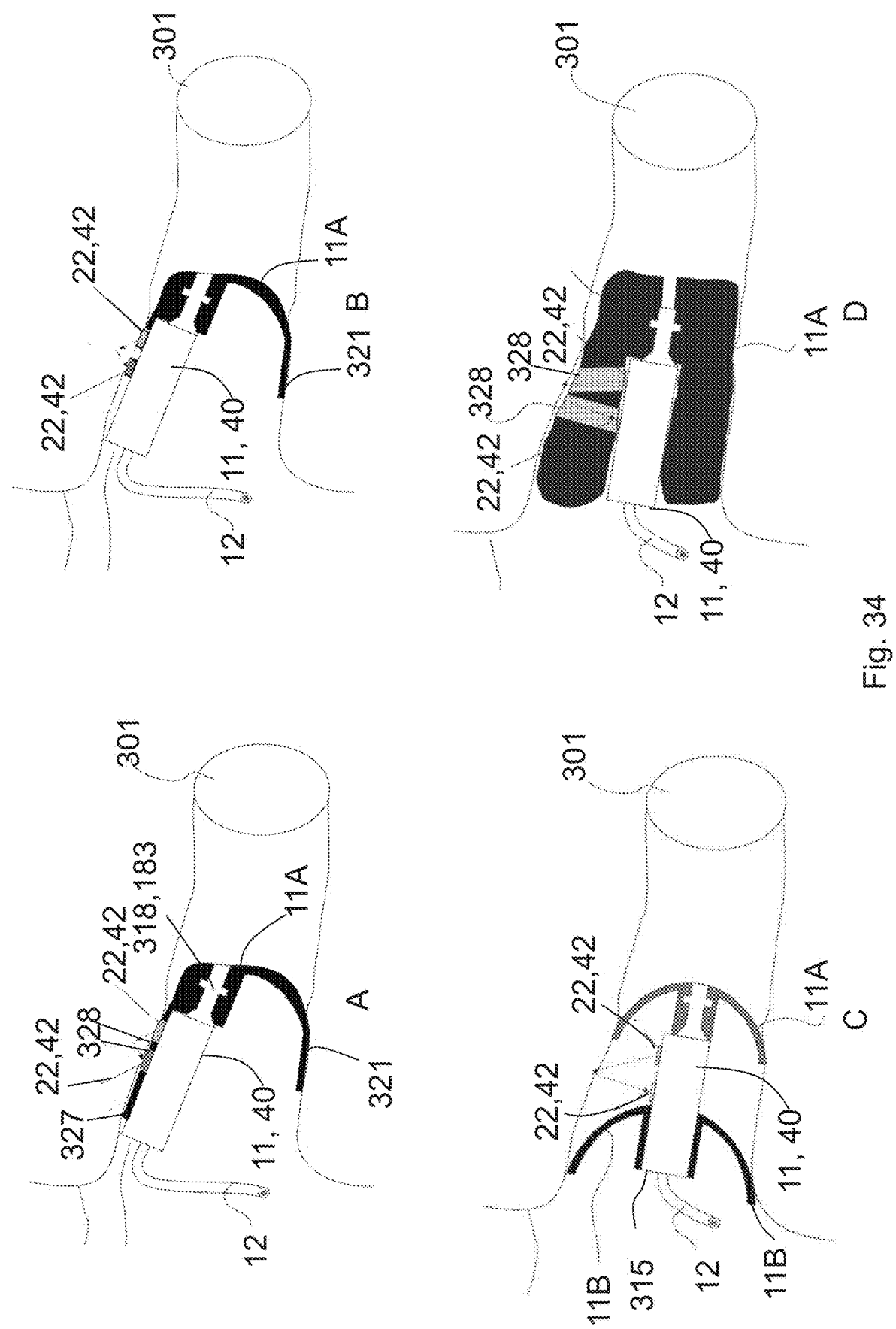
FIG. 34 illustrates different examples of an earpiece.

FIG. 34 illustrates different examples of an earpiece 11A. FIG. 34A illustrates an earpiece attached to the mechanical interface 318 of the in-the-ear hearing aid device 11 or the capsule 40 of the electro-acoustic transducer. The earpiece 11A comprises a flexible portion 321 configured to provide a force to the skin 313 of the ear canal 301, and thereby, forcing the capsule 40 or the in-the-ear hearing aid device 11 towards the skin 313 of the ear canal 301. The distance between the at least one sensor 22, 42 and/or the at least one active electronic component 22, 42 is minimized.

A surface of the capsule 40 which the line of sight of the at least one sensor 22, 42 and/or the at least one active electronic component 22, 42 is directed through is arranged close to the skin 313 of the ear canal 301 because of the flexible portion 321. The flexible portion 321 may be shaped as a half dome. In this example, the at least one sensor 22, 42 and/or the at least one active electronic component 22, 42 is positioned within the transducer air volume 43 and closest to the surface. The earpiece 11A may further comprise a second portion 327 which is applied on to the surface of the capsule 40. The second portion 327 is arranged such that a distance between the surface and the skin 313 of the ear canal 301 is about equal to a thickness of the second portion 327. The second portion 327 may comprise at least two guiding means 328, 328 configured to guide the signals being transmitted by the at least one active electronic component 22, 42 and received by the at least one sensor 22, 42. In FIG. 34B, the earpiece comprises the flexible portion as described in FIG. 34A, but does not comprise the second portion. In this example, the at least one sensor and/or the at least one active electronic component 22, 42 is arranged outside the transducer air volume but a signal processor or wire connected to the sensor 22, 42 and/or the component 22, 42 is arranged within the transducer air volume 43. At least one side of the at least one sensor 22/42 and/or the at least one active electronic component 22, 42 is coated with a non-transparent material configured to prevent unwanted light to interfere with the physiological information or biometric signal generated by the at least one sensor 22, 42.

FIG. 34C illustrates an earpiece 11A which is dome shaped and provided to the mechanical interface 318. A second earpiece 11B is arranged closest to the second end 315, wherein the second earpiece 11B is configured to prevent unwanted light to interfere with the physiological information or biometric signal generated by the at least one sensor 22, 42.

In one example the first earpiece may be transparent while the second earpiece may not be transparent.

FIG. 34D illustrates an earpiece 11A which partly encloses the capsule 40 or the in-the-ear hearing aid device 11. The earpiece 11A may be made out of a foam material, and wherein the earpiece comprises guiding means.

Figure 35:
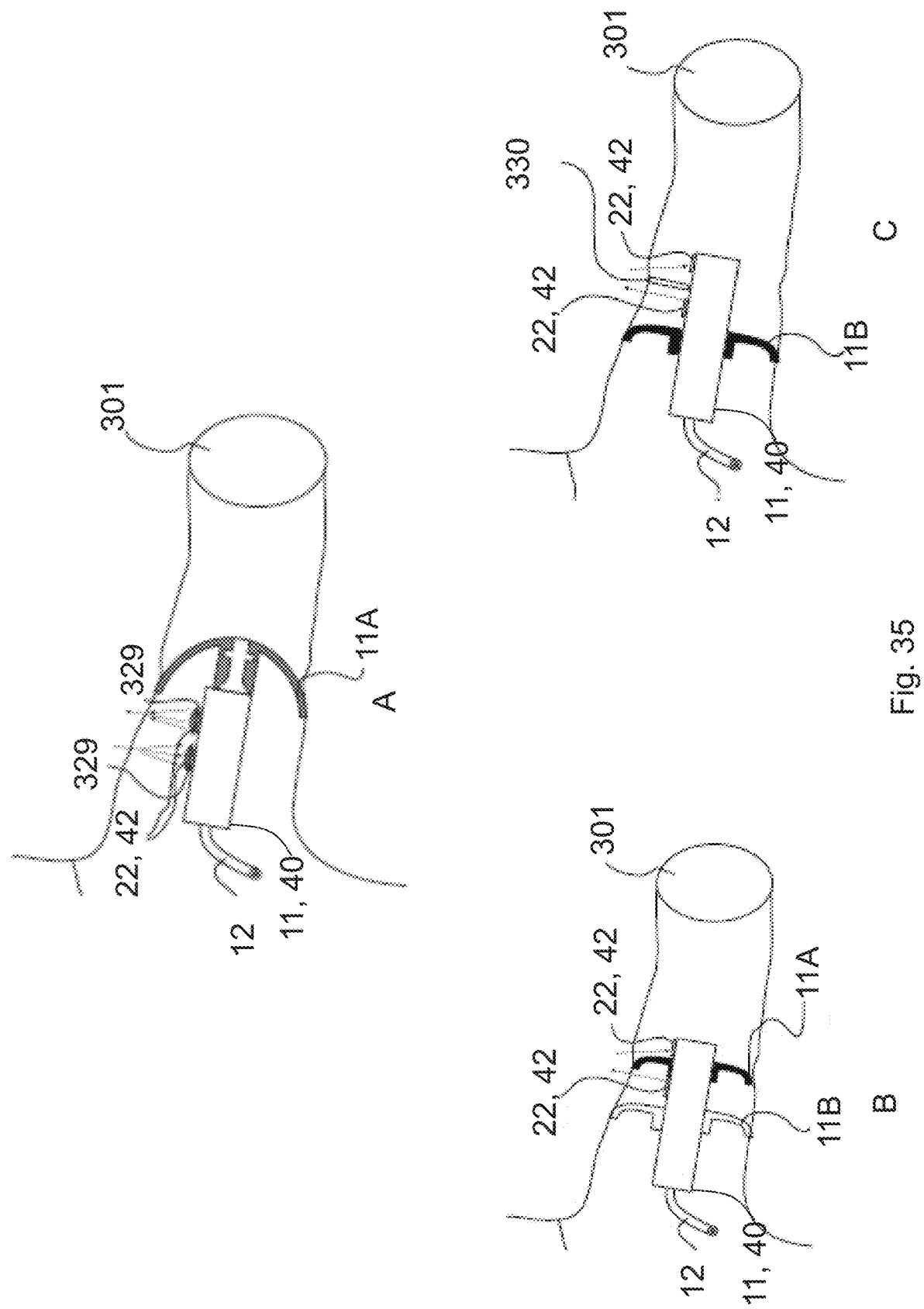
FIG. 35 illustrates further different examples of an earpiece.

FIG. 35 illustrates different examples of an earpiece 11A. FIG. 35A illustrates the earpiece being a regular dome shaped and wherein a lens 329 is provided in front of the at least one sensor 22, 42 and/or the at least one active electronic component 22, 42. The lens 329 is configured to optically focus the light being emitted by the at least one active electronic component 22, 42 and/or the light being received by the at least one sensor 22, 42.

FIG. 35B illustrates the capsule 40 and/or the in-the-hearing aid device 11 with the earpiece 11A and another earpiece 11B, wherein at least one sensor 22, 42 and/or the at least one active electronic component 22, 42 is positioned between the two earpieces 11A, 11B, and wherein at least one sensor 22, 42 and/or the at least one active electronic component 22, 42 is positioned on an opposite side of the earpiece 11A. In FIG. 35C, the earpiece is replaced with a separator 330 configured to separate the at least one sensor 22, 42 and/or the at least one active electronic component 22, 42.

Figure 36:
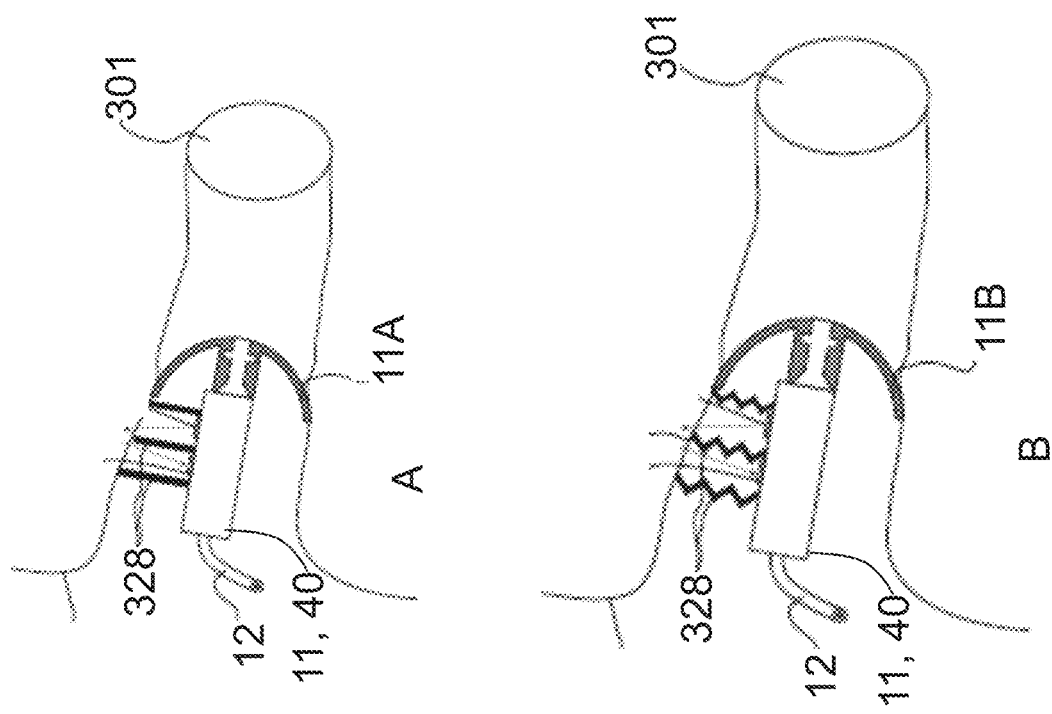
FIG. 36 illustrates different examples of guiding means.

FIG. 36 illustrates different examples of guiding means 328. In FIG. 36A, the guiding means 328 are formed by skirts guiding the light emitted by the at least one active electronic component 22, 42 and forcing the light to enter the skin 313 of the ear canal 301. In FIG. 36B, the guiding means 328 are formed by soft tubes.

The guiding means may be made of a non-transparent material.

Figure 37:
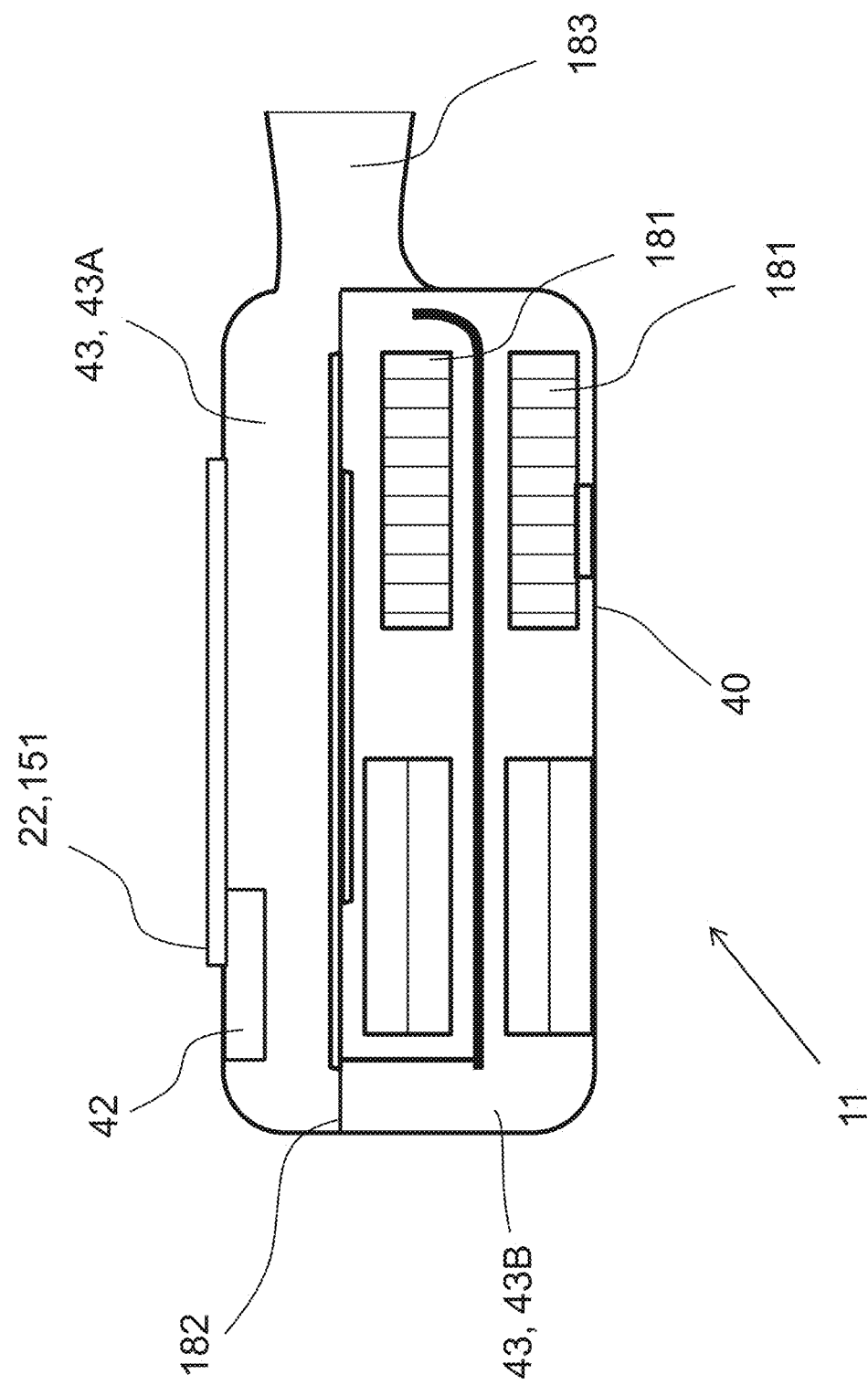
FIG. 37 illustrates an in-the-ear part (unit) of a receiver-in-the-ear hearing aid according to an embodiment of the disclosure.

FIG. 37 illustrates the in-the-ear hearing aid device 11, wherein an EEG monitoring system 42 is arranged partly in the transducer air volume 43, i.e. in the first transducer air volume 43A in this example. The at least sensor 22, 151, which in this example comprises one or more electrodes, is arranged outside and on the capsule 40. An EEG signal processor is part of the EEG monitoring system.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An in-the-ear hearing aid device, comprising
at least one electro-acoustic transducer, and
at least one sensor or at least one active electronic component,
wherein said at least one electro-acoustic transducer comprises a capsule enclosing a transducer sound active part and a transducer air volume, wherein said transducer sound active part comprises at least one of a membrane, a diaphragm, an electromagnetic mechanism, and a sound vibrating unit, and said transducer air volume is air volume which is enclosed by said capsule and which is in fluid-connection with said transducer sound active part, wherein
at least a portion of said at least one sensor or of said at least one active electronic component is provided within said capsule and said transducer air volume,
said capsule forms a housing of said at least one electro-acoustic transducer, and
said capsule includes a connection tube of the in-the-ear hearing aid device, wherein a passage through said connection tube is in fluid-connection with an opening in said housing of said at least one electro-acoustic transducer, wherein said opening is in fluid-connection with said transducer sound active part.

2. The in-the-ear hearing aid device according to claim 1, wherein at least part of said capsule forms an exterior housing of said in-the-ear hearing aid device defining an outer contour of said in-the-ear hearing aid device.

3. The in-the-ear hearing aid device according to claim 1, wherein said capsule includes a receiver outlet of the in-the-ear hearing aid device, wherein a passage through said receiver outlet is in fluid-connection with an outlet opening in said housing of said at least one electro-acoustic transducer, wherein said outlet opening is in fluid-connection with said transducer sound active part.

4. The in-the-ear hearing aid device according to claim 1, wherein said passage through said connection tube is in fluid-connection with an opening in a housing of a behind-the-ear hearing aid device.

5. An in-the-ear hearing aid device, comprising:
at least one electro-acoustic transducer, and
at least one sensor or at least one active electronic component,
wherein said at least one electro-acoustic transducer comprises a capsule enclosing a transducer sound active part and a transducer air volume, wherein said transducer sound active part comprises at least one of a membrane, a diaphragm, an electromagnetic mechanism, and a sound vibrating unit, and said transducer air volume is air volume which is enclosed by said capsule and which is in fluid-connection with said transducer sound active part, wherein
at least a portion of said at least one sensor or of said at least one active electronic component is provided within said capsule and said transducer air volume,
said capsule forms a housing of said at least one electro-acoustic transducer, and
said capsule includes a microphone inlet of the in-the-ear hearing aid device, wherein a passage through said microphone inlet is in fluid-connection with an inlet opening in said housing of said at least one electro-acoustic transducer, wherein said inlet opening is in fluid-connection with said transducer sound active part.

6. The in-the-ear hearing aid device according to claim 1, wherein said at least one electro-acoustic transducer is one of a microphone and a receiver.

7. The in-the-ear hearing aid device according to claim 1, wherein at least a portion of said at least one sensor and at least a portion of said at least one active electronic component or at least a portion of a first sensor and at least a portion of a second sensor are provided within said transducer air volume, and wherein a line of sight between said portion of said at least one sensor and said portion of said at least one active electronic component or said portion of said first sensor and said portion of said second sensor is shielded by a portion of said electro-acoustic transducer.

8. An in-the-ear hearing aid device, comprising:
at least one electro-acoustic transducer, and
at least one sensor or at least one active electronic component,
wherein said at least one electro-acoustic transducer comprises a capsule enclosing a transducer sound active part and a transducer air volume, wherein said transducer sound active part comprises at least one of a membrane, a diaphragm, an electromagnetic mechanism, and a sound vibrating unit, and said transducer air volume is air volume which is enclosed by said capsule and which is in fluid-connection with said transducer sound active part, wherein
at least a portion of said at least one sensor or of said at least one active electronic component is provided within said capsule and said transducer air volume,
said capsule forms a housing of said at least one electro-acoustic transducer, and
said capsule comprises at least one measurement opening, and said at least one measurement opening is provided with an electromagnetic filter configured to prevent electromagnetic waves having a frequency lower than a predetermined noise shielding frequency from entering said capsule through said at least one measurement opening.

9. The in-the-ear hearing aid device according to claim 8, wherein said electromagnetic filter comprises at least one of a mesh, an optically transparent material and/or said predetermined noise shielding frequency is anyone of not audible frequencies.

10. The in-the-ear hearing aid device according to claim 1, wherein said at least one sensor comprises at least one of a temperature sensing element, a light sensing element, a sound sensing element, a moisture sensing element, a blood oximetry sensor including at least two light emitting elements and a light sensing element, a blood pressure sensor, a blood sugar sensor, a pulse sensor, a hydration sensor, a galvanic skin response electrode, an electroencephalography electrode, and an electrooculography electrode, and/or said at least one active electronic component comprises at least one of a light emitting diode, a pre-processor, a digital sound processor, an amplifier, a pre-amplifier, an AD-converter, a DA-converter, a sensor processing circuitry, a sensor fusion circuitry, a digital speaker communication bus, a bus controller circuitry, a memory, and a microcontroller.

11. The in-the-ear hearing aid device according to claim 1, wherein said transducer air volume is separated by said transducer sound active part into a first transducer air volume and a second transducer air volume not in fluid-connection with said first transducer air volume, said first transducer air volume is larger in volume than said second transducer air volume, and said portion of said at least one sensor or of said at least one active electronic component is provided within said first transducer air volume.

12. The in-the-ear hearing aid device according to claim 11, wherein at least a portion of at least another sensor or of at least another active electronic component is provided within said second transducer air volume.

13. A hearing aid, comprising said in-the-ear hearing aid device according to claim 1, a behind-the-ear hearing aid device, and a coupling element configured to mechanically and/or electrically connect said in-the-ear hearing aid device and said behind-the-ear hearing aid device.

14. An electro-acoustic transducer, comprising at least one sensor or at least one active electronic component, a capsule enclosing a transducer sound active part and a transducer air volume, wherein said transducer sound active part comprises at least one of a membrane, a diaphragm, an electromagnetic mechanism, and a sound vibrating unit, wherein said transducer air volume is air volume which is enclosed by said capsule and which is in fluid-connection with said transducer sound active part, and wherein at least a portion of said at least one sensor or of said at least one active electronic component is provided within said capsule and said transducer air volume, wherein
  said capsule forms a housing of said electro-acoustic transducer, and
  said capsule includes a connection tube of the in-the-ear hearing aid device, wherein a passage through said connection tube is in fluid-connection with an opening in said housing of said electro-acoustic transducer, wherein said opening is in fluid-connection with said transducer sound active part.

15. The electro-acoustic transducer according to claim 14, wherein said at least one electro-acoustic transducer is one of a microphone and a receiver, and/or said transducer sound active part comprises at least one of a membrane, a diaphragm, an electromagnetic mechanism, and a sound vibrating unit, and/or at least a portion of said at least one sensor and at least a portion of said at least one active electronic component or at least a portion of a first sensor and at least a portion of a second sensor are provided within said transducer air volume, and wherein a line of sight between said portion of said at least one sensor and said portion of said at least one active electronic component or said portion of said first sensor and said portion of said second sensor is shielded by a portion of said electro-acoustic transducer, and/or said capsule comprises at least one measurement opening, and said at least one measurement opening is provided with an electromagnetic filter configured to prevent electromagnetic waves having a frequency lower than a predetermined noise shielding frequency from entering said capsule through said at least one measurement opening, and/or said at least one sensor comprises at least one of a temperature sensing element, a light sensing element, a sound sensing element, a moisture sensing element, a blood oximetry sensor including at least two light emitting elements and a light sensing element, a blood pressure sensor, a blood sugar sensor, a pulse sensor, a hydration sensor, a galvanic skin response electrode, an electroencephalography electrode, and an electrooculography electrode, and/or said at least one active electronic component comprises at least one of a light emitting diode, a pre-processor, a digital sound processor, an amplifier, a pre-amplifier, an AD-converter, a DA-converter, a sensor processing circuitry, a sensor fusion circuitry, a digital speaker communication bus, a bus controller circuitry, a memory, and a microcontroller, and/or said transducer air volume is separated into a first transducer air volume and a second transducer air volume not in fluid-connection with said first transducer air volume, said first transducer air volume is larger in volume than said second transducer air volume, and said portion of said at least one sensor or of said at least one active electronic component is provided within said first transducer air volume.

16. An electro-acoustic transducer, comprising at least one sensor or at least one active electronic component, a capsule enclosing a transducer sound active part and a transducer air volume, wherein said transducer sound active part comprises at least one of a membrane, a diaphragm, an electromagnetic mechanism, and a sound vibrating unit, wherein said transducer air volume is air volume which is enclosed by said capsule and which is in fluid-connection with said transducer sound active part, and wherein at least a portion of said at least one sensor or of said at least one active electronic component is provided within said capsule and said transducer air volume, wherein
  said capsule forms a housing of said electro-acoustic transducer, and
  said capsule includes a microphone inlet of the in-the-ear hearing aid device, wherein a passage through said microphone inlet is in fluid-connection with an inlet opening in said housing of said electro-acoustic transducer, wherein said inlet opening is in fluid-connection with said transducer sound active part.

17. An electro-acoustic transducer, comprising at least one sensor or at least one active electronic component, a capsule enclosing a transducer sound active part and a transducer air volume, wherein said transducer sound active part comprises at least one of a membrane, a diaphragm, an electromagnetic mechanism, and a sound vibrating unit, wherein said transducer air volume is air volume which is enclosed by said capsule and which is in fluid-connection with said transducer sound active part, and wherein at least a portion of said at least one sensor or of said at least one active electronic component is provided within said capsule and said transducer air volume, wherein
  said capsule forms a housing of said electro-acoustic transducer, and said capsule comprises at least one measurement opening, and said at least one measurement opening is provided with an electromagnetic filter configured to prevent electromagnetic waves having a frequency lower than a predetermined noise shielding frequency from entering said capsule through said at least one measurement opening.

* * * * *